(12) United States Patent
Wall et al.

(10) Patent No.: US 9,434,693 B2
(45) Date of Patent: Sep. 6, 2016

(54) SUBSTITUTED PYRAZOLES AS N-TYPE CALCIUM CHANNEL BLOCKERS

(71) Applicant: Janssen Pharmaceutica NV, Beerse (BE)

(72) Inventors: Mark Wall, Lansdale, PA (US); Nalin Subasinghe, Exton, PA (US); Zhihua Sui, Piscataway, NJ (US); Christopher Flores, Lansdale, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/968,465

(22) Filed: Aug. 16, 2013

(65) Prior Publication Data

US 2014/0162997 A1 Jun. 12, 2014

Related U.S. Application Data

(60) Provisional application No. 61/683,774, filed on Aug. 16, 2012.

(51) Int. Cl.

| A61K 31/00 | (2006.01) |
|---|---|
| A61K 31/415 | (2006.01) |
| A61K 31/445 | (2006.01) |
| A61K 31/42 | (2006.01) |
| C07D 401/00 | (2006.01) |
| C07D 231/00 | (2006.01) |
| C07D 403/00 | (2006.01) |
| C07D 403/02 | (2006.01) |
| C07D 261/00 | (2006.01) |
| C07D 413/00 | (2006.01) |
| C07D 231/22 | (2006.01) |
| C07D 401/12 | (2006.01) |
| C07D 403/12 | (2006.01) |
| C07D 405/12 | (2006.01) |
| C07D 409/12 | (2006.01) |
| C07D 413/14 | (2006.01) |

(52) U.S. Cl.
CPC ........... *C07D 231/22* (2013.01); *C07D 401/12* (2013.01); *C07D 403/12* (2013.01); *C07D 405/12* (2013.01); *C07D 409/12* (2013.01); *C07D 413/14* (2013.01)

(58) Field of Classification Search
None
See application file for complete search history.

(56) References Cited

U.S. PATENT DOCUMENTS

| 8,846,949 B2 | 9/2014 | Winters et al. |
|---|---|---|
| 8,853,418 B2 | 10/2014 | Winters et al. |
| 8,901,314 B2 | 12/2014 | Wall et al. |
| 2009/0105296 A1 | 4/2009 | Illig et al. |

FOREIGN PATENT DOCUMENTS

| WO | WO 96/38442 A1 | 12/1996 |
|---|---|---|
| WO | WO 98/22442 | 5/1998 |
| WO | WO 2004/094429 | 11/2004 |
| WO | WO 2005/033073 A2 | 4/2005 |
| WO | WO 2005/073197 | 8/2005 |
| WO | WO 2006/105442 A2 | 10/2006 |
| WO | WO 2007/070201 | 6/2007 |
| WO | 2010021680 A2 | 2/2010 |
| WO | WO 2010/014257 | 2/2010 |

OTHER PUBLICATIONS

Subasinghe, NL. et al. A novel series of pyrazolylpiperdine N-type calcium channel blockers. Bioorganic & Medicinal Chemistry Letters. 2012, vol. 22, p. 4081.*
Bhandari, SV. et al. Design, synthesis and pharmacological screening of novel nitric oxide donors containing 1,5-diarylpyrazolin-3-one as nontoxic NSAIDs. European Journal of Medicinal Chemistry. 2009, vol. 44, p. 4626.*
Subasinghe, N., et al., "A Novel Series of Pyrazolylpiperidine N-Type Calcium Channel Blockers", Bioorganic & Medicinal Chemistry Letters, vol. 22, No. 2, pp. 4080-4083 (2012).
Liu, Y. Y., et al., Synthesis, Crystal Structures and Fungicidal Activity of Novel 1,5-Diaryl-3-(glucopyranosyloxy)-1H-pyrazoles, Helvetica Chimica Acta, vol. 95, No. 13, pp. 1645-1656 (2012).
International Search Report for Application No. PCT/US2013/055263 mailed Oct. 11, 2013.
Belardetti, F., et al., "A Fluorescence-Based High-Throughput Screening Assay for the Identification of T-Type Calcium Channel Blockers", Assay and Drug Development Technologies, vol. 7, pp. 266-280 (2009).
Berge et al., J. Pharm.Sci., Jan. 1977, vol. 66, No. 1, pp. 1-19.
Dai, G., et al. "A High-Throughput Assay for Evaluating State Dependence and Subtype Selectivity of Cav2 Calcium Channel Inhibitors", Assay and Drug Development Technologies, vol. 6, No. 2, pp. 195-212 (2008).
Dixon, W. J., "Efficient Analysis of Experimental Observations", Ann. Rev. Pharmacology.& Toxicology, vol. 20, pp. 441-462 (1980).
Faidallah H M et al., "Synthesis of some sulfonamides, disubstituted sulfonylureas or thioureas and some structurally related variants. A class of promising antitumor agents", Medicinal Chemistry Research, Birkhaeuser, Boston, US, vol. 16, Jan. 1, 2007, pp. 300-318.

(Continued)

*Primary Examiner* — Rita Desai
*Assistant Examiner* — Ben S Michelson

(57) ABSTRACT

Disclosed are compounds, compositions and methods for treating various diseases, syndromes, conditions and disorders, including pain. Such compounds are represented by Formula I as follows:

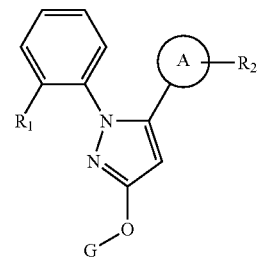

Formula (I)

wherein $R_1$, $R_2$, ring A, and G are defined herein.

20 Claims, 1 Drawing Sheet

(56) References Cited

OTHER PUBLICATIONS

Finley, M., et al., "An Integrated Multiassay Approach to the Discovery of Small-Molecular N-Type Voltage-Gated Calcium Channel Antagonists", Assay and Drug Development Technologies, vol. 8(6), pp. 685-694 (2010).
Gould et al., Ref. International J. Pharm., 1986, 33, 201-217.
Kim, Sun Ho., et al., An Experimental Model for Peripheral Neuropathy Produced by Segmental Spinal Nerve Ligation in the Rat', Pain, vol. 50, pp. 355-363 (1992).
Lim et al., Org. Lett., 2007, 9(21), pp. 4139-4142.
Nielsen, C., et al., "Anti-Allodynic Efficacy of the $_\chi$-Conopeptide, Xen2174 in Rats with Neuropathic Pain", Pain, vol. 118, pp. 112-124 (2005).
Reddy et al., J. Org. Chem, vol. 69, p. 1716, 2004.
International Search Report re: PCT/US2013/055267 dated Dec. 17, 2013.
International Search Report re: PCT/US2013/055271 dated Oct. 10, 2013.
International Search Report re: PCT/US2013/055275 dated Oct. 21, 2013.
International Search Report re: PCT/US2013/055282 dated Oct. 31, 2013.

* cited by examiner

Resultant data for Compound 23 in a rat CFA radiant heat model of inflammatory pain.
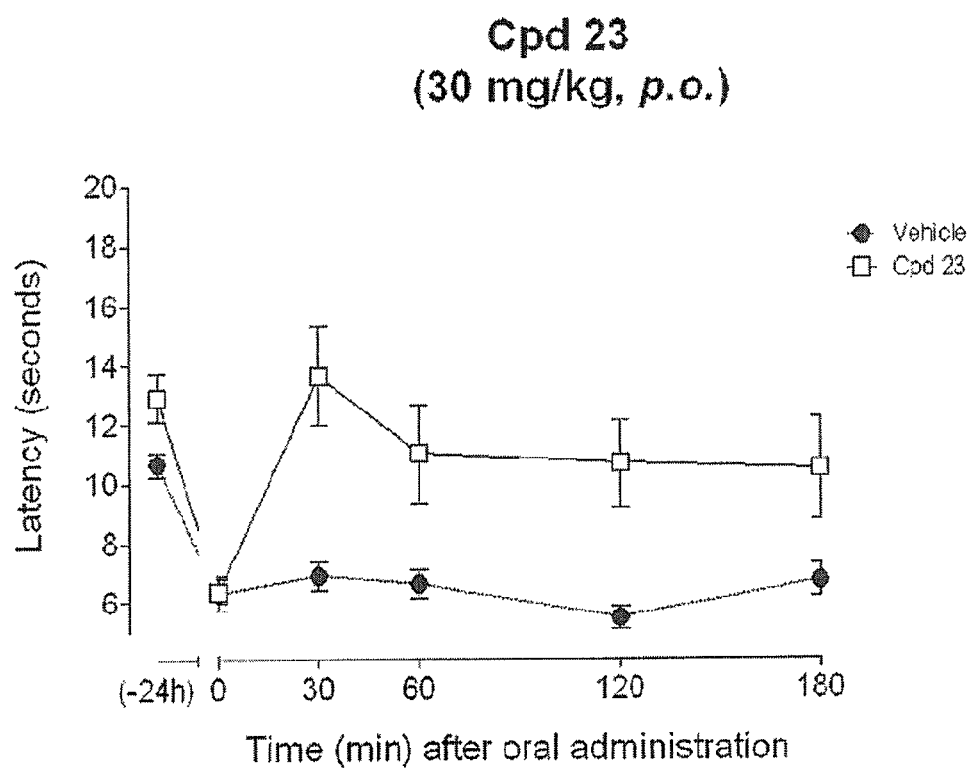

SUBSTITUTED PYRAZOLES AS N-TYPE CALCIUM CHANNEL BLOCKERS

CROSS-REFERENCE TO RELATED APPLICATIONS

This application claims priority of the benefits of the filing of U.S. Provisional Application Ser. No. 61/683,774, filed Aug. 16, 2012. The complete disclosures of the aforementioned related U.S. patent application is/are hereby incorporated herein by reference for all purposes.

STATEMENT REGARDING FEDERALLY SPONSORED RESEARCH OR DEVELOPMENT

The research and development of the invention described below was not federally sponsored.

BACKGROUND OF THE INVENTION

Calcium ions play a fundamental role in the physiology and biochemistry of organisms and of cells. The entry of calcium into cells through ion channels mediates a variety of cellular and physiological responses, including gene expression, signal transduction, neurotransmitter release, muscle contraction and hormone secretion. Ion channels are classified by gating, or what opens and closes the channel to the flux of ions. Voltage-gated ion channels open or close depending on the voltage gradient across the plasma membrane, whereas ligand-gated ion channels open or close depending on the binding of ligands to the channel. The classification of voltage-gated calcium channels divides them into three groups: (i) high voltage-activated channels, which include L-, N-, P- and Q-type channels; (ii) intermediate voltage-activated R-type channels; and (iii) low voltage-activated T-type channels.

The N-type calcium channel is distributed mainly in central and peripheral neurons, being localized primarily to presynaptic nerve terminals. This channel regulates the calcium flux required for depolarization-evoked release of neurotransmitters from synaptic endings. The transmission of pain signals from the periphery to the central nervous system (CNS) is mediated, inter alia, by N-type calcium channels located in the spinal cord. Inhibition of the N-type calcium channel in the superficial dorsal horn leads to a decrease in membrane excitability and neurotransmitter release, resulting in pain relief In addition, knock-out mice lacking the N-type calcium channel exhibit reduced nociceptive behaviors in animal models of pain.

N-type calcium channels have been shown to mediate the development and maintenance of the neuronal sensitization processes associated with neuropathic pain and therefore provide attractive targets for the development of analgesic drugs. Three N-type calcium channel modulators are currently approved for the treatment of pain: ω-conotoxin MVIIA (ziconotide), marketed as Prialt®, potently and selectively blocks the N-type calcium channel and is indicated for the management of severe chronic pain; gabapentin, marketed as Neurontin®, and pregabalin, marketed as Lyrica®, bind with high affinity to the α2δ subunit of the N-type calcium channel and are indicated for the treatment of fibromyalgia, diabetic nerve pain and/or post-herpetic neuralgia pain.

It is an object of the present invention to provide N-Type calcium channel blockers. It is also an object of the invention to provide a method of treating, ameliorating or preventing pain by the administration of a compound of Formula (I). And, it is an object of the invention to provide a pharmaceutical composition comprising a compound of Formula (I), useful for treating, ameliorating or preventing pain.

SUMMARY OF THE INVENTION

The present invention is directed to a compound of Formula (I)

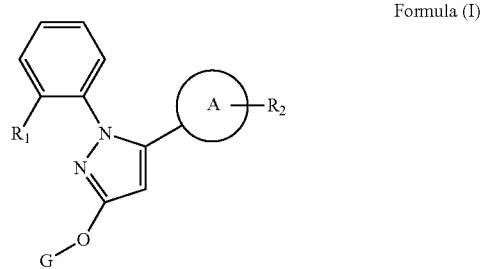

Formula (I)

wherein $R^1$ is selected from the group consisting of $C_{1-4}$alkyl, $C_{1-4}$alkoxy, di($C_{1-4}$alkyl)amino, chloro, trifluoromethoxy, trifluoromethyl, and cyano;

ring A is phenyl or a heteroaryl selected from the group consisting of pyridinyl, thienyl, benzofuranyl, quinolinyl, and indolyl;

$R^2$ is selected from the group consisting of $C_{1-4}$alkyl, $C_{1-4}$alkoxy, $C_{1-4}$alkylthio, cyano, fluoro, chloro, hydroxy, and di($C_{1-4}$alkyl)amino;

G is G1, G2, G3, or G4;

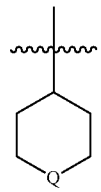

G1

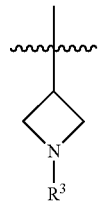

G2

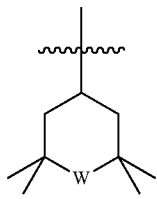

G3

-continued

G4
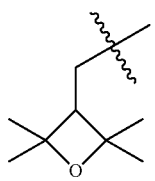

wherein

Q is selected from the group consisting of O, S, SO$_2$, N—R$^4$, CH$_2$, CH(R$^5$), CF$_2$, C(CH$_3$)$_2$, C(O), and a spirofused

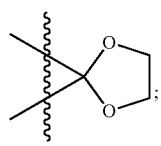

W is selected from the group consisting of O, S, CH(OH), C(O), S(O), SO$_2$, and N—R$^4$;

R$^3$ and R$^4$ are each independently selected from the group consisting of 2,2,2-trifluoroethyl, di(C$_{1-4}$alkyl)aminocarbonyl, N-methoxy-N-methylaminocarbonyl, phenylcarbonyl, C$_{1-4}$alkylcarbonyl, trifluoromethylcarbonyl, C$_{1-4}$alkoxycarbonyl, C$_{1-4}$alkylsulfonyl, C$_{3-7}$cycloalkylsulfonyl, trifluoromethylsulfonyl, and 3,5-dimethylisoxazol-4-ylsulfonyl;

R$^5$ is trifluoromethylcarbonylamino, amino, or C$_{1-4}$alkoxycarbonylamino;

and enantiomers, diastereomers, solvates and pharmaceutically acceptable salts thereof.

The present invention also provides, inter alia, a pharmaceutical composition comprising, consisting of and/or consisting essentially of a pharmaceutically acceptable carrier, a pharmaceutically acceptable excipient, and/or a pharmaceutically acceptable diluent, and a compound of Formula (I), or a pharmaceutically acceptable salt form thereof.

Also provided are processes for making a pharmaceutical composition comprising, consisting of, and/or consisting essentially of admixing a compound of Formula (I) and a pharmaceutically acceptable carrier, a pharmaceutically acceptable excipient, and/or a pharmaceutically acceptable diluent.

The present invention further provides, inter alia, methods for treating or ameliorating a N-Type calcium channel-modulated disorder in a subject, including a human or other mammal in which the disease, syndrome, or condition is affected by the modulation of the N-Type calcium channel, such as pain and the diseases that lead to such pain, using a compound of Formula (I).

The present invention also provides, inter alia, methods for producing the instant compounds and pharmaceutical compositions and medicaments thereof.

BRIEF DESCRIPTION OF THE DRAWINGS

FIG. 1 shows the antihyperalgesic effect of Compound 23 in a rat CFA radiant heat model of inflammatory pain.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g. C$_{1-8}$) refer independently to the number of carbon atoms in an alkyl moiety or to the alkyl portion of a larger alkyl-containing substituent. In substituent groups with multiple alkyl groups such as (C$_{1-6}$alkyl)$_2$amino-, the C$_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 or more carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl and adamantyl.

The term "benzo-fused cycloalkyl" refers to a 5- to 8-membered monocyclic cycloalkyl ring fused to a benzene ring. The carbon atom ring members that form the cycloalkyl ring may be fully saturated or partially saturated.

The term "heterocyclyl" refers to a nonaromatic monocyclic or bicyclic ring system having 3 to 10 ring members and which contains carbon atoms and from 1 to 4 heteroatoms independently selected from the group consisting of N, O, and S. Included within the term heterocyclyl is a nonaromatic cyclic ring of 5 to 7 members in which 1 to 2 members are nitrogen, or a nonaromatic cyclic ring of 5 to 7 members in which 0, 1 or 2 members are nitrogen and up to 2 members are oxygen or sulfur and at least one member must be either nitrogen, oxygen or sulfur; wherein, optionally, the ring contains zero to one unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "benzo-fused heterocyclyl" refers to a 5 to 7 membered monocyclic heterocycle ring fused to a benzene ring. The heterocycle ring contains carbon atoms and from 1 to 4 heteroatoms independently selected from the group consisting of N, O, and S. The carbon atom ring members that form the heterocycle ring may be fully saturated or partially saturated. Unless otherwise noted, benzo-fused heterocycle ring is attached to its pendant group at a carbon atom of the benzene ring. The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine.

The term "formyl" refers to the group —C(═O)H.

The term "oxo" refers to the group (═O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

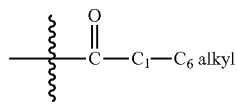

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of 2 enantiomers. Compounds containing 2 stereocenters both drawn without stereo bond designations are a mixture of 4 diastereomers. Compounds with 2 stereocenters both labeled "RS" and drawn with stereo bond designations are a 2-component mixture with relative stereochemistry as drawn. Compounds with 2 stereocenters both labeled "*RS" and drawn with stereo bond designations are a 2-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of Formula (I) can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "N-Type calcium channel blocker" is intended to encompass a compound that interacts with the N-Type calcium channel to substantially reduce or eliminate its functional activity, thereby decreasing the flow of calcium ions through the channel and the rise of intracellular calcium concentrations.

The term "N-Type calcium channel-modulated" is used to refer to the condition of being affected by the modulation of the N-Type calcium channel, including the condition of being affected by the inhibition of the N-Type calcium channel, such as, for example, pain, the diseases that lead to such pain and treatments that lead to the reduction of such pain.

As used herein, unless otherwise noted, the term "affect" or "affected" (when referring to a disease, syndrome, condition or disorder that is affected by the inhibition of N-Type calcium channel) shall include a reduction in the frequency and/or severity of one or more symptoms or manifestations of said disease, syndrome, condition or disorder and/or include the prevention of the development of one or more symptoms or manifestations of said disease, syndrome, condition or disorder or the development of the disease, condition, syndrome or disorder.

The compounds of Formula (I) are useful in methods for treating, ameliorating and/or preventing a disease, a syndrome, a condition or a disorder that is affected by the inhibition of N-Type calcium channel. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt form thereof. In particular, the compounds of Formula (I) are useful for treating, ameliorating and/or preventing pain as well as diseases, syndromes, conditions or disorders causing such pain. More particularly, the compounds of Formula (I) are useful for treating, ameliorating and/or preventing acute pain, inflammatory pain and/or neuropathic pain, comprising administering to a subject in need thereof a therapeutically effective amount of a compound of Formula (I), as herein defined.

Acute pain, as used herein, refers to pain that comes on quickly, can be of varying severity but is self-limiting and of relatively short duration. Examples of acute pain include, but are not limited to, post-operative pain, post-surgical pain, toothache, burn, sunburn, insect/animal bites and stings, headache and/or any pain associated with acute trauma or injury.

Inflammatory pain refers to pain arising from an inflammatory disease, condition, syndrome or disorder, including but not limited to inflammatory bowel disease, irritable bowel sysdrome, visceral pain, migraine, post-operative pain, osteoarthritis, rheumatoid arthritis, back pain, low back pain, joint pain, abdominal pain, chest pain, labor pain, musculoskeletal diseases, skin diseases, toothache, pyresis, burn, sunburn, snake bite, venomous snake bite, spider bite, insect sting, neurogenic or overactive bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, post-mastectomy pain syndrome, menstrual pain, endometriosis, pain due to physical trauma, headache, sinus headache, tension headache or arachnoiditis.

A further embodiment of the present invention is directed to a method for treating, ameliorating and/or preventing neuropathic pain. Neuropathic pain refers to a disease, syndrome, condition and/or disorder involving damage to the peripheral or central nervous system, including cancer pain, neurological disorders, spine and peripheral nerve surgery, brain tumor, traumatic brain injury (TBI), chemotherapy-induced pain, pain chronification, radicular pain, HIV pain, spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, post-herpetic neuralgia, causalgia, red neuralgia, Sluder's neuralgia, splenopalatine neuralgia, supraorbital neuralgia, trigeminal neuralgia, vulvodynia, or vidian neuralgia.

Embodiments of the present invention include a compound of Formula (I)

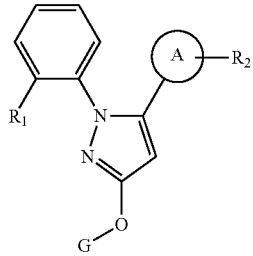

Formula (I)

wherein
a) $R^1$ is selected from the group consisting of $C_{1-4}$alkyl, $C_{1-4}$alkoxy, chloro, trifluoromethoxy, trifluoromethyl, and cyano;
b) $R^1$ is selected from the group consisting of $C_{1-4}$alkyl, $C_{1-4}$alkoxy, chloro, and trifluoromethyl;
c) $R^1$ is selected from the group consisting of methyl, ethyl, methoxy, and isopropyloxy;
d) ring A is phenyl;
e) ring A is phenyl substituted at the 4-position;
f) $R^2$ is selected from the group consisting of $C_{1-4}$alkoxy, cyano, and chloro;
g) $R^2$ is selected from the group consisting of methoxy, cyano, and chloro;
h) G is G1, G2, G3, or G4;

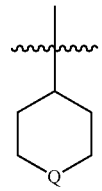

G1

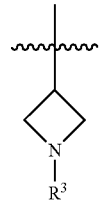

G2

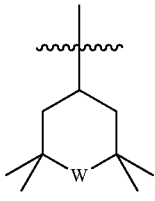

G3

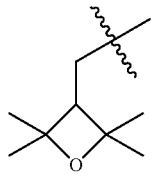

G4 wherein
Q is selected from the group consisting of O, S, $SO_2$, N—$R^4$, $CH_2$, $CH(R^5)$, $CF_2$, $C(CH_3)_2$, C(O), and a spirofused

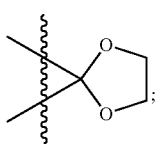

W is selected from the group consisting of O, S, CH(OH), C(O), S(O), and SO$_2$;

$R^3$ and $R^4$ are each independently selected from the group consisting of 2,2,2-trifluoroethyl, di(C$_{1-4}$alkyl)aminocarbonyl, N-methoxy-N-methylaminocarbonyl, phenylcarbonyl, C$_{1-4}$alkylcarbonyl, trifluoromethylcarbonyl, C$_{1-4}$alkoxycarbonyl, C$_{1-4}$alkylsulfonyl, C$_{3-7}$cycloalkylsulfonyl, trifluoromethylsulfonyl, and 3,5-dimethylisoxazol-4-ylsulfonyl;

$R^5$ is trifluoromethylcarbonylamino or C$_{1-4}$alkoxycarbonylamino;

and any combination of embodiments a) through h) above, provided that it is understood that combinations in which different embodiments of the same substituent would be combined are excluded;

and enantiomers, diastereomers, solvates and pharmaceutically acceptable salts thereof.

An embodiment of the present invention is directed to a compound of Formula (I)

Formula (I)

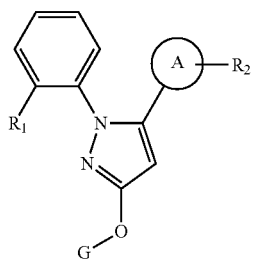

wherein $R^1$ is selected from the group consisting of C$_{1-4}$alkyl, C$_{1-4}$alkoxy, chloro, trifluoromethoxy, trifluoromethyl, and cyano;

ring A is phenyl or a heteroaryl selected from the group consisting of pyridinyl, thienyl, benzofuranyl, quinolinyl, and indolyl;

$R^2$ is selected from the group consisting of C$_{1-4}$alkoxy, cyano, and chloro;

G is G1, G2, G3, or G4;

G1

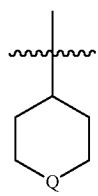

G2

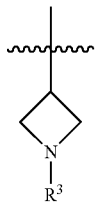

G3

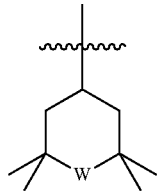

G4

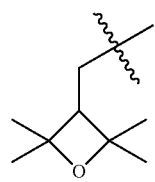

wherein

Q is selected from the group consisting of O, S, SO$_2$, N—R$^4$, CH$_2$, CH(R$^5$), CF$_2$, C(CH$_3$)$_2$, C(O), and a spirofused

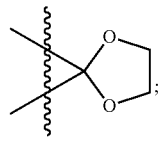

W is selected from the group consisting of O, S, CH(OH), C(O), S(O), and SO$_2$;

$R^3$ and $R^4$ are each independently selected from the group consisting of 2,2,2-trifluoroethyl, di(C$_{1-4}$alkyl)aminocarbonyl, N-methoxy-N-methylaminocarbonyl, phenylcarbonyl, C$_{1-4}$alkylcarbonyl, trifluoromethylcarbonyl, C$_{1-4}$alkoxycarbonyl, C$_{1-4}$alkylsulfonyl, C$_{3-7}$cycloalkylsulfonyl, trifluoromethylsulfonyl, and 3,5-dimethylisoxazol-4-ylsulfonyl;

$R^5$ is trifluoromethylcarbonylamino or C$_{1-4}$alkoxycarbonylamino;

and enantiomers, diastereomers, solvates and pharmaceutically acceptable salts thereof.

An embodiment of the present invention is directed to a compound of Formula (I)

Formula (I)

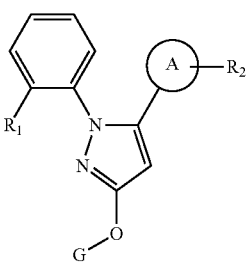

wherein

R¹ is selected from the group consisting of $C_{1-4}$alkyl, $C_{1-4}$alkoxy, chloro, and trifluoromethyl;

ring A is phenyl;

R² is selected from the group consisting of $C_{1-4}$alkoxy, cyano, and chloro;

G is G1, G2, G3, or G4;

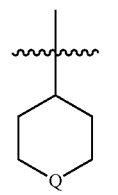

G1

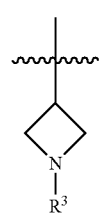

G2

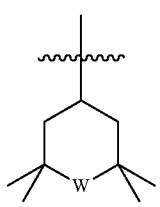

G3

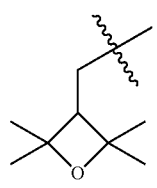

G4 wherein

Q is selected from the group consisting of O, S, SO₂, N—R⁴, CH₂, CH(R⁵), CF₂, C(CH₃)₂, C(O), and a spirofused

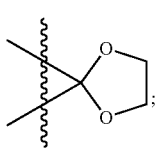

W is selected from the group consisting of O, S, CH(OH), C(O), S(O), and SO₂;

R³ and R⁴ are each independently selected from the group consisting of 2,2,2-trifluoroethyl, di($C_{1-4}$alkyl)aminocarbonyl, N-methoxy-N-methylaminocarbonyl, phenylcarbonyl, $C_{1-4}$alkylcarbonyl, trifluoromethylcarbonyl, $C_{1-4}$alkoxycarbonyl, $C_{1-4}$alkylsulfonyl, $C_{3-7}$cycloalkylsulfonyl, trifluoromethylsulfonyl, and 3,5-dimethylisoxazol-4-ylsulfonyl;

R⁵ is trifluoromethylcarbonylamino or $C_{1-4}$alkoxycarbonylamino;

and enantiomers, diastereomers, solvates and pharmaceutically acceptable salts thereof.

An embodiment of the present invention is directed to a compound of Formula (I)

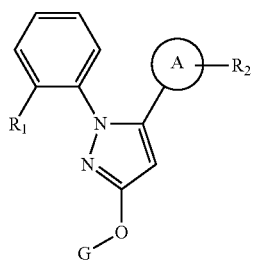

Formula (I)

wherein

R¹ is selected from the group consisting of methyl, ethyl, methoxy, and isopropyloxy;

ring A is phenyl substituted at the 4-position;

R² is selected from the group consisting of methoxy, cyano, and chloro;

G is G1, G2, G3, or G4;

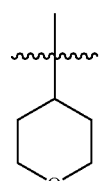

G1

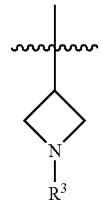

G2

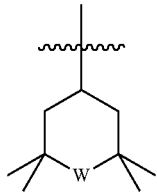

G3

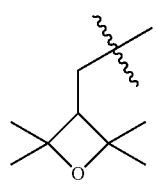

G4 wherein

Q is selected from the group consisting of O, S, SO₂, N—R⁴, CH₂, CH(R⁵), CF₂, C(CH₃)₂, C(O), and a spirofused

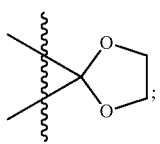

W is selected from the group consisting of O, S, CH(OH), C(O), S(O), and $SO_2$;

$R^3$ and $R^4$ are each independently selected from the group consisting of 2,2,2-trifluoroethyl, di($C_{1-4}$alkyl)aminocarbonyl, N-methoxy-N-methylaminocarbonyl, phenylcarbonyl, $C_{1-4}$alkylcarbonyl, trifluoromethylcarbonyl, $C_{1-4}$alkoxycarbonyl, $C_{1-4}$alkylsulfonyl, $C_{3-7}$cycloalkylsulfonyl, trifluoromethylsulfonyl, and 3,5-dimethylisoxazol-4-ylsulfonyl;

$R^5$ is trifluoromethylcarbonylamino or $C_{1-4}$alkoxycarbonylamino;

and enantiomers, diastereomers, solvates and pharmaceutically acceptable salts thereof.

Further embodiments of the present invention are directed to a compound of Formula (I)

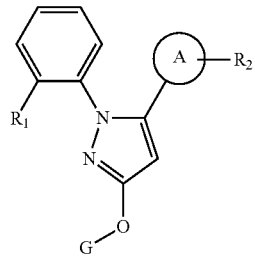

Formula (I)

selected from the group consisting of
tert-Butyl 4-{[5-(4-chlorophenyl)-1-(2-methoxyphenyl)-1H-pyrazol-3-yl]oxy}piperidine-1-carboxylate;
4-{[5-(4-Chlorophenyl)-1-(2-methoxyphenyl)-1H-pyrazol-3-yl]oxy}cyclohexanone;
1-Acetyl-4-{[5-(4-chlorophenyl)-1-(2-methoxyphenyl)-1H-pyrazol-3-yl]oxy}piperidine;
4-{[5-(4-Chlorophenyl)-1-(2-methoxyphenyl)-1H-pyrazol-3-yl]oxy}-N,N-dimethylpiperidine-1-carboxamide;
4-{[5-(4-Chlorophenyl)-1-(2-methoxyphenyl)-1H-pyrazol-3-yl]oxy}-1-(methylsulfonyl)piperidine;
5-(4-Chlorophenyl)-1-(2-methoxyphenyl)-3-(tetrahydro-2H-pyran-4-yloxy)-1H-pyrazole;
5-(4-Chlorophenyl)-1-(2-methoxyphenyl)-3-(tetrahydro-2H-thiopyran-4-yloxy)-1H-pyrazole;
4-{[5-(4-Chlorophenyl)-1-(2-methoxyphenyl)-1H-pyrazol-3-yl]oxy}-1-(2,2,2-trifluoroethyl)piperidine;
4-{[5-(4-Chlorophenyl)-1-(2-methoxyphenyl)-1H-pyrazol-3-yl]oxy}-1-(trifluoroacetyl)piperidine;
5-(4-Chlorophenyl)-3-[(1,1-dioxidotetrahydro-2H-thiopyran-4-yl)oxy]-1-(2-methoxyphenyl)-1H-pyrazole;
tert-Butyl (cis-4-{[5-(4-chlorophenyl)-1-(2-methoxyphenyl)-1H-pyrazol-3-yl]oxy}cyclohexyl)carbamate;
cis-4-{[5-(4-Chlorophenyl)-1-(2-methoxyphenyl)-1H-pyrazol-3-yl]oxy}cyclohexanamine;
N-(cis-4-{[5-(4-Chlorophenyl)-1-(2-methoxyphenyl)-1H-pyrazol-3-yl]oxy}cyclohexyl)-2,2,2-trifluoroacetamide;
4-{[5-(4-Chlorophenyl)-1-(2-methoxyphenyl)-1H-pyrazol-3-yl]oxy}-1-[(trifluoromethyl)sulfonyl]piperidine;
4-{[5-(4-Chlorophenyl)-1-(2-methoxyphenyl)-1H-pyrazol-3-yl]oxy}-1-(cyclopropylsulfonyl)piperidine;
5-(4-Chlorophenyl)-3-[(4,4-difluorocyclohexyl)oxy]-1-(2-methoxyphenyl)-1H-pyrazole;
5-(4-Chlorophenyl)-3-(1,4-dioxaspiro[4.5]dec-8-yloxy)-1-(2-ethylphenyl)-1H-pyrazole;
tert-Butyl 4-{[5-(4-chlorophenyl)-1-(2-ethylphenyl)-1H-pyrazol-3-yl]oxy}piperidine-1-carboxylate;
4-{[5-(4-Chlorophenyl)-1-(2-ethylphenyl)-1H-pyrazol-3-yl]oxy}-1-(methylsulfonyl)piperidine;
4-({5-(4-Chlorophenyl)-1-[2-(1-methylethoxy)phenyl]-1H-pyrazol-3-yl}oxy)-1-(methylsulfonyl)piperidine;
4-{[5-(4-Chlorophenyl)-1-(2-methoxyphenyl)-1H-pyrazol-3-yl]oxy}-1-[(1-methylethyl)sulfonyl]piperidine;
tert-Butyl 3-{[5-(4-chlorophenyl)-1-(2-methoxyphenyl)-1H-pyrazol-3-yl]oxy}azetidine-1-carboxylate;
5-(4-Chlorophenyl)-1-(2-methoxyphenyl)-3-[(2,2,6,6-tetramethyltetrahydro-2H-pyran-4-yl)oxy]-1H-pyrazole;
4-{[1-(2-tert-Butoxyphenyl)-5-(4-chlorophenyl)-1H-pyrazol-3-yl]oxy}-1-(methylsulfonyl)piperidine;
5-(4-Chlorophenyl)-1-(2-methoxyphenyl)-3-({1-[(1-methylethyl)sulfonyl]azetidin-3-yl}oxy)-1H-pyrazole;
5-(4-Chlorophenyl)-1-(2-methoxyphenyl)-3-{[1-(methylsulfonyl)azetidin-3-yl]oxy}-1H-pyrazole;
5-(4-Chlorophenyl)-1-(2-methoxyphenyl)-3-{[1-(phenylcarbonyl)azetidin-3-yl]oxy}-1H-pyrazole;
4-({5-(4-Chlorophenyl)-1-[2-(1-methylethoxy)phenyl]-1H-pyrazol-3-yl}oxy)-1-[(1-methylethyl)sulfonyl]piperidine;
3-{[5-(4-Chlorophenyl)-1-(2-methoxyphenyl)-1H-pyrazol-3-yl]oxy}-N-methoxy-N-methylazetidine-1-carboxamide;
4-[(3-{[5-(4-Chlorophenyl)-1-(2-methoxyphenyl)-1H-pyrazol-3-yl]oxy}azetidin-1-yl)sulfonyl]-3,5-dimethylisoxazole;
1-(2-Methoxyphenyl)-5-(4-methoxyphenyl)-3-[(2,2,6,6-tetramethyltetrahydro-2H-pyran-4-yl)oxy]-1H-pyrazole;
1-(2-Methoxyphenyl)-5-(4-methoxyphenyl)-3-[(2,2,6,6-tetramethyltetrahydro-2H-thiopyran-4-yl)oxy]-1H-pyrazole;
1-(2-Methoxyphenyl)-5-(4-methoxyphenyl)-3-[(2,2,6,6-tetramethyl-1,1-dioxidotetrahydro-2H-thiopyran-4-yl)oxy]-1H-pyrazole;
(1r,4r)-4-((1-(2-methoxyphenyl)-5-(4-methoxyphenyl)-1H-pyrazol-3-yl)oxy)-2,2,6,6-tetramethyltetrahydro-2H-thiopyran 1-oxide;
(1s,4s)-4-((1-(2-methoxyphenyl)-5-(4-methoxyphenyl)-1H-pyrazol-3-yl)oxy)-2,2,6,6-tetramethyltetrahydro-2H-thiopyran 1-oxide;
5-(4-Chlorophenyl)-1-(2-methoxyphenyl)-3-[(2,2,6,6-tetramethyltetrahydro-2H-thiopyran-4-yl)oxy]-1H-pyrazole;
5-(4-Chlorophenyl)-1-(2-methoxyphenyl)-3-[(2,2,6,6-tetramethyl-1,1-dioxidotetrahydro-2H-thiopyran-4-yl)oxy]-1H-pyrazole;
(1r,4r)-4-((5-(4-chlorophenyl)-1-(2-methoxyphenyl)-1H-pyrazol-3-yl)oxy)-2,2,6,6-tetramethyltetrahydro-2H-thiopyran 1-oxide;
(1s,4s)-4-((5-(4-chlorophenyl)-1-(2-methoxyphenyl)-1H-pyrazol-3-yl)oxy)-2,2,6,6-tetramethyltetrahydro-2H-thiopyran 1-oxide;
5-(4-Chlorophenyl)-1-(2-methoxyphenyl)-3-[(2,2,4,4-tetramethyloxetan-3-yl)methoxy]-1H-pyrazole;
4-{[5-(4-Chlorophenyl)-1-(2-methoxyphenyl)-1H-pyrazol-3-yl]oxy}-2,2,6,6-tetramethylcyclohexanone;
4-{[5-(4-Chlorophenyl)-1-(2-methoxyphenyl)-1H-pyrazol-3-yl]oxy}-2,2,6,6-tetramethylcyclohexanol;
4-{1-(2-Methoxyphenyl)-3-[(2,2,6,6-tetramethyltetrahydro-2H-pyran-4-yl)oxy]-1H-pyrazol-5-yl}benzonitrile;
4-{1-(2-Methoxyphenyl)-3-[(2,2,6,6-tetramethyltetrahydro-2H-thiopyran-4-yl)oxy]-1H-pyrazol-5-yl}benzonitrile;
4-{1-(2-Methoxyphenyl)-3-[(2,2,6,6-tetramethyl-1,1-dioxidotetrahydro-2H-thiopyran-4-yl)oxy]-1H-pyrazol-5-yl}benzonitrile;
4-[1-(2-Methoxyphenyl)-3-{[(1s)-2,2,6,6-tetramethyl-1-oxidotetrahydro-2H-thiopyran-4-yl]oxy}-1H-pyrazol-5-yl]benzonitrile;

and pharmaceutically acceptable salt forms thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salts thereof. Suitable pharmaceutically acceptable salts of compounds of Formula (I) include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts, such as sodium or potassium salts; alkaline earth metal salts, such as calcium or magnesium salts; and salts formed with suitable organic ligands, such as quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases that may be used in the preparation of pharmaceutically acceptable salts include acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, a-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

Where the processes for the preparation of the compounds according to certain embodiments of the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as.

$$\%(+)\text{-enantiomer} = \frac{(\text{mass}(+)\text{-enantiomer})}{(\text{mass}(+)\text{-enantiomer}) + (\text{mass}(-)\text{-enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups, such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms, such as tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a white wax or white soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example intracavernosally, intravenously, intramuscularly, subcutaneously, intradermally or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus for liquid oral preparations, such as suspensions, syrups, elixirs and solutions, suitable carriers, excipients and diluents include water, glycols, oils, alcohols, flavoring agents, preservatives, stabilizers, coloring agents and the like; for solid oral preparations, such as powders, capsules and tablets, suitable carriers, excipients and diluents include starches, sugars, diluents, granulating agents, lubricants, binders, disintegrating agents and the like. Solid oral preparations also may be optionally coated with substances, such as, sugars, or be enterically-coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives, such as solubilizers and preservatives.

A therapeutically effective amount of a compound of Formula (I) or a pharmaceutical composition thereof includes a dose range from about 0.1 mg to about 3000 mg, or any particular amount or range therein, in particular from about 1 mg to about 1000 mg, or any particular amount or range therein; or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) will vary as will the diseases, syndromes, conditions, and disorders being treated.

For oral administration, a pharmaceutical composition is preferably provided in the form of tablets containing about 0.01, about 10, about 50, about 100, about 150, about 200, about 250, and about 500 milligrams of a compound of Formula (I).

Advantageously, a compound of Formula (I) may be administered in a single daily dose, or the total daily dosage may be administered in divided doses of two, three and four times daily.

Optimal dosages of a compound of Formula (I) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

As N-Type calcium channel blockers, the compounds of Formula (I) are useful in methods for treating and/or preventing a disease, a syndrome, a condition or a disorder in a subject, including an animal, a mammal and a human in which the disease, the syndrome, the condition or the disorder is affected by the modulation of the N-Type calcium channel. Such methods comprise, consist of and/or consist essentially of administering to a subject, including an animal, a mammal, and a human in need of such treatment or prevention a therapeutically effective amount of a compound, salt or solvate of Formula (I). In particular, the compounds of Formula (I) are useful for preventing or treating pain, such as inflammatory pain or neuropathic pain, or diseases, syndromes, conditions or disorders causing such pain.

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes. The various starting materials used in the schemes and examples are commercially available or may be prepared by methods well within the skill of persons versed in the art. The variables are as defined herein.

Abbreviations used in the instant specification, particularly the schemes and examples, are as follows:
ACN acetonitrile
AcOH glacial acetic acid
aq. aqueous
Bn or Bzl benzyl
Boc tert-butyloxycarbonyl
conc. concentrated
DCE 1,2-dichloroethane
DCM dichloromethane
DIPEA or DIEA diisopropyl-ethyl amine
DMF N,N-dimethylformamide
DMSO dimethylsulfoxide
EA ethyl acetate
EGTA ethylene glycol tetraacetic acid
ESI electrospray ionization
EtOAc or EA ethyl acetate
EtOH ethanol
hr hour or hours
HEK human embryonic kidney
HEPES (4-(2-hydroxyethyl)-1-piperazineethane sulfonic acid
HPLC high performance liquid chromatography
mCPBA meta-chloroperoxybenzoic acid
MeOH methanol
MHz megahertz
min minute or minutes
MS mass spectrometry
Ms methanesulfonyl
NMR nuclear magnetic resonance
RP reverse-phase
RT room temperature
$R_t$ retention time
Sec second or seconds
TEA or $Et_3N$ triethylamine
TFA trifluoroacetic acid
THF tetrahydrofuran
TLC thin layer chromatography
TMS tetramethylsilane Scheme A illustrates a route for the synthesis of certain G3 intermediates falling within the scope of variable G of Formula (I), that are useful toward the preparation of compounds of the instant invention, wherein G is G3 and W is O, S, S(O), or $S(O_2)$.

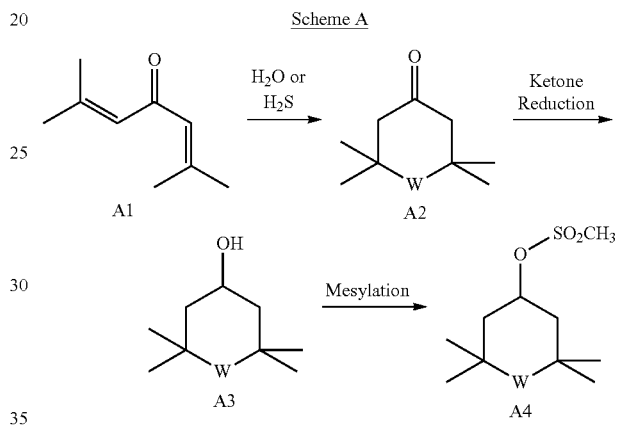

Scheme A

Useful intermediates of Formula A2 are either commercially available or may be prepared by methods known in the scientific literature, such as that described herein. A compound of Formula A1 may undergo either acid- or base-catalyzed double Michael addition reactions with a nucleophile such as $H_2O$, at a temperature of about 40-50° C., for about four days, with excess 1-4 N aqueous HCl, to afford a compound of Formula A2 wherein W is O.

Similarly, a compound of Formula A2 wherein W is S may be prepared, using $H_2S$ as the nucleophile, in the presence of an inorganic base such as KOH, with or without a catalytic amount of an organic amine such as piperidine, in a protic solvent such as ethanol, under reflux conditions with continuous slow bubbling of $H_2S$. One of ordinary skill in the art will recognize that when W is S, the sulfur can be oxidized with one or two equivalents of an appropriate oxidizing agent, such as m-chloroperbenzoic acid, to obtain compounds wherein W is S(O) or $S(O_2)$, respectively.

The compound of Formula A2 may be reduced to its corresponding alcohol in the presence of a conventional reducing agent such as sodium borohydride, in an aprotic organic solvent such as THF, to afford a compound of Formula A3. The compound of Formula A3 may be converted to its corresponding mesylate by the action of methanesulfonyl chloride, in the presence of a non-nucleophilic tertiary amine base such as pyridine, at an initial temperature of about 0° C., to afford a compound of Formula A4.

Scheme B illustrates a route for the synthesis of compounds of Formula (1)-B wherein $R_1$, $R_2$, and ring A are as defined herein and $G_B$ is G1, G2, or G4.

Scheme B

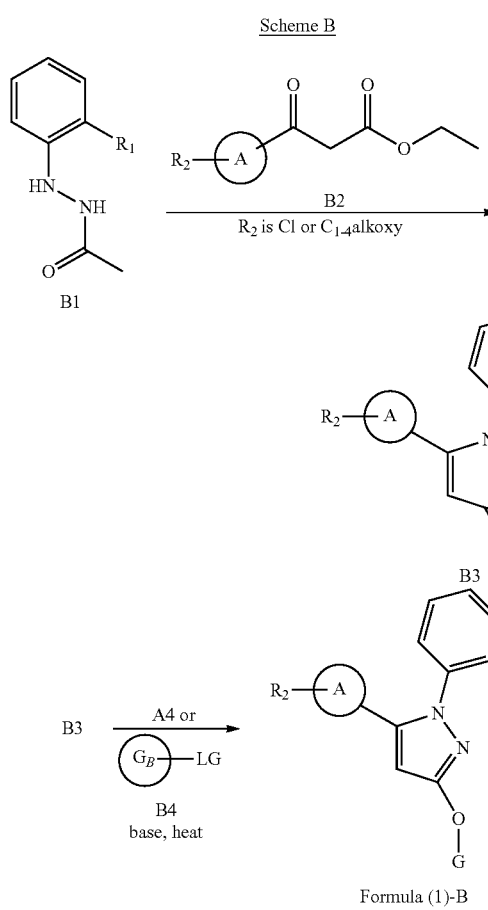

Compounds of Formulae B1 and B2 are either commercially available or may be prepared by methods known in the scientific literature. A compound of Formula B1 may be condensed and subsequently cyclized with a compound of Formula B2 in the presence of an appropriate Lewis acid, such as phosphorus trichloride, in an organic solvent such as dichloromethane, while heating to a temperature between about room temperature and about 50 to 60° C., to form a compound of Formula B3.

Compounds of Formula B4 are either commercially available or may be prepared by methods known in the scientific literature. A compound of Formula B3 may be treated with a compound of Formula A4 or a compound of Formula B4, wherein $G_B$ is G1, G2, or G4 and LG is a suitable leaving group such as, but not limited to, bromide, iodide, mesylate, or tosylate. The reaction may be carried out in the presence of an inorganic base such as cesium carbonate, in an aprotic organic solvent such as toluene and the like, at a temperature of about 115° C., to afford a compound of Formula (I)-B.

One of ordinary skill in the art will recognize that compounds of Formula (I)-B may possess certain substituents that can be further derivatized to afford additional compounds within the scope of the instant invention. For example, when substituent $R_2$ is chloro, the corresponding phenylchloride or heteroarylchloride may be converted using conventional chemistry, such as zinc metal in the presence of zinc cyanide, a transition metal catalyst, and suitable ligands, to afford compounds of Formula (I) wherein $R_2$ is cyano. Alternatively, the phenylchloride or heteroarylchloride may undergo a Buchwald-Hartwig amination reaction in the presence of a suitable amine to afford an aryl- or heteroaryl-dialkylamine, wherein $R_2$ is di($C_{1-4}$alkyl)amino, of the present invention.

SPECIFIC EXAMPLES

Example 1

5-(4-chlorophenyl)-1-(2-methoxyphenyl)-3-((2,2,6,6-tetramethyltetrahydro-2H-pyran-4-yl)oxy)-1H-pyrazole (Cpd 23)

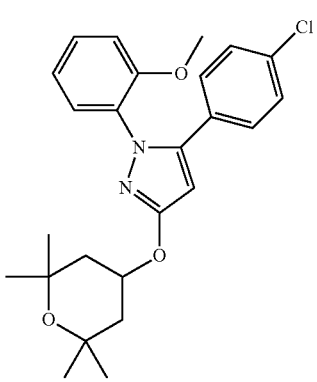 [SMILES: COc1ccccc1-n1nc(OC2CC(C)(C)OC(C)(C)C2)cc1-c1ccc(Cl)cc1]

a) N'-(2-methoxyphenyl)acetohydrazide, 1a

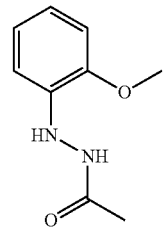

To a solution of (2-methoxyphenyl)hydrazine (7.40 g, 53.56 mmol) in 54 mL of toluene at RT was slowly added acetic anhydride (5.57 mL, 58.91 mmol) and the mixture left to stand at RT for 1 hr. The precipitate that formed was collected by filtration and washed with toluene to give 7.78 g (80%) of an off-white solid as compound 1a. $^1$H NMR (CHLOROFORM-d) δ: 7.48 (br. s., 1H), 6.77-6.99 (m, 4H), 6.33 (br. s., 1H), 3.89 and 3.88 (rotational isomers, s, 3H), 2.05 and 2.15 (rotational isomers, s, 3H).

b) 5-(4-chlorophenyl)-1-(2-methoxyphenyl)-1H-pyrazol-3(2H)-one, 1b

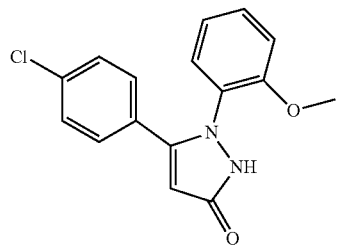 [SMILES: COc1ccccc1-n1[nH]c(=O)cc1-c1ccc(Cl)cc1]

To a mixture of compound 1a (2.90 g, 16.09 mmol) and ethyl 3-(4-chlorophenyl)-3-oxopropanoate (3.65 g, 16.09 mmol) in 10 mL of DCE was added dropwise phosphorus trichloride (1.41 mL, 16.09 mmol). The mixture was heated to 50° C. and all solids dissolved. After 2 hrs at 50° C. the mixture was cooled to RT and the precipitate was collected by filtration. The precipitate was partitioned between water and EtOAc and the organic phase was dried over sodium sulfate, filtered, and concentrated to give 2.50 g (49%) of compound 1b as a white solid. $^1$H NMR (DMSO-$d_6$) δ: 7.29-7.42 (m, 4H), 7.15 (d, J=8.3 Hz, 2H), 6.95-7.09 (m, 2H), 5.93 (s, 1H), 3.44 (s, 3H). Mass spectrum (ESI, m/z): Calcd. for $C_{16}H_{13}ClN_2O_2$, 301.1 (M+H), found 301.2.

c) 2,2,6,6-tetramethyltetrahydro-2H-pyran-4-ol, 1c

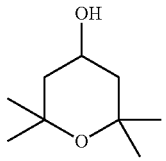

To a solution of 2,2,6,6-tetramethyldihydro-2H-pyran-4 (3H)-one (prepared according to PCT Int. Appl., WO2010021680) (2.30 g, 14.72 mmol) in 14 mL of THF and 5 mL of ethanol was added sodium borohydride (0.56 g, 14.72 mmol) and the mixture stirred at RT for 8 hrs. The mixture was diluted with 50 mL of EtOAc and washed with 50 mL of 0.2 N HCl and 50 mL of brine. The aqueous layer was again extracted with EtOAc (3×50 mL) and the organic fractions combined, dried over sodium sulfate and concentrated to give 2.30 g (99%) of compound 1c as a white solid that was used without further purification. $^1$H NMR (CHLOROFORM-d) δ: 4.13 (tt, J=11.4, 4.3 Hz, 1H), 1.94 (dd, J=12.5, 4.2 Hz, 2H), 1.28 (s, 6H), 1.27-1.22 (m, 8H).

d) 2,2,6,6-tetramethyltetrahydro-2H-pyran-4-yl methanesulfonate, 1d

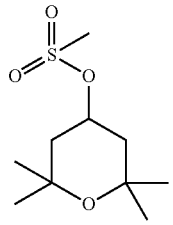

To a mixture of compound 1c (1.44 g, 9.10 mmol) and pyridine (1.90 mL, 13.65 mmol) in 23 mL of DCM at 0° C. was added methanesulfonyl chloride (0.78 mL, 10.01 mmol) and the mixture was allowed to stir for 1 hr at RT. The mixture was diluted with 40 mL of DCM, washed with 40 mL of NaHCO$_3$ and 40 mL of brine, dried over sodium sulfate and concentrated to give 2.10 g (97%) of compound 1d as a white solid that was used without further purification. $^1$H NMR (CHLOROFORM-d) δ: 5.05 (tt, J=11.4, 4.4 Hz, 1H), 2.96 (s, 3H), 2.02 (dd, J=12.6, 4.5 Hz, 2H), 1.50 (t, J=11.9 Hz, 2H), 1.23 (s, 6H), 1.20 (s, 6H).

e) 5-(4-chlorophenyl)-1-(2-methoxyphenyl)-3-((2,2,6,6-tetramethyltetrahydro-2H-pyran-4-yl)oxy)-1H-pyrazole, Cpd 23

A flask was charged with compound 1b (0.70 g, 2.14 mmol), compound 1d (0.61 g, 2.57 mmol), cesium carbonate (1.39 g, 4.28 mmol) and toluene (7 mL) and heated at 115° C. for 12 h. The reaction was diluted with EtOAc (50 mL) and washed with saturated aqueous NaHCO$_3$ (2×50 mL) and brine (100 mL), and the organic layer dried over Na$_2$SO$_4$ and evaporated. The crude product was purified by silica gel chromatography (Thomson Scientific 25-g cartridge, 4-40% EtOAc/heptane in 10 column volumes) to give 0.48 g (51%) of compound 23 as a white solid. $^1$H NMR (CHLOROFORM-d) δ: 7.44 (dd, J=7.7, 1.6 Hz, 1H), 7.34 (td, J=7.9, 1.7 Hz, 1H), 7.20-7.25 (m, 2H), 7.11-7.16 (m, 2H), 7.04 (td, J=7.7, 1.2 Hz, 1H), 6.86 (dd, J=8.3, 1.0 Hz, 1H), 5.95 (s, 1H), 5.06 (tt, J=10.9, 4.2 Hz, 1H), 3.46 (s, 3H), 2.22 (dd, J=12.7, 4.4 Hz, 2H), 1.54 (t, J=11.7 Hz, 2H), 1.34 (s, 6H), 1.31 (s, 6H). Mass spectrum (ESI, m/z): Calcd. for $C_{25}H_{29}ClN_2O_3$, 441.2 (M+H), found 441.1.

Example 2

5-(4-Chlorophenyl)-1-(2-methoxyphenyl)-3-[(2,2,6,6-tetramethyltetrahydro-2H-thiopyran-4-yl)oxy]-1H-pyrazole (Cpd 36)

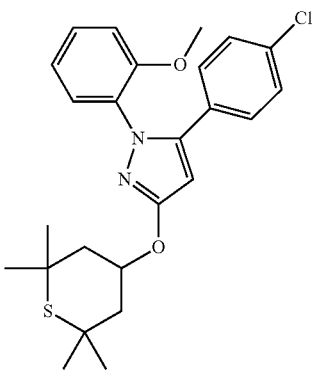 [SMILES: COc1ccccc1-n1nc(OC2CC(C)(C)SC(C)(C)C2)cc1-c1ccc(Cl)cc1]

Compound 36 was prepared according to the procedure described in Example 1, substituting 2,2,6,6-tetramethyldihydro-2H-thiopyran-4(3H)-one (prepared according to US patent 20090105296) for 2,2,6,6-tetramethyldihydro-2H-pyran-4(3H)-one in step (c). $^1$H NMR (CHLOROFORM-d) δ: 7.43 (dd, J=7.7, 1.3 Hz, 1H), 7.31-7.37 (m, 1H), 7.19-7.26 (m, 2H), 7.11-7.16 (m, 2H), 7.04 (t, J=7.6 Hz, 1H), 6.86 (d, J=8.3 Hz, 1H), 5.95 (s, 1H), 5.02 (tt, J=11.2, 3.3 Hz, 1H), 3.45 (s, 3H), 2.37 (dd, J=12.6, 3.3 Hz, 2H), 1.72 (t, J=11.9 Hz, 2H), 1.54 (s, 6H), 1.35 (s, 6H). Mass spectrum (ESI, m/z): Calcd. for $C_{25}H_{29}ClN_2O_2S$, 457.2 (M+H), found 457.2.

Example 3

5-(4-Chlorophenyl)-1-(2-methoxyphenyl)-3-[(2,2,6,6-tetramethyl-1,1-dioxidotetrahydro-2H-thiopyran-4-yl)oxy]-1H-pyrazole (Cpd 37)

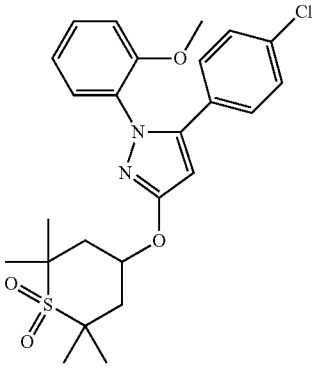 [SMILES: COc1ccccc1-n1nc(OC2CC(C)(C)S(=O)(=O)C(C)(C)C2)cc1-c1ccc(Cl)cc1]

To a solution of compound 36 (50 mg, 0.11 mmol) in 0.5 mL of DCM was added mCPBA (77%, 47 mg, 0.21 mmol) and the mixture was stirred at RT for 1 hr. The solution was concentrated and purified by RP-HPLC on a C18 column eluting with a linear gradient of 40-60% CH$_3$CN in 0.1% TFA over 15 min to give after lyophilization 38 mg (74%) of compound 37 as a white solid. $^1$H NMR (CHLOROFORM-d) δ: 7.32-7.41 (m, 2H), 7.22 (d, J=8.6 Hz, 2H), 7.08-7.14 (m, 2H), 7.03 (t, J=7.4 Hz, 1H), 6.86 (d, J=8.2 Hz, 1H), 5.93 (s, 1H), 5.06-5.16 (m, 1H), 3.47 (s, 3H), 2.24-2.41 (m, 4H), 1.58 (s, 6H), 1.50 (s, 6H). Mass spectrum (ESI, m/z): Calcd. for C$_{25}$H$_{29}$ClN$_2$O$_4$S, 489.1 (M+H), found 489.1

Example 4

(1r,4r)-4-((5-(4-chlorophenyl)-1-(2-methoxyphenyl)-1H-pyrazol-3-yl)oxy)-2,2,6,6-tetramethyltetrahydro-2H-thiopyran 1-oxide trifluoroacetate (Cpd 38)

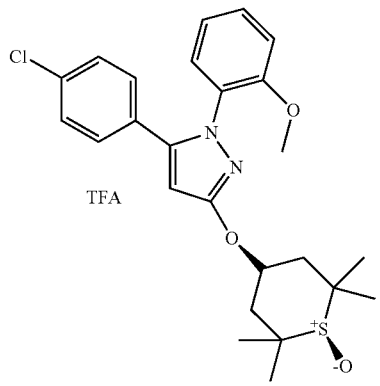

and (1s,4s)-4-((5-(4-chlorophenyl)-1-(2-methoxyphenyl)-1H-pyrazol-3-yl)oxy)-2,2,6,6-tetramethyltetrahydro-2H-thiopyran 1-oxide trifluoroacetate (Cpd 39)

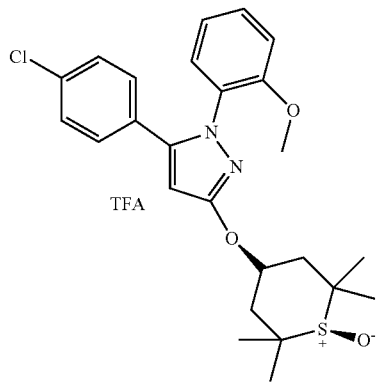

Compounds 38 and 39 were prepared according to the procedure described in Example 3, using 1.5 eq of mCPBA, and were purified by RP-HPLC on a C18 column eluting with a linear gradient of 40-60% CH$_3$CN in 0.1% TFA over 15 min. The first compound to elute was arbitrarily assigned as compound 38 (cis) and the second as compound 39 (trans).

Cpd 38: $^1$H NMR (CHLOROFORM-d) δ: 7.39 (dd, J=7.8, 1.6 Hz, 1H), 7.31-7.37 (m, 1H), 7.19-7.23 (m, 2H), 7.08-7.13 (m, 2H), 7.02 (td, J=7.6, 1.2 Hz, 1H), 6.85 (dd, J=8.2, 1.2 Hz, 1H), 5.93 (s, 1H), 4.86-5.03 (m, 1H), 3.45 (s, 3H), 2.08-2.14 (m, 4H), 1.43 (s, 6H), 1.42 (s, 6H). Mass spectrum (ESI, m/z): Calcd. for C$_{25}$H$_{29}$ClN$_2$O$_3$S, 473.2 (M+H), found 473.2.

Cpd 39: $^1$H NMR (CHLOROFORM-d) δ: 7.39 (dd, J=7.6, 1.8 Hz, 1H), 7.32-7.37 (m, 1H), 7.19-7.23 (m, 2H), 7.08-7.13 (m, 2H), 7.01-7.06 (m, 1H), 6.86 (dd, J=8.2, 1.2 Hz, 1H), 5.91 (s, 1H), 4.91-4.99 (m, 1H), 3.46 (s, 3H), 3.43 (dt, J=3.1, 1.6 Hz, 1H), 2.40 (dd, J=14.5, 3.5 Hz, 4H), 1.43 (s, 6H), 1.34 (s, 6H). Mass spectrum (ESI, m/z): Calcd. for C$_{25}$H$_{29}$ClN$_2$O$_3$S, 473.2 (M+H), found 473.2.

Example 5

4-{1-(2-Methoxyphenyl)-3-[(2,2,6,6-tetramethyltetrahydro-2H-thiopyran-4-yl)oxy]-1H-pyrazol-5-yl}benzonitrile (Cpd 44)

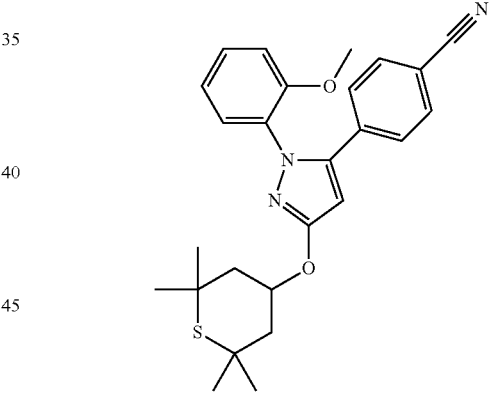

A microwave vial was charged with compound 36 (90.0 mg, 0.20 mmol), zinc cyanide (35.0 mg, 0.30 mmol), zinc (3.8 mg, 0.06 mmol), Pd(t-Bu$_3$)$_2$ (10.1 mg, 0.020 mmol), and 0.8 mL of N,N-dimethylacetamide and heated to 170° C. for 1 hr. The mixture was loaded directly on to a 12-g silica gel cartridge (Thomson Scientific) and eluted with a linear gradient of 3-40% EtOAc/heptane in 10 column volumes to give 76 mg (86%) of compound 44 as a white solid. $^1$H NMR (CHLOROFORM-d) δ: 7.53 (d, J=8.6 Hz, 2H), 7.45 (dd, J=7.8, 1.7 Hz, 1H), 7.35 (td, J=7.9, 1.7 Hz, 1H), 7.28 (d, J=8.6 Hz, 2H), 7.01-7.10 (m, 1H), 6.84 (d, J=7.6 Hz, 1H), 6.00 (s, 1H), 5.01 (tt, J=11.2, 3.3 Hz, 1H), 3.40 (s, 3H), 2.35 (dd, J=12.8, 3.3 Hz, 2H), 1.70 (t, J=11.9 Hz, 2H), 1.55 (s, 6H), 1.52 (s, 6H). Mass spectrum (ESI, m/z): Calcd. for C$_{26}$H$_{29}$N$_3$O$_2$S, 448.2 (M+H), found 448.2.

Example 6

4-(1-(2-methoxyphenyl)-3-((1r,4r)-2,2,6,6-tetramethyl-1-oxidotetrahydro-2H-thiopyran-4-yl)oxy)-1H-pyrazol-5-yl)benzonitrile (Cpd 46)

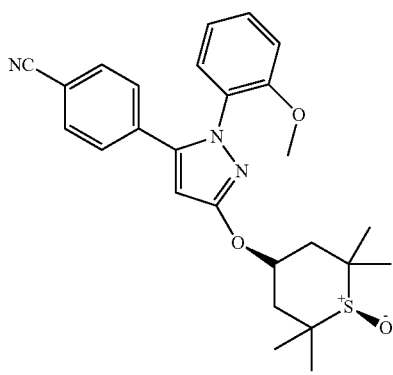

Compound 46 was prepared from compound 44 according to the procedure described in Example 4. The compound is pure but of unknown configuration and was arbitrarily assigned as cis. $^1$H NMR (CHLOROFORM-d) δ: 7.53 (d, J=8.6 Hz, 2H), 7.45 (dd, J=7.7, 1.6 Hz, 1H), 7.36 (td, J=7.9, 1.7 Hz, 1H), 7.26-7.30 (m, 2H), 7.06 (td, J=7.6, 1.1 Hz, 1H), 6.84 (d, J=7.8 Hz, 1H), 6.00 (s, 1H), 4.96 (tt, J=11.1, 3.9 Hz, 1H), 3.40 (s, 3H), 2.09-2.17 (m, 2H), 2.01-2.07 (m, 2H), 1.40 (s, 6H), 1.38 (s, 6H). Mass spectrum (ESI, m/z): Calcd. for $C_{26}H_{29}N_3O_3S$, 464.2 (M+H), found 464.2.

Example 7

4-{1-(2-Methoxyphenyl)-3-[(2,2,6,6-tetramethyl-1,1-dioxidotetrahydro-2H-thiopyran-4-yl)oxy]-1H-pyrazol-5-yl}benzonitrile (Cpd 45)

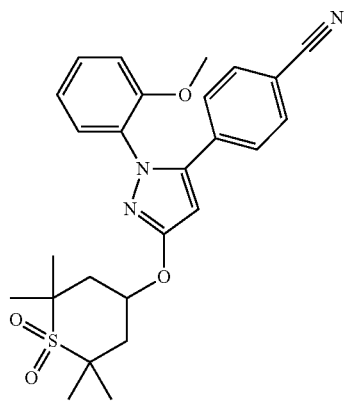 [SMILES: COc1ccccc1-n1nc(OC2CC(C)(C)S(=O)(=O)C(C)(C)C2)cc1-c1ccc(C#N)cc1]

Compound 45 was prepared from compound 44 according to the procedure described in Example 3. $^1$H NMR (CHLOROFORM-d) δ: 7.53 (d, J=8.3 Hz, 2H), 7.44 (dd, J=7.7, 1.6 Hz, 1H), 7.33-7.40 (m, 1H), 7.28 (d, J=8.3 Hz, 2H), 7.07 (t, J=7.7 Hz, 1H), 6.85 (d, J=8.3 Hz, 1H), 6.00 (s, 1H), 5.15 (tt, J=10.2, 3.7 Hz, 1H), 3.41 (s, 3H), 2.34-2.41 (m, 2H), 2.22-2.32 (m, 2H), 1.59 (s, 6H), 1.50 (s, 6H). Mass spectrum (ESI, m/z): Calcd. for $C_{26}H_{29}N_3O_4S$, 480.1 (M+H), found 480.1.

Example 8

4-{1-(2-Methoxyphenyl)-3-[(2,2,6,6-tetramethyltetrahydro-2H-pyran-4-yl)oxy]-1H-pyrazol-5-yl}benzonitrile (Cpd 43)

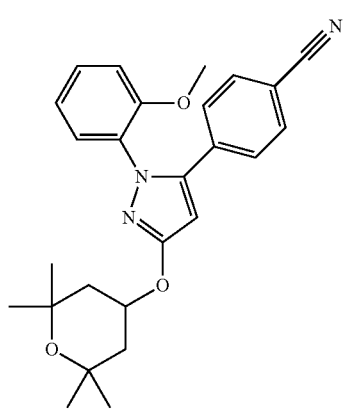

Compound 43 was prepared from compound 23 according to the procedure described in Example 5. $^1$H NMR (CHLOROFORM-d) δ: 7.53 (d, J=8.6 Hz, 2H), 7.46 (d, J=6.3 Hz, 1H), 7.35 (br. s., 1H), 7.25-7.31 (m, 2H), 7.06 (t, J=7.2 Hz, 1H), 6.84 (d, J=7.8 Hz, 1H), 6.01 (s, 1H), 5.00-5.12 (m, 1H), 3.40 (s, 3H), 2.20 (dd, J=12.1, 2.7 Hz, 2H), 1.51 (t, J=11.5 Hz, 2H), 1.32 (s, 6H), 1.29 (s, 6H). Mass spectrum (ESI, m/z): Calcd. for $C_{26}H_{29}N_3O_3$, 432.2 (M+H), found 432.2.

Example 9

1-(2-Methoxyphenyl)-5-(4-methoxyphenyl)-3-[(2,2,6,6-tetramethyltetrahydro-2H-thiopyran-4-yl)oxy]-1H-pyrazole (Cpd 32)

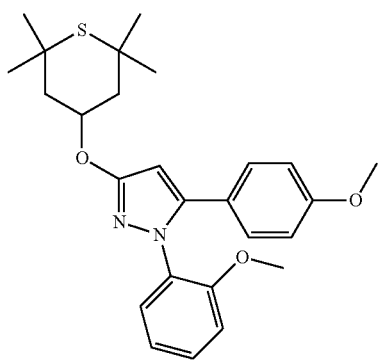

a) 1-(2-Methoxyphenyl)-5-(4-methoxyphenyl)-1H-pyrazol-3(2H)-one, 9a

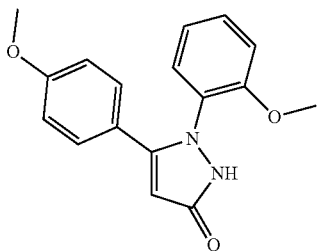 [SMILES: COc1ccc(-c2cc(=O)[nH]n2-c2ccccc2OC)cc1]

Compound 9a was prepared according to the procedure described in Example 1, step (b), substituting ethyl 3-(4-methoxyphenyl)-3-oxopropanoate. $^1$H NMR (DMSO-$d_6$) δ: 7.35-7.43 (m, 1H), 7.29 (dd, J=7.7, 1.6 Hz, 1H), 7.05-7.11 (m, 3H), 7.00 (td, J=7.6, 1.0 Hz, 1H), 6.79-6.84 (m, 2H), 5.85 (s, 1H), 3.70 (s, 3H), 3.49 (s, 3H).

b) 1-(2-Methoxyphenyl)-5-(4-methoxyphenyl)-3-[(2,2,6,6-tetramethyltetrahydro-2H-thiopyran-4-yl)oxy]-1H-pyrazole, Cpd 32

Compound 32 was prepared according to Example 1, substituting 2,2,6,6-tetramethyldihydro-2H-thiopyran-4(3H)-one (prepared according to US patent 20090105296) for 2,2,6,6-tetramethyldihydro-2H-pyran-4(3H)-one in step (c); and substituting compound 9a for compound 1b in step (e). $^1$H NMR (CHLOROFORM-d) γ: 7.35-7.46 (m, 1H), 7.28-7.34 (m, 1H), 7.11 (d, J=8.6 Hz, 2H), 7.00 (t, J=7.6 Hz, 1H), 6.85 (d, J=8.3 Hz, 1H), 6.76 (d, J=8.8 Hz, 2H), 5.88 (s, 1H), 4.92-5.02 (m, 1H), 3.77 (s, 3H), 3.46 (s, 3H), 2.36 (dd, J=12.7, 3.2 Hz, 2H), 1.70 (t, J=11.9 Hz, 2H), 1.57 (s, 6H), 1.52 (s, 6H). Mass spectrum (ESI, m/z): Calcd. for $C_{26}H_{32}N_2O_3S$, 453.2 (M+H), found 453.3.

Example 10

1-(2-Methoxyphenyl)-5-(4-methoxyphenyl)-3-[(2,2,6,6-tetramethyl-1,1-dioxidotetrahydro-2H-thiopyran-4-yl)oxy]-1H-pyrazole (Cpd 33)

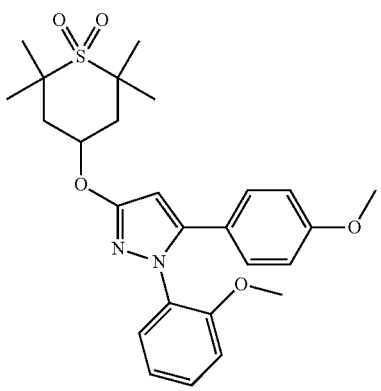

Compound 33 was prepared from compound 32 according to the procedure described in Example 3. $^1$H NMR (CHLOROFORM-d) δ: 7.30-7.39 (m, 2H), 7.10 (d, J=8.8 Hz, 2H), 7.00 (t, J=7.7 Hz, 1H), 6.88 (d, J=8.6 Hz, 1H), 6.76 (d, J=8.8 Hz, 2H), 5.89 (s, 1H), 5.02-5.12 (m, 1H), 3.77 (s, 3H), 3.50 (s, 3H), 2.23-2.43 (m, 4H), 1.58 (s, 6H), 1.50 (s, 6H). Mass spectrum (ESI, m/z): Calcd. for $C_{26}H_{32}N_2O_5S$, 485.2 (M+H), found 485.2.

Example 11

(1r,4r)-4-((1-(2-methoxyphenyl)-5-(4-methoxyphenyl)-1H-pyrazol-3-yl)oxy)-2,2,6,6-tetramethyltetrahydro-2H-thiopyran 1-oxide (Cpd 34)

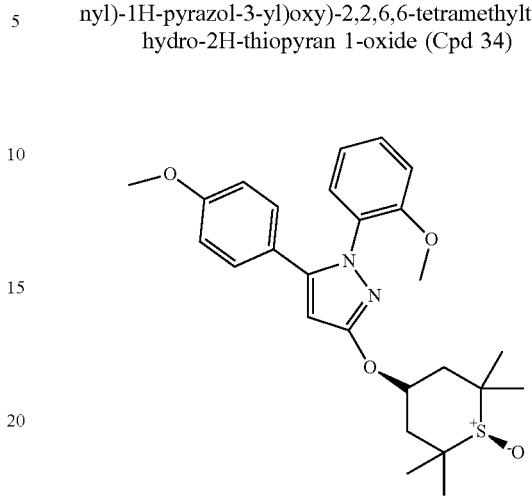

and (1s,4s)-4-((1-(2-methoxyphenyl)-5-(4-methoxyphenyl)-1H-pyrazol-3-yl)oxy)-2,2,6,6-tetramethyltetrahydro-2H-thiopyran 1-oxide (Cpd 35)

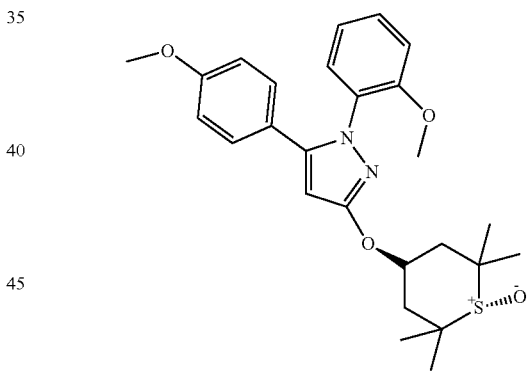

Compounds 34 and 35 were prepared from compound 32 according to the procedure described in Example 4. The first compound to elute was arbitrarily assigned as 34 (cis) and the second as 35 (trans).

Cpd 34: $^1$H NMR (MeOD) δ: 7.42 (td, J=7.9, 1.7 Hz, 1H), 7.35 (dd, J=7.9, 1.6 Hz, 1H), 7.10-7.18 (m, 2H), 7.01-7.08 (m, 2H), 6.81 (d, J=8.8 Hz, 2H), 6.00 (s, 1H), 3.76 (s, 3H), 3.56 (s, 3H), 2.40 (dd, J=14.5, 3.3 Hz, 2H), 1.84-1.93 (m, 2H), 1.45 (s, 6H), 1.37 (s, 6H). Mass spectrum (ESI, m/z): Calcd. for $C_{26}H_{32}N_2O_4S$, 469.2 (M+H), found 469.2.

Cpd 35: $^1$H NMR (CHLOROFORM-d) δ: 7.38 (dd, J=7.7, 1.6 Hz, 1H), 7.30-7.35 (m, 1H), 7.10 (d, J=9.0 Hz, 2H), 7.00 (d, J=3.2 Hz, 1H), 6.86 (s, 1H), 6.72-6.78 (m, 2H), 5.88 (s, 1H), 4.90-4.98 (m, 1H), 3.76 (s, 3H), 3.46 (s, 3H), 2.01-2.18 (m, 4H), 1.41 (s, 6H), 1.38 (s, 6H). Mass spectrum (ESI, m/z): Calcd. for $C_{26}H_{32}N_2O_4S$, 469.2 (M+H), found 469.2.

Example 12

1-(2-Methoxyphenyl)-5-(4-methoxyphenyl)-3-[(2,2,6,6-tetramethyltetrahydro-2H-pyran-4-yl)oxy]-1H-pyrazole (Cpd 31)

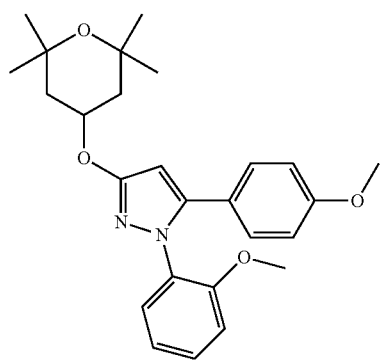

Compound 31 was prepared according to the procedure described in Example 1, step (e), substituting compound 9a for compound 1b. $^1$H NMR (CHLOROFORM-d) d: 7.39 (dd, J=7.8, 1.8 Hz, 1H), 7.35 (td, J=7.9, 1.6 Hz, 1H), 7.11-7.17 (m, 2H), 7.01 (td, J=7.6, 1.1 Hz, 1H), 6.88 (dd, J=8.3, 1.0 Hz, 1H), 6.76-6.81 (m, 2H), 5.93 (s, 1H), 5.00 (tt, J=10.9, 4.4 Hz, 1H), 3.78 (s, 3H), 3.53 (s, 3H), 2.22 (dd, J=12.9, 4.3 Hz, 2H), 1.56 (t, J=11.7 Hz, 2H), 1.34 (s, 6H), 1.31 (s, 6H); . Mass spectrum (ESI, m/z): Calcd. for $C_{26}H_{32}N_2O_4$, 437.2 (M+H), found 437.1.

Example 13

5-(4-Chlorophenyl)-1-(2-methoxyphenyl)-3-(tetrahydro-2H-pyran-4-yloxy)-1H-pyrazole (Cpd 6)

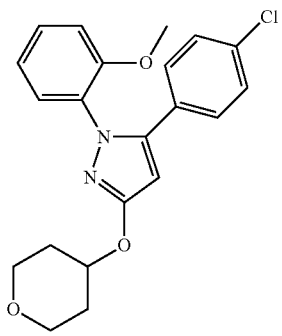 [SMILES: COc1ccccc1-n1nc(OC2CCOCC2)cc1-c1ccc(Cl)cc1]

Compound 6 was prepared according to the procedure in Example 1, substituting commercially available tetrahydro-4H-pyran-4-ol for compound 1c. $^1$H NMR (CHLOROFORM-d) δ: 7.39 (dd, J=7.7, 1.6 Hz, 1H), 7.28-7.35 (m, 1H), 7.16-7.23 (m, 2H), 7.06-7.15 (m, 2H), 7.01 (td, J=7.6, 1.3 Hz, 1H), 6.84 (dd, J=8.3, 1.0 Hz, 1H), 5.95 (s, 1H), 4.85 (tt, J=8.2, 4.0 Hz, 1H), 3.92-4.05 (m, 2H), 3.58 (ddd, J=11.7, 8.8, 3.0 Hz, 2H), 3.45 (s, 3H), 2.07-2.18 (m, 2H), 1.78-1.95 (m, 2H). Mass spectrum (ESI, m/z): Calcd. for $C_{21}H_{21}ClN_2O_3$, 385.1 (M+H), found 385.1

Example 14

5-(4-Chlorophenyl)-1-(2-methoxyphenyl)-3-(tetrahydro-2H-thiopyran-4-yloxy)-1H-pyrazole (Cpd 7)

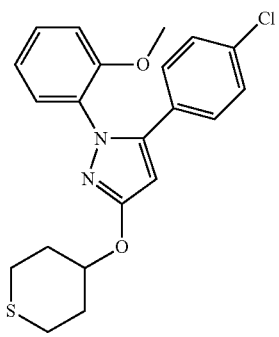 [SMILES: COc1ccccc1-n1nc(OC2CCSCC2)cc1-c1ccc(Cl)cc1]

Compound 7 was prepared according to Example 1, substituting commercially available tetrahydro-4H-thiopyran-4-ol for compound 1c. $^1$H NMR (CHLOROFORM-d) δ: 7.41 (dd, J=7.8, 1.8 Hz, 1H), 7.32-7.39 (m, 1H), 7.23 (d, J=8.6 Hz, 2H), 7.09-7.16 (m, 2H), 7.04 (td, J=7.6, 1.1 Hz, 1H), 6.88 (d, J=8.3 Hz, 1H), 5.97 (s, 1H), 5.01 (quin, J=4.7 Hz, 1H), 3.74-3.93 (m, 3H), 3.60-3.70 (m, 1H), 3.49 (s, 3H), 1.99-2.12 (m, 4H). Mass spectrum (ESI, m/z): Calcd. for $C_{21}H_{21}ClN_2O_2S$, 401.0 (M+H), found 401.0

Example 15

5-(4-Chlorophenyl)-3-[(1,1-dioxidotetrahydro-2H-thiopyran-4-yl)oxy]-1-(2-methoxyphenyl)-1H-pyrazole (Cpd 10)

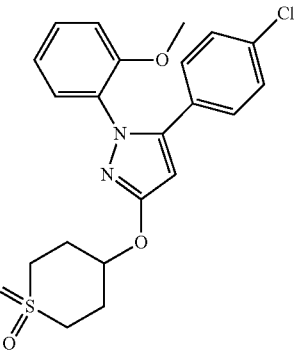

To a solution of compound 7 (40.0 mg, 0.10 mmol) in 2 mL of DCM at RT was added mCPBA (60 mg, 57-80%) and the mixture stirred for 1 hr. The reaction was diluted with EtOAc (50 mL) and washed with saturated aqueous NaHCO$_3$ (2×50 mL) and brine (100 mL), and the organic layer dried over Na$_2$SO$_4$, filtered, and evaporated. The crude product was purified by silica gel chromatography (Thomson Scientific 12-g cartridge, 5-50% EtOAc/heptane in 10 column volumes) to give 50 mg (43%) of compound 10 as a white solid. $^1$H NMR (CHLOROFORM-d) δ: 7.31-7.43 (m, 2H), 7.23 (d, J=8.6 Hz, 2H), 7.12 (d, J=8.6 Hz, 2H), 7.03 (t, J=7.6 Hz, 1H), 6.87 (d, J=8.1 Hz, 1H), 5.97 (s, 1H), 4.99-5.07 (m, 1H), 3.49 (s, 3H), 3.39-3.47 (m, 2H), 2.92-

3.02 (m, 2H), 2.64 (dd, J=14.0, 3.4 Hz, 2H), 2.23-2.46 (m, 2H). Mass spectrum (ESI, m/z): Calcd. for $C_{21}H_{21}ClN_2O_4S$, 433.0 (M+H), found 433.0.

Example 16 tert-Butyl 4-{[5-(4-chlorophenyl)-1-(2-methoxyphenyl)-1H-pyrazol-3-yl]oxy}piperidine-1-carboxylate (Cpd 41)

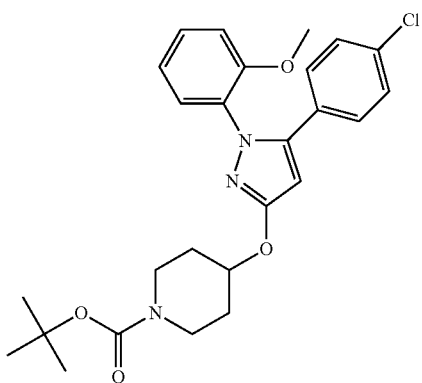 [SMILES: COc1ccccc1-n1nc(OC2CCN(C(=O)OC(C)(C)C)CC2)cc1-c1ccc(Cl)cc1]

Compound 41 was prepared according to the procedure described in Example 1, step (e), substituting 1-Boc-4-methanesulfonyloxypiperidine for compound 1d. $^1$H NMR (CHLOROFORM-d) δ: 7.40 (dd, J=7.7, 1.6 Hz, 1H), 7.29-7.35 (m, 1H), 7.16-7.23 (m, 2H), 7.06-7.14 (m, 2H), 7.01 (td, J=7.6, 1.1 Hz, 1H), 6.82-6.86 (m, 1H), 5.94 (s, 1H), 4.78-4.87 (m, 1H), 3.75 (br. s., 2H), 3.46 (s, 3H), 3.25-3.35 (m, 2H), 2.05 (s, 2H), 1.75-1.87 (m, 2H), 1.47 (s, 9H). Mass spectrum (ESI, m/z): Calcd. for $C_{26}H_{30}ClN_3O_4$, 483.2 (M+H), found 483.9.

Example 17

1-Acetyl-4-{[5-(4-chlorophenyl)-1-(2-methoxyphenyl)-1H-pyrazol-3-yl]oxy}piperidine (Cpd 3)

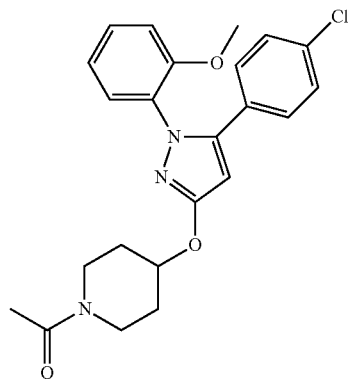 [SMILES: COc1ccccc1-n1nc(OC2CCN(C(C)=O)CC2)cc1-c1ccc(Cl)cc1]

a) 4-((5-(4-chlorophenyl)-1-(2-methoxyphenyl)-1H-pyrazol-3-yl)oxy)piperidine trifluoroacetate, 17a

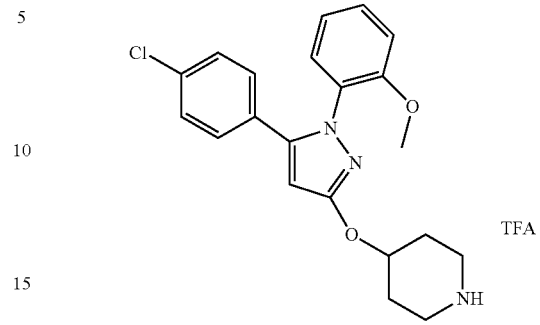

To a solution of compound 41 in 12 mL of DCM was added 4 mL of TFA and the mixture stirred at RT for 1 hr. The mixture was concentrated and the residue crystallized from methanol/water to give 380 mg (83%) of a white solid. $^1$H NMR (CHLOROFORM-d) d: 8.14 (br. s., 1H), 7.86 (br. s., 1H), 7.44-7.52 (m, 1H), 7.25-7.33 (m, 3H), 7.16 (d, J=8.6 Hz, 2H), 6.93-7.04 (m, 2H), 6.19 (s, 1H), 4.91 (br. s., 1H), 3.64 (s, 3H), 3.34-3.58 (m, 4H), 2.22-2.38 (m, 4H). Mass spectrum (ESI, m/z): Calcd. for $C_{21}H_{22}ClN_3O_2$, 384.1 (M+H), 384.0.

b) 1-Acetyl-4-{[5-(4-chlorophenyl)-1-(2-methoxyphenyl)-1H-pyrazol-3-yl]oxy}piperidine, Cpd 3

To a solution of compound 17a (30 mg, 0.06 mmol) and NEt$_3$ (0.025 mL, 0.18 mmol) in 0.25 mL of DCM at RT was added acetyl chloride (0.009 mL) and the mixture stirred for 8 hr. The mixture was concentrated and the residue purified by RP-HPLC (C18), eluting with a linear gradient of 40-100% CH$_3$CN in 0.1% TFA/H$_2$O over 18 min to give 20 mg of compound 3 as a white solid. $^1$H NMR (CHLOROFORM-d) δ: 7.38 (dd, J=7.7, 1.6 Hz, 1H), 7.33 (td, J=7.9, 1.6 Hz, 1H), 7.19-7.23 (m, 2H), 7.07-7.13 (m, 2H), 7.01 (td, J=7.6, 1.3 Hz, 1H), 6.83-6.89 (m, 1H), 5.95 (s, 1H), 4.91 (tt, J=6.6, 3.5 Hz, 1H), 3.61-3.87 (m, 3H), 3.39-3.50 (m, 4H), 2.16 (s, 3H), 1.85-2.09 (m, 4H). Mass spectrum (ESI, m/z): Calcd. for $C_{23}H_{24}ClN_3O_3$, 426.1 (M+H), 426.1.

Example 18

4-{[5-(4-Chlorophenyl)-1-(2-methoxyphenyl)-1H-pyrazol-3-yl]oxy}-N,N-dimethylpiperidine-1-carboxamide (Cpd 4)

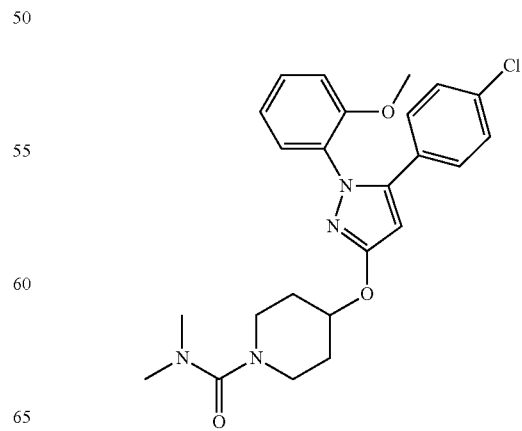

To a solution of compound 17a (30 mg, 0.06 mmol) and NEt₃ (0.025 mL, 0.18 mmol) in 0.25 mL of DCM at RT was added N,N-dimethylcarbamoyl chloride (0.008 mL, 0.09 mmol) and the mixture was stirred for 8 hr. The mixture was concentrated and the residue purified by RP-HPLC (C18), eluting with a linear gradient of 40-100% CH₃CN in 0.1% TFA/H₂O over 18 min to give 18 mg of compound 4 as a white solid. $^1$H NMR (MeOH) δ: 7.40-7.46 (m, 1H), 7.38 (dd, J=7.8, 1.5 Hz, 1H), 7.25-7.29 (m, 2H), 7.18-7.23 (m, 2H), 7.02-7.09 (m, 2H), 6.12 (s, 1H), 4.68-4.75 (m, 1H), 3.59-3.52 (m, 3H), 3.13-3.22 (m, 2H), 2.87 (s, 6H), 2.01-2.14 (m, 2H), 1.73-1.93 (m, J=12.8, 8.4, 4.1, 4.1 Hz, 2H). Mass spectrum (ESI, m/z): Calcd. for $C_{24}H_{27}ClN_4O_3$, 455.2 (M+H), found 455.0.

Example 19

4-{[5-(4-Chlorophenyl)-1-(2-methoxyphenyl)-1H-pyrazol-3-yl]oxy}-1-(methylsulfonyl)piperidine (Cpd 5)

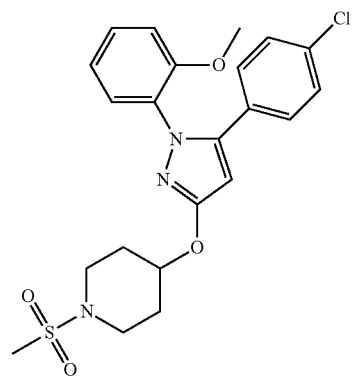 [SMILES: COc1ccccc1-n1nc(OC2CCN(S(C)(=O)=O)CC2)cc1-c1ccc(Cl)cc1]

To a solution of compound 17a (30 mg, 0.06 mmol) and NEt₃ (0.025 mL, 0.18 mmol) in 0.25 mL of DCM at RT was added methanesulfonyl chloride (0.006 mL, 0.08 mmol) and the mixture was stirred for 8 hrs. The mixture was concentrated and the residue purified by RP-HPLC (C18), eluting with a linear gradient of 40-100% CH₃CN in 0.1% TFA/H₂O over 18 min to give 17 mg of compound 5 (50%) as a white solid. $^1$H NMR (CHLOROFORM-d) δ: 7.29-7.41 (m, 2H), 7.19-7.24 (m, 2H), 7.06-7.14 (m, 2H), 7.01 (td, J=7.6, 1.1 Hz, 1H), 6.86 (d, J=8.3 Hz, 1H), 5.96 (s, 1H), 4.83 (quin, J=4.5 Hz, 1H), 3.49 (s, 3H), 3.26-3.45 (m, 4H), 2.80 (s, 3H), 2.03-2.15 (m, 4H). Mass spectrum (ESI, m/z): Calcd. for $C_{22}H_{24}ClN_3O_4S$, 462.1 (M+H), found 462.1.

Example 20

4-{[5-(4-Chlorophenyl)-1-(2-methoxyphenyl)-1H-pyrazol-3-yl]oxy}-1-(2,2,2-trifluoroethyl)piperidine (Cpd 8)

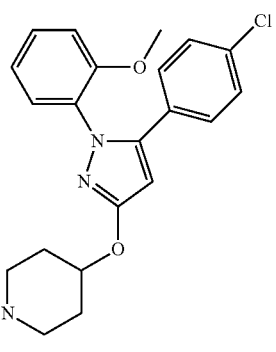

To a solution of compound 17a (100 mg, 0.07 mmol) and NEt₃ (0.030 mL, 0.21 mmol) in 0.5 mL of DCE was added 2,2,2-trifluoroethyl trifluoromethanesulfonate (16 mg, 0.07 mmol) and the mixture was heated at 80° C. for 8 hrs. The mixture was concentrated and the residue purified by RP-HPLC (C18), eluting with a linear gradient of 40-100% CH₃CN in 0.1% TFA/H₂O over 18 min to give 12 mg of compound 8 (38%) as a white solid. $^1$H NMR (MeOH) δ: 7.32 (t, J=7.8 Hz, 1H), 7.24-7.28 (m, 1H), 7.14-7.18 (m, 2H), 7.05-7.11 (m, 2H), 6.91-6.97 (m, 2H), 6.02 (s, 1H), 4.60-4.68 (m, 1H), 3.74 (q, J=9.3 Hz, 2H), 3.42 (s, 3H), 3.25-3.35 (m, 2H), 3.05-3.14 (m, 2H), 1.97-2.17 (m, 4H). Mass spectrum (ESI, m/z): Calcd. for $C_{23}H_{23}ClF_3N_3O_2$, 466.1 (M+H), found 466.0.

Example 21

4-{[5-(4-Chlorophenyl)-1-(2-methoxyphenyl)-1H-pyrazol-3-yl]oxy}-1-(trifluoroacetyl)piperidine (Cpd 9)

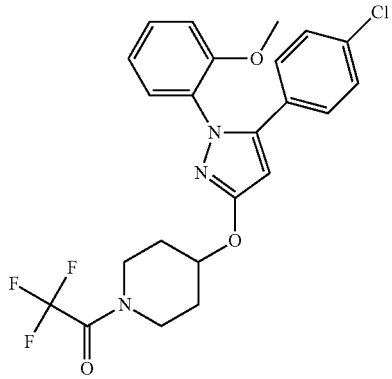 [SMILES: COc1ccccc1-n1nc(OC2CCN(C(=O)C(F)(F)F)CC2)cc1-c1ccc(Cl)cc1]

To a solution of compound 17a (100 mg, 0.20 mmol) and NEt₃ (0.100 mL, 0.72 mmol) in 1 mL of DCM was added trifluoroacetic anhydride (0.035 mL, 0.25 mmol) and the mixture was stirred for 1 hr at RT. The mixture was loaded directly on to a 12-g silica gel cartridge (Thomson Scientific) and eluted with 3-30% EtOAc/heptane in 10 column volumes to give 65 mg (67%) of compound 9 as a white solid. $^1$H NMR (CHLOROFORM-d) δ: 7.41 (dd, J=7.8, 1.8 Hz, 1H), 7.32-7.39 (m, 1H), 7.23 (d, J=8.6 Hz, 2H), 7.09-7.16 (m, 2H), 7.04 (td, J=7.6, 1.1 Hz, 1H), 6.88 (d, J=8.3 Hz, 1H), 5.97 (s, 1H), 5.01 (quin, J=4.7 Hz, 1H), 3.74-3.93 (m, 3H), 3.60-3.70 (m, 1H), 3.49 (s, 3H), 1.99-2.12 (m, 4H). Mass spectrum (ESI, m/z): Calcd. for $C_{23}H_{21}ClF_3N_3O_3$, 480.1 (M+H), found 480.1.

Example 22

4-{[5-(4-Chlorophenyl)-1-(2-methoxyphenyl)-1H-pyrazol-3-yl]oxy}-1-[(trifluoromethyl)sulfonyl]piperidine (Cpd 14)

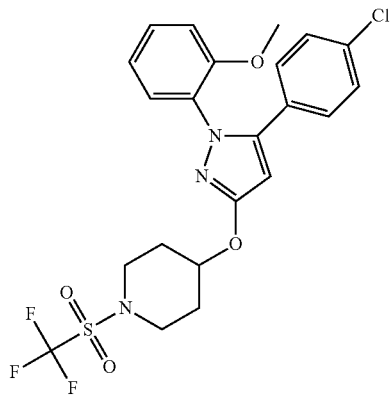 [SMILES: COc1ccccc1-n1nc(OC2CCN(S(=O)(=O)C(F)(F)F)CC2)cc1-c1ccc(Cl)cc1]

To a solution of compound 17a (250 mg, 0.50 mmol) and NEt$_3$ (0.21 mL, 1.51 mmol) in 5 mL of DCE was added N-phenyl-bis-(trifluoromethanesulfonimide) (0.20 g, 0.56 mmol) and the mixture stirred for 1 hr at 80° C. The reaction was diluted with EtOAc (50 mL) and washed with saturated aqueous NaHCO$_3$ (2×50 mL) and brine (100 mL), and the organic layer dried over Na$_2$SO$_4$ and evaporated. The crude product was purified by silica gel chromatography (Thomson Scientific 24-g cartridge, 5-40% EtOAc/heptane in 10 column volumes) to give 190 mg (39%) of compound 14 as a white solid. $^1$H NMR (CHLOROFORM-d) δ: 7.40 (dd, J=7.7, 1.6 Hz, 1H), 7.35 (d, J=1.5 Hz, 1H), 7.20-7.25 (m, 2H), 7.10-7.15 (m, 2H), 7.03 (td, J=7.6, 1.1 Hz, 1H), 6.85-6.90 (m, 1H), 5.98 (s, 1H), 4.97 (quin, J=4.5 Hz, 1H), 3.56-3.78 (m, 4H), 3.49 (s, 3H), 2.03-2.18 (m, 4H). Mass spectrum (ESI, m/z): Calcd. for $C_{22}H_{21}ClF_3N_3O_4S$, 516.1 (M+H), found 516.0.

Example 23

4-{[5-(4-Chlorophenyl)-1-(2-methoxyphenyl)-1H-pyrazol-3-yl]oxy}-1-(cyclopropylsulfonyl)piperidine (Cpd 15)

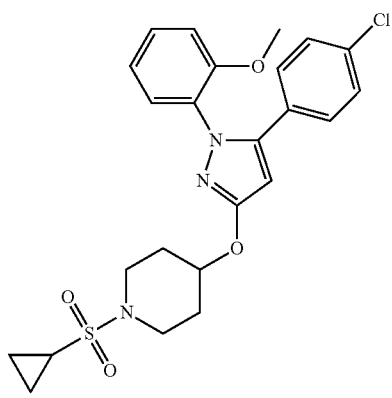 [SMILES: COc1ccccc1-n1nc(OC2CCN(S(=O)(=O)C3CC3)CC2)cc1-c1ccc(Cl)cc1]

To a solution of compound 17a (75 mg, mmol) and NEt$_3$ (0.063 mL, 0.45 mmol) in 1 mL of DCM at 0° C. was added cyclopropylsulfonyl chloride (0.014 mL) and the mixture stirred for 1 hr at RT. The mixture was concentrated and the residue purified by RP-HPLC (C18) eluting with a linear gradient of 40-100% CH$_3$CN in 0.1% TFA/H$_2$O over 18 min to give 58 mg (80%) of compound 15 as a white solid. $^1$H NMR (CHLOROFORM-d) δ: 7.33-7.41 (m, 2H), 7.20-7.25 (m, 2H), 7.13 (d, J=8.6 Hz, 2H), 7.02 (td, J=7.7, 1.3 Hz, 1H), 6.88 (d, J=8.1 Hz, 1H), 5.98 (s, 1H), 4.79-4.86 (m, 1H), 3.49-3.58 (m, 5H), 3.35-3.44 (m, 2H), 2.31 (tt, J=8.0, 4.8 Hz, 1H), 2.04-2.16 (m, 4H), 1.16-1.22 (m, 2H), 0.98-1.04 (m, 2H). Mass spectrum (ESI, m/z): Calcd. for $C_{24}H_{26}ClN_3O_4S$, 488.1 (M+H), found 488.1.

Example 24

4-{[5-(4-Chlorophenyl)-1-(2-methoxyphenyl)-1H-pyrazol-3-yl]oxy}-1-[(1-methylethyl)sulfonyl]piperidine (Cpd 21)

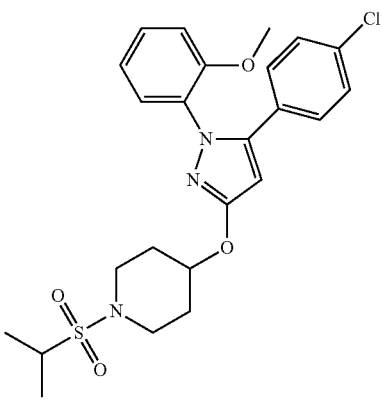 [SMILES: COc1ccccc1-n1nc(OC2CCN(S(=O)(=O)C(C)C)CC2)cc1-c1ccc(Cl)cc1]

To a solution of compound 17a (0.38 g, 0.76 mmol) and NEt$_3$ (0.43 mL, 3.05 mmol) in 5 mL of DCM at 0° C. was added isopropylsulfonyl chloride (0.093 mL, 0.84 mmol) and the mixture stirred for 1 hr at RT. The reaction was diluted with EtOAc (50 mL) and washed with saturated aqueous NaHCO$_3$ (2×50 mL) and brine (100 mL), and the organic layer dried over Na$_2$SO$_4$, filtered, and evaporated. The crude product was purified by silica gel chromatography (Thomson Scientific 24-g cartridge, 12-100% EtOAc/heptane in 10 column volumes) to give 360 mg (91%) of compound 21 as a white solid. $^1$H NMR (CHLOROFORM-d) δ: 7.41 (dd, J=7.7, 1.6 Hz, 1H), 7.35 (td, J=7.9, 1.6 Hz, 1H), 7.20-7.25 (m, 2H), 7.10-7.15 (m, 2H), 7.03 (td, J=7.6, 1.3 Hz, 1H), 6.87 (dd, J=8.3, 1.0 Hz, 1H), 5.96 (s, 1H), 4.90 (tt, J=6.4, 3.3 Hz, 1H), 3.61 (ddd, J=12.6, 8.6, 3.5 Hz, 1H), 3.49 (s, 3H), 3.38-3.46 (m, 2H), 3.22 (quin, 1H), 1.96-2.15 (m, 4H), 1.38 (d, J=6.8 Hz, 6H). Mass spectrum (ESI, m/z): Calcd. for $C_{24}H_{28}ClN_3O_4S$, 490.1 (M+H), found 490.1.

Example 25

4-({5-(4-Chlorophenyl)-1-[2-(1-methylethoxy)phenyl]-1H-pyrazol-3-yl}oxy)-1-[(1-methylethyl)sulfonyl]piperidine (Cpd 28)

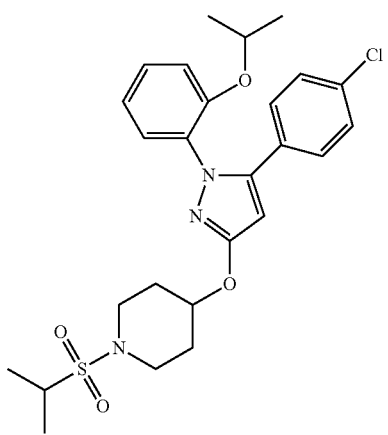 [SMILES: CC(C)Oc1ccccc1-n1nc(OC2CCN(S(=O)(=O)C(C)C)CC2)cc1-c1ccc(Cl)cc1]

a) 2-(5-(4-chlorophenyl)-3-((1-(methylsulfonyl)piperidin-4-yl)oxy)-1H-pyrazol-1-yl)phenol, 25a

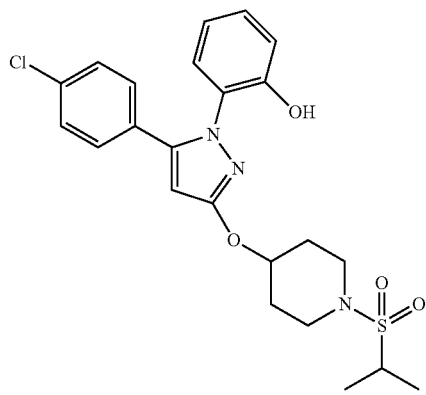 [SMILES: CC(C)S(=O)(=O)N1CCC(Oc2cc(-c3ccc(Cl)cc3)n(-c3ccccc3O)n2)CC1]

To a solution of compound 21 (0.36 g, 0.74 mmol) in 2 mL of DCM at −78° C. was added a 1 M solution of boron tribromide in DCM (0.88 mL, 0.88 mmol) and the mixture stirred for 1 hr. The reaction was diluted with EtOAc (50 mL) and washed with saturated aqueous NaHCO$_3$ (2×50 mL) and brine (100 mL), and the organic layer dried over Na$_2$SO$_4$, filtered, and evaporated. The crude product was purified by silica gel chromatography (Thomson Scientific 40-g cartridge, 6-50% EtOAc/heptane in 10 column volumes) to give 200 mg (57%) of compound 25a as a white solid.

b) 4-({5-(4-Chlorophenyl)-1-[2-(1-methylethoxy)phenyl]-1H-pyrazol-3-yl}oxy)-1-[(1-methylethyl)sulfonyl]piperidine, Cpd 28

To a mixture of compound 25a (0.20 g, 0.42 mmol) and K$_2$CO$_3$ (0.12 g, 0.84 mmol) in 2 mL of acetone at RT was added isopropyliodide (0.042 mL, 0.42 mmol) and the mixture stirred for 8 hr at 60° C. The reaction was diluted with EtOAc (50 mL) and washed with saturated aqueous NaHCO$_3$ (2×50 mL) and brine (100 mL), and the organic layer dried over Na$_2$SO$_4$, filtered, and evaporated. The crude product was purified by silica gel chromatography (Thomson Scientific 40-g cartridge, 3-40% EtOAc/heptane in 10 column volumes) to give 110 mg (50%) of compound 28 as a white solid. $^1$H NMR (CHLOROFORM-d) d: 7.45 (dd, J=7.7, 1.6 Hz, 1H), 7.25-7.32 (m, 1H), 7.16-7.22 (m, 2H), 7.09-7.15 (m, 2H), 7.00 (td, J=7.6, 1.3 Hz, 1H), 6.81 (d, J=7.6 Hz, 1H), 5.93 (s, 1H), 4.87 (tt, J=6.6, 3.3 Hz, 1H), 4.25 (spt, J=6.1 Hz, 1H), 3.60 (ddd, J=12.5, 8.5, 3.5 Hz, 2H), 3.35-3.43 (m, 2H), 3.20 (spt, J=6.9 Hz, 1H), 1.94-2.12 (m, 4H), 1.35 (d, J=6.8 Hz, 6H), 0.85-1.02 (m, 6H) Mass spectrum (ESI, m/z): Calcd. for C$_{26}$H$_{32}$ClN$_3$O$_4$S, 518.2 (M+H), found 518.1.

Example 26

4-{[5-(4-Chlorophenyl)-1-(2-methoxyphenyl)-1H-pyrazol-3-yl]oxy}cyclohexanone (Cpd 2)

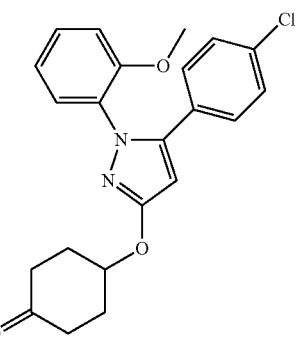

a) 3-(1,4-dioxaspiro[4.5]decan-8-yloxy)-5-(4-chlorophenyl)-1-(2-methoxyphenyl)-1H-pyrazole, 26a

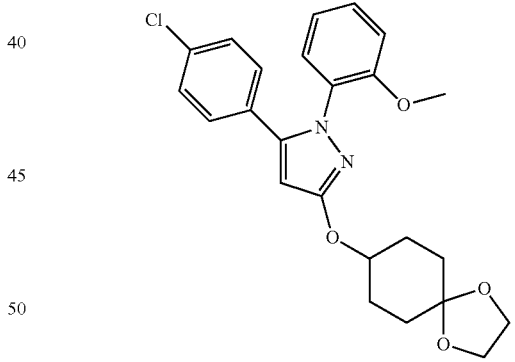

Compound 26a was prepared according to the procedure described in Example 1, substituting 4-hydroxycyclohexanone monoethylene ketal for 2,2,6,6-tetramethyldihydro-2H-pyran-4(3H)-one in step (c). $^1$H NMR (CHLOROFORM-d) δ: 7.40 (dd, J=7.7, 1.6 Hz, 1H), 7.28-7.34 (m, 1H), 7.16-7.21 (m, 2H), 7.05-7.14 (m, 2H), 7.00 (td, J=7.6, 1.3 Hz, 1H), 6.79-6.86 (m, 1H), 5.94 (s, 1H), 4.76 (quin, J=5.1 Hz, 1H), 3.91-4.01 (m, 4H), 3.45 (s, 3H), 1.98-2.06 (m, 4H), 1.88-1.97 (m, 2H), 1.64 (dt, 2H).

b) 4-{[5-(4-Chlorophenyl)-1-(2-methoxyphenyl)-1H-pyrazol-3-yl]oxy}cyclohexanone, Cpd 2

To a solution of compound 26a (50 mg, mmol) in 2 mL of acetone at RT was added 4 drops of 6N HCl and the mixture was stirred for 1 hr at RT. The reaction was diluted with EtOAc (50 mL) and washed with saturated aqueous NaHCO₃ (2×50 mL) and brine (100 mL), and the organic layer dried over Na₂SO₄, filtered, and evaporated. The crude product was purified by silica gel chromatography (Thomson Scientific 12-g cartridge, 3-30% EtOAc/heptane in 10 column volumes) to give 28 mg (63%) of compound 2 as a white solid. ¹H NMR (CHLOROFORM-d) δ: 7.40 (dd, J=7.8, 1.8 Hz, 1H), 7.33 (td, J=8.0, 1.8 Hz, 1H), 7.17-7.24 (m, 2H), 7.09-7.15 (m, 2H), 7.02 (td, J=7.6, 1.3 Hz, 1H), 6.85 (dd, J=8.3, 1.3 Hz, 1H), 5.98 (s, 1H), 5.02-5.11 (m, 1H), 3.47 (s, 3H), 2.66-2.79 (m, 2H), 2.31-2.44 (m, 4H), 2.08-2.19 (m, 2H). Mass spectrum (ESI, m/z): Calcd. for C₂₂H₂₁ClN₂O₃, 397.1 (M+H), found 397.0.

Example 27

4-({5-(4-Chlorophenyl)-1-[2-(1-methylethoxy)phenyl]-1H-pyrazol-3-yl}oxy)-1-(methylsulfonyl)piperidine (Cpd 20)

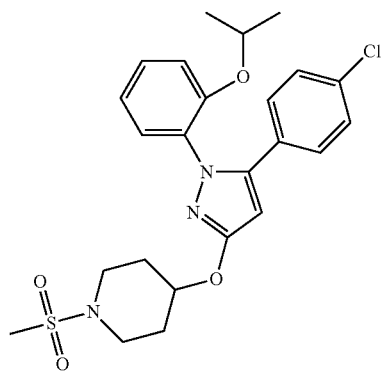 [SMILES: CC(C)Oc1ccccc1-n1nc(OC2CCN(S(C)(=O)=O)CC2)cc1-c1ccc(Cl)cc1]

The title compound was prepared from compound 5 of Example 19 using the procedures described in Example 25. ¹H NMR (CHLOROFORM-d) δ: 7.44 (dd, J=7.8, 1.8 Hz, 1H), 7.29-7.37 (m, 1H), 7.19-7.24 (m, 2H), 7.10-7.16 (m, 2H), 7.00 (td, J=7.6, 1.3 Hz, 1H), 6.82 (d, J=7.6 Hz, 1H), 5.96 (s, 1H), 4.79 (quin, J=4.5 Hz, 1H), 4.29 (spt, J=6.1 Hz, 1H), 3.31-3.44 (m, 4H), 2.81 (s, 3H), 2.09 (q, 4H), 0.98 (m, 6H). Mass spectrum (ESI, m/z): Calcd. for C₂₄H₂₈ClN₃O₄S, 490.1 (M+H), found 490.1.

Example 28

4-{[1-(2-tert-Butoxyphenyl)-5-(4-chlorophenyl)-1H-pyrazol-3-yl]oxy}-1-(methylsulfonyl)piperidine (Cpd 24)

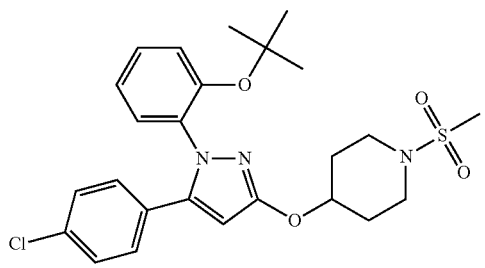 [SMILES: CC(C)(C)Oc1ccccc1-n1nc(OC2CCN(S(C)(=O)=O)CC2)cc1-c1ccc(Cl)cc1]

a) 2-(5-(4-chlorophenyl)-3-((1-(methylsulfonyl)piperidin-4-yl)oxy)-1H-pyrazol-1-yl)phenol, 28a

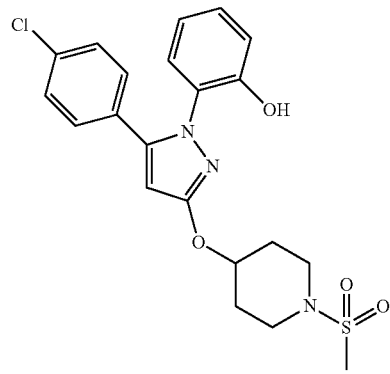 [SMILES: CS(=O)(=O)N1CCC(Oc2cc(-c3ccc(Cl)cc3)n(-c3ccccc3O)n2)CC1]

Compound 28a was prepared according to the procedures described in Example 25, step (a), substituting compound 5 of Example 19 for compound for compound 21.

b) 4-{[1-(2-tert-Butoxyphenyl)-5-(4-chlorophenyl)-1H-pyrazol-3-yl]oxy}-1-(methylsulfonyl)piperidine, Cpd 24

To a solution of compound 28a (50 mg, 0.11 mmol) in 0.5 mL of toluene was added of N,N dimethylformamide di-tert-butyl acetal (0.5 mL, mmol) and the mixture heated to 80° C. for 30 min. The reaction was diluted with EtOAc (25 mL) and washed with saturated aqueous NaHCO₃ (2×25 mL) and brine (50 mL), and the organic layer dried over Na₂SO₄, filtered, and evaporated. The crude product was purified by silica gel chromatography (Thomson Scientific 12-g cartridge, 5-40% EtOAc/heptane in 10 column volumes) to give 50 mg (95%) of the title compound as a white solid. ¹H NMR (CHLOROFORM-d) δ: 7.56 (dd, J=7.8, 1.8 Hz, 1H), 7.26-7.31 (m, 1H), 7.16-7.23 (m, 3H), 7.06-7.12 (m, 2H), 6.97 (dd, J=8.2, 1.4 Hz, 1H), 5.95 (s, 1H), 4.87 (quin, J=4.6 Hz, 1H), 3.33-3.45 (m, 4H), 2.82 (s, 3H), 2.10 (d, 4H), 1.03 (s, 9H). Mass spectrum (ESI, m/z): Calcd. for C₂₅H₃₀ClN₃O₄S, 504.2 (M+H), found 504.0.

Example 29 tert-Butyl 4-{[5-(4-chlorophenyl)-1-(2-ethylphenyl)-1H-pyrazol-3-yl]oxy}piperidine-1-carboxylate (Cpd 18)

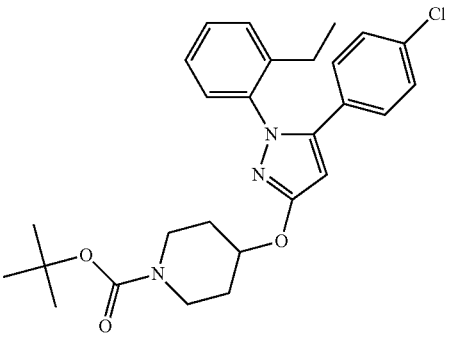 [SMILES: CCc1ccccc1-n1nc(OC2CCN(C(=O)OC(C)(C)C)CC2)cc1-c1ccc(Cl)cc1]

a) N'-(2-ethylphenyl)acetohydrazide, 29a

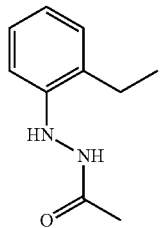

Compound 29a was prepared according to the procedure in Example 1, step (a), substituting (2-ethylphenyl)hydrazine for (2-methoxyphenyl)hydrazine. $^1$H NMR (CHLOROFORM-d) δ: 7.25 (br s, 0.6H), 7.14-7.23 (m, 2H), 6.85-7.00 (m, 2H), 6.82 (br s 0.4, 2H), 6.16 (br. s., 0.6H), 5.85 (br s, 0.4H), 2.46-2.75 (m, 2H), 2.06-2.17 (m, 3H), 1.30 (t, 3H) (rotational isomers).

b) 5-(4-Chlorophenyl)-1-(2-ethylphenyl)-1H-pyrazol-3(2H)-one, 29b

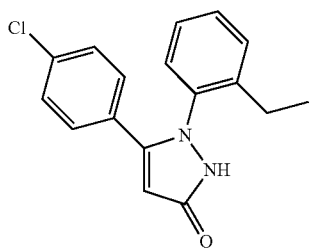 [SMILES: CCc1ccccc1-n1[nH]c(=O)cc1-c1ccc(Cl)cc1]

Compound 29b was prepared according to the procedure in Example 1, step (b), substituting compound 29a for compound 1a. $^1$H NMR (DMSO-$d_6$) δ: 7.31-7.42 (m, 4H), 7.25 (td, J=7.3, 2.0 Hz, 1H), 7.11-7.18 (m, 3H), 6.02 (s, 1H), 4.03 (q, J=7.1 Hz, 2H), 1.18 (t, J=7.2 Hz, 3H).

c) tert-Butyl 4-{[5-(4-chlorophenyl)-1-(2-ethylphenyl)-1H-pyrazol-3-yl]oxy}piperidine-1-carboxylate, Cpd 18

Compound 18 was prepared from compound 29b and commercially available 1-Boc-4-methanesulfonyloxypiperidine according to the procedure in Example 1, step (e). $^1$H NMR (CHLOROFORM-d) δ: 7.29-7.39 (m, 2H), 7.12-7.25 (m, 4H), 7.04-7.10 (m, 2H), 5.99 (s, 1H), 4.85 (tt, J=7.7, 3.8 Hz, 1H), 3.77 (d, J=10.6 Hz, 2H), 3.25-3.35 (m, 2H), 2.41 (q, J=7.4 Hz, 2H), 1.98-2.09 (m, 2H), 1.73-1.88 (m, 2H), 1.49 (s, 10H), 1.07 (t, 3H). Mass spectrum (ESI, m/z): Calcd. for $C_{27}H_{32}ClN_3O_3$, 481.2 (M+H), found 481.9.

Example 30

4-{[5-(4-Chlorophenyl)-1-(2-ethylphenyl)-1H-pyrazol-3-yl]oxy}-1-(methylsulfonyl)piperidine (Cpd 19)

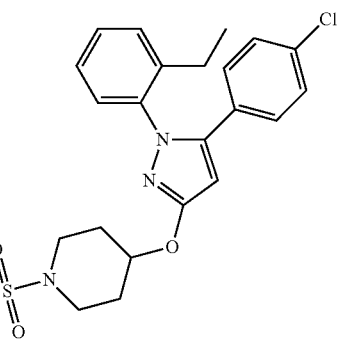

a) 4-((1-(2-ethylphenyl)-5-(4-methoxyphenyl)-1H-pyrazol-3-yl)oxy)piperidine trifluoroacetate, 30a

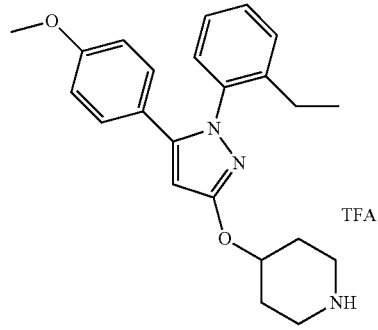 [SMILES: CCc1ccccc1-n1nc(OC2CCNCC2)cc1-c1ccc(OC)cc1]

To a solution of compound 18 (700 mg, 1.50 mmol) in 5 mL of DCM at RT was added 5 mL of TFA and the mixture stirred for 1 hr. The mixture was concentrated and used without further purification. $^1$H NMR (MeOH) δ: 7.41-7.47 (m, 1H), 7.36-7.40 (m, 1H), 7.21-7.33 (m, 4H), 7.15-7.21 (m, 2H), 6.24 (s, 1H), 4.83-4.89 (m, 1H), 3.44 (ddd, J=12.8, 9.0, 3.7 Hz, 2H), 3.20-3.30 (m, 2H), 2.36 (q, J=7.6 Hz, 2H), 2.06-2.30 (m, 4H), 1.02 (t, 3H).

b) 4-{[5-(4-Chlorophenyl)-1-(2-ethylphenyl)-1H-pyrazol-3-yl]oxy}-1-(methylsulfonyl)piperidine, Cpd 19

To a solution of compound 30a (130 mg, 0.26 mmol) and NEt$_3$ (0.091 mL, 0.66 mmol) in 3 mL of DCM at 0° C. was added methanesulfonyl chloride (0.024 mL, 0.32 mmol) and the reaction was stirred for 2 hr at RT. The mixture was concentrated and the residue purified by RP-HPLC (C18) eluting with a linear gradient of 40-100% CH$_3$CN in 0.1% TFA/H$_2$O over 18 min to give 70 mg (46%) of compound 19 as a white solid. $^1$H NMR (CHLOROFORM-d) δ: 7.25-7.31 (m, 1H), 7.21-7.25 (m, 1H), 7.06-7.16 (m, 4H), 6.98 (d, J=8.6 Hz, 2H), 5.91 (s, 1H), 4.79 (quin, J=4.7 Hz, 1H), 3.23-3.39 (m, 4H), 2.74 (s, 3H), 2.31 (q, J=7.6 Hz, 2H), 1.96-2.05 (m, 4H), 0.97 (t, 3H). Mass spectrum (ESI, m/z): Calcd. for $C_{23}H_{26}ClN_3O_3S$, 460.0 (M+H), found 460.1.

Example 31

5-(4-Chlorophenyl)-3-(1,4-dioxaspiro[4.5]dec-8-yloxy)-1-(2-ethylphenyl)-1H-pyrazole (Cpd 17)

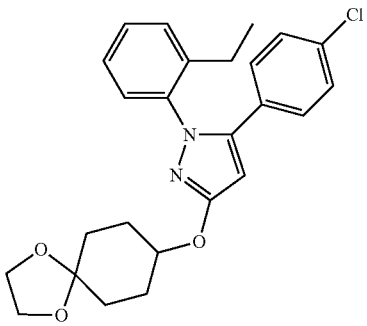 [SMILES: CCc1ccccc1-n1nc(OC2CCC3(CC2)OCCO3)cc1-c1ccc(Cl)cc1]

Compound 17 was prepared from compound 29b of Example 29 and commercially available 4-hydroxycyclohexanone monoethylene ketal according to the procedures in Example 1. $^1$H NMR (CHLOROFORM-d) δ: 7.29-7.38 (m, 2H), 7.14-7.24 (m, 4H), 7.07 (d, J=8.6 Hz, 2H), 5.99 (s, 1H), 4.79 (quin, J=5.2 Hz, 1H), 3.95-4.04 (m, 4H), 2.42 (q, J=7.6 Hz, 2H), 2.00-2.07 (m, 4H), 1.90-1.99 (m, 2H), 1.66 (dt, J=12.8, 6.1 Hz, 2H), 1.07 (t, 3H). Mass spectrum (ESI, m/z): Calcd. for $C_{25}H_{22}ClN_2O_3$, 439.2 (M+H), found, 438.9.

Example 32 tert-Butyl (cis-4-{[5-(4-chlorophenyl)-1-(2-methoxyphenyl)-1H-pyrazol-3-yl]oxy}cyclohexyl) carbamate (Cpd 11)

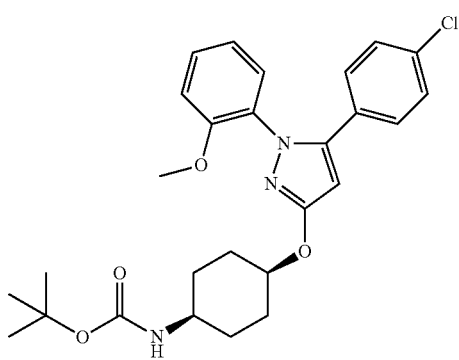 [SMILES: COc1ccccc1-n1nc(O[C@H]2CC[C@@H](NC(=O)OC(C)(C)C)CC2)cc1-c1ccc(Cl)cc1]

a) (trans-4-((tert-butoxycarbonyl)amino)cyclohexyl methanesulfonate, 32a

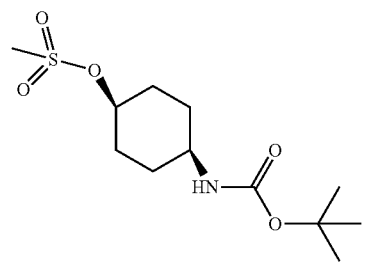 [SMILES: CC(C)(C)OC(=O)N[C@H]1CC[C@@H](OS(C)(=O)=O)CC1]

To a solution of commercially available tert-butyl (trans-4-hydroxycyclohexyl)carbamate (1.09 g, 5.06 mmol) and NEt$_3$ (1.06 mL, 7.59 mmol) in 10 mL of DCM at 0° C. was added methanesulfonyl chloride (0.46 mL, 6.07 mmol) and the reaction was stirred for 2 hr at RT. The reaction was diluted with EtOAc (50 mL) and washed with saturated aqueous NaHCO$_3$ (2×50 mL) and brine (50 mL). The organic layer was dried over Na$_2$SO$_4$, filtered, and the filtrate concentrated under reduced pressure to give 1.40 g (94%) of compound 11 as a white solid that was used in the next step without further purification.

b) tert-Butyl (cis-4-{[5-(4-chlorophenyl)-1-(2-methoxyphenyl)-1H-pyrazol-3-yl]oxy}cyclohexyl)carbamate, Cpd 11

The title compound 11 was prepared from compound 32a and compound 1b according to the procedure in Example 1, step (e). $^1$H NMR (CHLOROFORM-d) δ: 7.42 (dd, J=7.7, 1.6 Hz, 1H), 7.30-7.36 (m, 1H), 7.19-7.25 (m, 2H), 7.09-7.16 (m, 2H), 7.02 (td, J=7.6, 1.1 Hz, 1H), 6.86 (dd, J=8.3, 1.0 Hz, 1H), 5.95 (s, 1H), 4.78 (br. s., 1H), 4.53 (br. s., 1H), 3.48 (s, 3H), 2.08-2.17 (m, 2H), 1.61-1.84 (m, 6H), 1.47 (s, 9H). Mass spectrum (ESI, m/z): Calcd. for $C_{27}H_{32}ClN_3O_4$, 498.0 (M+H), found 498.0.

Example 33 cis-4-{[5-(4-Chlorophenyl)-1-(2-methoxyphenyl)-1H-pyrazol-3-yl]oxy}cyclohexanamine trifluoroacetate (Cpd 12)

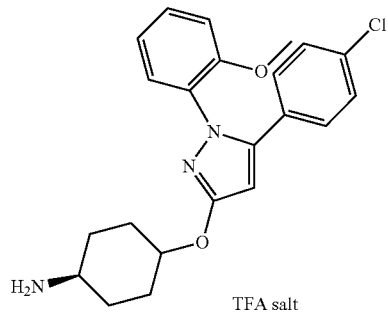

To a solution of compound 11 (200 mg, 0.40 mmol) in 2 mL of DCM at RT was added 2 mL of TFA and the mixture stirred for 1 hr. The mixture was concentrated and the residue purified by RP-HPLC (C18) eluting with a linear gradient of 40-100% CH$_3$CN in 0.1% TFA/H$_2$O over 18 min to give 150 mg (73%) compound 12 as a white solid. $^1$H NMR (CHLOROFORM-d) δ: 10.49 (br. s., 1H), 7.95 (br. s., 2H), 7.30-7.41 (m, 2H), 7.19-7.26 (m, 2H), 7.12 (d, J=8.6 Hz, 2H), 7.00 (t, J=7.6 Hz, 1H), 6.89 (d, J=7.8 Hz, 1H), 5.98 (s, 1H), 4.65 (br. s., 1H), 3.52 (s, 3H), 3.14 (br. s., 1H), 2.19 (d, J=13.6 Hz, 2H), 1.86 (br. s., 4H), 1.55 (d, 2H). Mass spectrum (ESI, m/z): Calcd. for $C_{22}H_{24}ClN_3O_2$, 398.1 (M+H), found 398.1.

Example 34

N-(cis-4-{[5-(4-Chlorophenyl)-1-(2-methoxyphenyl)-1H-pyrazol-3-yl]oxy}cyclohexyl)-2,2,2-trifluoroacetamide (Cpd 13)

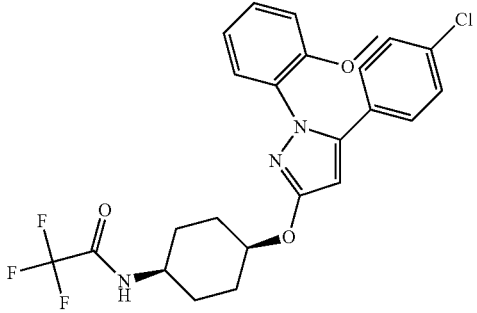 [SMILES: COc1ccccc1-n1nc(O[C@H]2CC[C@@H](NC(=O)C(F)(F)F)CC2)cc1-c1ccc(Cl)cc1]

To a solution of compound 12 (25 mg, 0.05 mmol and pyridine (0.012 mL, 0.147 mmol) in 1 mL of DCM at 0° C. was added trifluoromethanesulfonic anhydride (0.010 mL, 0.063 mmol) and the reaction was stirred for 2 hr at RT. The reaction was diluted with EtOAc (25 mL) and washed with saturated aqueous NaHCO$_3$ (2×25 mL) and brine (25 mL). The organic layer was dried over Na$_2$SO$_4$, filtered, and concentrated under reduced pressure to give 22 mg (74%) of compound 13 as a white solid. $^1$H NMR (CHLOROFORM-d) δ: 7.33-7.40 (m, 2H), 7.21-7.26 (m, 2H), 7.11-7.15 (m, 2H), 7.02 (td, J=7.7, 1.3 Hz, 1H), 6.88 (d, J=8.3 Hz, 1H), 6.38 (d, J=7.1 Hz, 1H), 5.98 (s, 1H), 4.76-4.81 (m, 1H), 3.91-4.03 (m, 1H), 3.52 (s, 3H), 2.22 (dd, J=12.6, 3.3 Hz, 2H), 1.67-1.90 (m, 6H). Mass spectrum (ESI, m/z): Calcd. for $C_{24}H_{23}ClF_3N_3O_3$, 494.0 (M+H), found 494.0.

Example 35

5-(4-Chlorophenyl)-3-[(4,4-difluorocyclohexyl)oxy]-1-(2-methoxyphenyl)-1H-pyrazole (Cpd 16)

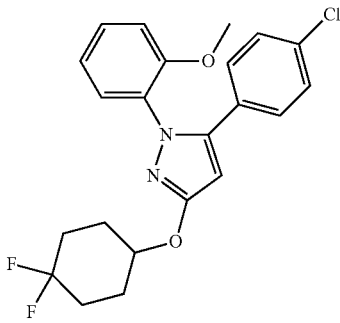 [SMILES: COc1ccccc1-n1nc(OC2CCC(F)(F)CC2)cc1-c1ccc(Cl)cc1]

To a solution of compound 2 (20 mg, 0.05 mmol) (Example 26) and 0.0006 mL of ethanol (0.2 eq) in 0.5 mL of DCM was added bis(2-methoxyethyl)aminosulfur trifluoride (0.016 mL, 0.090 mmol) and the mixture was stirred overnight at RT. Another portion of bis(2-methoxyethyl)aminosulfur trifluoride (0.016 mL, 0.090 mmol) was added and the mixture stirred for an additional 8 hr. The residue was concentrated and purified by RP-HPLC (C18), eluting with a linear gradient of 40-100% $CH_3CN$ in 0.1% TFA/$H_2O$ over 18 min to give 16 mg (60%) of the title compound 16 as a white solid. $^1H$ NMR (CHLOROFORM-d) δ: 7.24-7.32 (m, 2H), 7.10-7.17 (m, 2H), 7.00-7.07 (m, 2H), 6.93 (td, J=7.6, 1.3 Hz, 1H), 6.79 (d, J=8.3 Hz, 1H), 5.90 (s, 1H), 4.75-4.83 (m, 1H), 3.43 (s, 3H), 1.79-2.50 (m, 8H). Mass spectrum (ESI, m/z): Calcd. for $C_{22}H_{21}ClF_2N_2O_2$, 419.0 (M+H), found 419.0.

Example 36

5-(4-Chlorophenyl)-1-(2-methoxyphenyl)-3-[(2,2,4,4-tetramethyloxetan-3-yl))methoxy]-1H-pyrazole (Cpd 40)

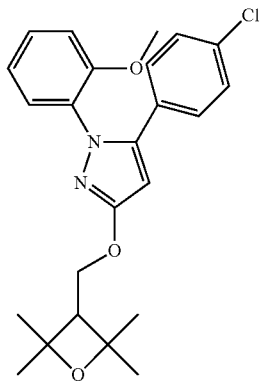 [SMILES: COc1ccccc1-n1nc(OCC2C(C)(C)OC2(C)C)cc1-c1ccc(Cl)cc1]

a) 4-Diazo-2,2,5,5-tetramethyl-dihydro-furan-3-one, 36a

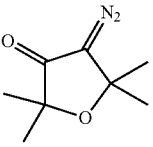

To a solution of 2,2,5,5-tetramethyltetrahydrofuran-3-one (0.32 mL, 2.08 mmol, 1 eq), 2,4,6-triisopropylbenzenesulfonyl azide (1.79 g, 5.2 mmol, 2.5 eq), 18-crown-6 (55 mg, 0.21 mmol, 0.1 eq), and tetrabutylammonium bromide (335 mg, 1.04 mmol, 0.5 eq) in benzene (30 mL) was added KOH (30 mL of 50% aq solution). The solution was warmed to 40° C. and stirred vigorously. After 5 hr, the reaction mixture was cooled, diluted with water, and extracted with ether. The combined organic phases were dried over $MgSO_4$, filtered, and concentrated. Purification by chromatography (40 g), eluting with 5 to 15% EA/heptanes, gave compound 36a (400 mg, 96%). $^1H$ NMR (CHLOROFORM-d) δ: 1.60 (s, 6H), 1.37 (s, 6H).

b) 2,2,4,4-Tetramethyl-oxetane-3-carboxylic acid methyl ester, 36b

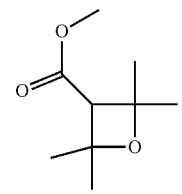

A solution of compound 36a (400 mg, 2.38 mmol) in methanol (10 mL) under argon was irradiated in a quartz flask with UV light overnight. The solution was concentrated to give compound 36b (347 mg, 85%) which was used in subsequent reactions without further purification. $^1H$ NMR (CHLOROFORM-d) δ: 3.69 (s, 3H), 3.31 (s, 1H), 1.48 (s, 12H).

c) 2,2,4,4-tetramethyl-oxetan-3-yl)-methanol, 36c

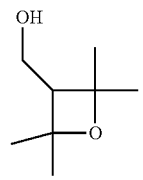

To a solution of compound 36b (347 mg, 2.01 mmol, 1 eq) in THF (5 mL) at 0° C. was added $LiAlH_4$ (1.0 mL of a 1 M solution in THF, 1.0 mmol, 0.5 eq), and the mixture was stirred for 8 hr at RT. To the reaction was added tartrate (1 mL) and the reaction was then stirred for 20 min before being decanted. The decanted solution was washed subsequently with DCM and 1 N HCl, and the organic phase was dried over $MgSO_4$, filtered, and concentrated to give compound 36c (274 mg, 70% pure, 66%).

d) (2,2,4,4-Tetramethyloxetan-3-yl)methyl 4-methylbenzenesulfonate, 36d

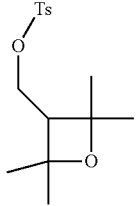

To a solution of compound 36c (274 mg, 1.33 mmol, 1 eq) in DCM (5 mL) was added p-toluenesulfonyl chloride (507 mg, 2.66 mmol, 2 eq) and pyridine (0.27 mL, 3.32 mmol, 2.5 eq), and the reaction was allowed to stir for 3 days at rt. Water and 1 N HCl were added to the reaction mixture, which was then extracted with DCM. The combined organic phases were dried over MgSO$_4$, filtered, and concentrated. Purification by chromatography (12 g), eluting with 10 to 50% EtOAc/heptanes gave the compound 36d (139 mg, 35%). $^1$H NMR (CHLOROFORM-d) δ: 7.75-7.84 (m, J=7.8 Hz, 2H), 7.31-7.41 (m, J=8.1 Hz, 2H), 4.21 (d, J=8.1 Hz, 2H), 2.70 (t, J=7.9 Hz, 1H), 2.47 (s, 3H), 1.39 (s, 6H), 1.22 (s, 6H).

e) 5-(4-Chlorophenyl)-1-(2-methoxyphenyl)-3-[(2,2,4,4-tetramethyloxetan-3-yl)methoxy]-1H-pyrazole, Cpd 40

To a suspension of compound 1b (50 mg, 0.17 mmol, 1 eq) in toluene (2 mL) was added compound 36d (60 mg, 0.2 mmol, 1.2 eq) and Cs$_2$CO$_3$ (108 mg, 0.33 mmol, 2 eq), and the suspension heated to 125° C. overnight. Water and 1 N HCl were subsequently added and the mixture was extracted with DCM. The combined organic extracts were dried over MgSO$_4$, filtered, and concentrated. Purification by chromatography (8 g), eluting with 20 to 40% EtOAc/heptanes, gave the title compound 40. An additional purification was performed by HPLC, eluting with 30 to 90% ACN/H$_2$O, to give the title compound 40 (25.3 mg, 34%). $^1$H NMR (CHLOROFORM-d) δ: 7.42 (d, J=7.6 Hz, 1H), 7.29-7.36 (m, 1H), 7.15-7.23 (m, J=8.1 Hz, 2H), 7.07-7.14 (m, J=8.3 Hz, 2H), 7.02 (t, J=7.7 Hz, 1H), 6.85 (d, J=8.3 Hz, 1H), 5.94 (s, 1H), 4.42 (d, J=7.8 Hz, 2H), 3.47 (s, 3H), 2.88 (t, J=7.8 Hz, 1H), 1.48 (s, 6H), 1.38 (s, 6H). ESI-MS (m/z): Calcd. for C$_{24}$H$_{27}$ClN$_2$O$_3$: 427.2 (M+1); found: 427.2.

Example 37

4-{[5-(4-Chlorophenyl)-1-(2-methoxyphenyl)-1H-pyrazol-3-yl]oxy}-2,2,6,6-tetramethylcyclohexanone (Cpd 41)

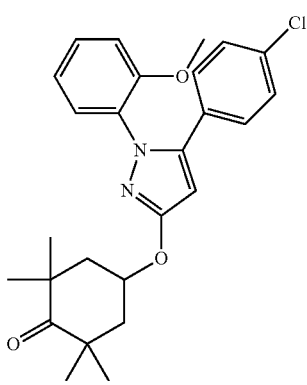 [SMILES: COc1ccccc1-n1nc(OC2CC(C)(C)C(=O)C(C)(C)C2)cc1-c1ccc(Cl)cc1]

A solution of compound 2 (Example 26, 82 mg, 0.2 mmol), and iodomethane (0.1 mL, 1.65 mmol) in DMSO (0.2 mL) was added dropwise to a suspension of powdered KOH (232 mg, 4 mmol) in DMSO (0.2 mL) at 55° C. The resulting mixture was stirred for 60 min, cooled to room temperature and diluted with water. The aqueous solution was extracted with EtOAc. The EtOAc fraction was washed with saturated NaCl, dried over Na$_2$SO$_4$, filtered, and the filtrate was concentrated under reduced pressure. The resultant residue was purified by silica column chromatography to give compound 41. $^1$H NMR (400 MHz, CHLOROFORM-d) δ ppm 1.18 (s, 6 H), 1.23 (s, 6 H), 1.96 (dd, J=13.4, 9.6 Hz, 2 H), 2.34 (dd, J=13.4, 4.8 Hz, 2 H), 3.45 (s, 3 H), 5.20 (dt, J=9.6, 4.8 Hz, 1 H), 5.87-6.02 (m, 1 H), 6.79-6.89 (m, 1 H), 7.03 (t, J=7.2 Hz, 1 H), 7.08-7.16 (m, 2 H), 7.16-7.24 (m, 2 H), 7.29-7.38 (m, 1 H), 7.38-7.46 (m, 1H). Mass spectrum (ESI, m/z): Calcd. for C$_{26}$H$_{29}$ClN$_2$O$_3$, 453.2 (M+H), found, 453.2.

Example 38

4-{[5-(4-Chlorophenyl)-1-(2-methoxyphenyl)-1H-pyrazol-3-yl]oxy}-2,2,6,6-tetramethylcyclohexanol (Cpd 42)

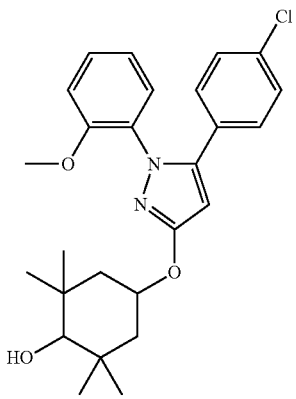 [SMILES: COc1ccccc1-n1nc(OC2CC(C)(C)C(O)C(C)(C)C2)cc1-c1ccc(Cl)cc1]

A solution of compound 41 (Example 37, 10 mg, 0.02 mmol) in MeOH was treated with sodium borohydride (1 mg 0.02 mmol) and the mixture stirred for 18 h. The reaction was quenched by adding a few drops of water. MeOH was removed under reduced pressure and the residue was taken in water and extracted with EtOAc. The EtOAc fraction was washed with saturated NaCl, dried over Na$_2$SO$_4$, filtered, and the filtrate concentrated under reduced pressure. The resultant residue was purified by preparative silica TLC to give compound 42. $^1$H NMR (400 MHz, CHLOROFORM-d) δ ppm 1.03 (s, 6 H), 1.04-1.07 (m, 6 H), 1.43 (d, J=12.1 Hz, 2 H), 2.13 (dd, J=12.4, 3.0 Hz, 2 H), 3.12 (br. s., 1 H), 3.39-3.48 (m, 3 H), 4.77 (ddd, J=11.3, 7.4, 4.3 Hz, 1 H), 5.92 (s, 1 H), 6.83 (d, J=8.3 Hz, 1 H), 7.02 (t, J=7.6 Hz, 1 H), 7.11 (d, J=8.3 Hz, 2 H), 7.20 (d, J=8.1 Hz, 2 H), 7.28-7.35 (m, 1 H), 7.42 (d, J=7.8 Hz, 1 H). Mass spectrum (ESI, m/z): Calcd. for C$_{26}$H$_{31}$ClN$_2$O$_3$, 455.2 (M+H), found, 455.2.

Example 39 tert-Butyl 3-{[5-(4-chlorophenyl)-1-(2-methoxyphenyl)-1H-pyrazol-3-yl]oxy}azetidine-1-carboxylate (Cpd 22)

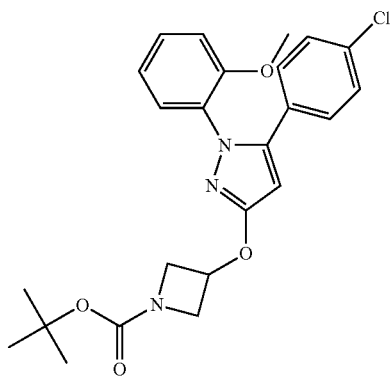 [SMILES: COc1ccccc1-n1nc(OC2CN(C(=O)OC(C)(C)C)C2)cc1-c1ccc(Cl)cc1]

a) tert-butyl 3-hydroxyazetidine-1-carboxylate, 39a

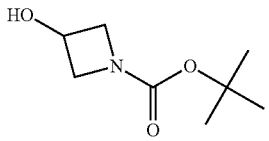

To a solution of 3-hydroxyazetidine (5 g, 68 5 mmol) in 20 mL of acetonitrile at RT was added di-tert-butyl dicarbonate (11.54 g, 52.87 mmol) and triethylamine (7.4 mL, 53.09 mmol). The mixture was stirred for 18 hr at room temperature. The solvent was removed under reduced pressure and the residue was triturated with hexanes and the hexanes decanted. The residual oil was dried under high vacuum to give 7.78 g (80%) of compound 39a as an off-white solid. $^1$H NMR (CHLOROFORM-d) δ: 1.43 (s, 9 H) 3.55-3.60 (m, 1 H) 3.75-3.83 (m, 2 H) 4.07-4.18 (m, 2 H) 4.49-4.63 (m, 1 H).

b) tert-butyl 3-((methylsulfonyl)oxy)azetidine-1-carboxylate, 39b

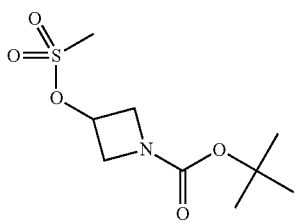 [SMILES: CC(C)(C)OC(=O)N1CC(OS(C)(=O)=O)C1]

A mixture of compound 39a (1.0 g, 5.78 mmol) and triethylamine (1.8 mL, 12 9 mmol) in 10 mL of DCE was cooled in an ice bath and treated with methanesulfonyl chloride (0.72 mL, 9.30 mmol). The mixture was stirred and allowed to warm up to room temperature over 4 h. The reaction mixture was diluted with DCM and washed sequentially with water and saturated NaCl. The organic layer was partitioned, dried over Na$_2$SO$_4$, filtered, and the filtrate concentrated under reduced pressure. The crude compound 39b was used without further purification.

c) tert-butyl-3-((5-(4-chlorophenyl)-1-(2-methoxyphenyl)-1H-pyrazol-3-yl)oxy)azetidine-1-carboxylate, Cpd 22

A flask was charged with compound 1b (0.20 g, 0.67 mmol), compound 39b (0.18 g, 0.73 mmol), cesium carbonate (0.26 g, 0 8 mmol) and DMF (3 mL) and heated at 80° C. for 6 h and 70° C. for 18 h. DMF was removed under reduce pressure and the residue was diluted with EtOAc and washed with water and saturated aqueous NaCl. The organic layer was dried over Na$_2$SO$_4$, filtered, and the filtrate concentrated under reduced pressure. The resultant residue was purified by silica gel preparative TLC to give compound 22. $^1$H NMR (400 MHz, CHLOROFORM-d) δ ppm 1.45 (s, 9 H), 3.44 (s, 3 H), 4.02-4.09 (m, 2 H), 4.28 (dd, J=9.9, 6.6 Hz, 2 H), 5.19 (ddd, J=6.6, 4.2, 2.4 Hz, 1 H), 5.93 (s, 1 H), 6.84 (d, J=8.3 Hz, 1 H), 6.98-7.06 (m, 1 H), 7.07-7.14 (m, 2 H), 7.17-7.24 (m, 2 H), 7.29-7.36 (m, 1 H), 7.38 (dd, J=7.7, 1.6 Hz, 1 H). Mass spectrum (ESI, m/z): Calcd. for C$_{24}$H$_{26}$ClN$_3$O$_4$, 455.2 (M+H), found 455.2.

Example 40

4-[(3-{[5-(4-Chlorophenyl)-1-(2-methoxyphenyl)-1H-pyrazol-3-yl]oxy}azetidin-1-yl)sulfonyl]-3,5-dimethylisoxazole (Cpd 30)

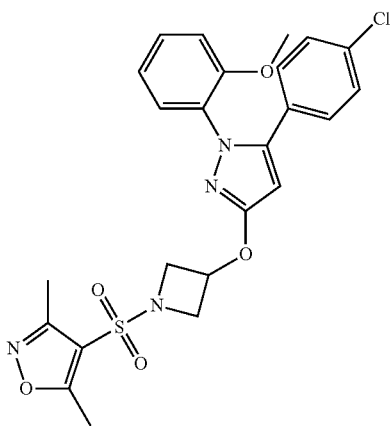 [SMILES: COc1ccccc1-n1nc(OC2CN(S(=O)(=O)c3c(C)noc3C)C2)cc1-c1ccc(Cl)cc1]

a) 3-(azetidin-3-yloxy)-5-(4-chlorophenyl)-1-(2-methoxyphenyl)-1H-pyrazole hydrochloride, 40a

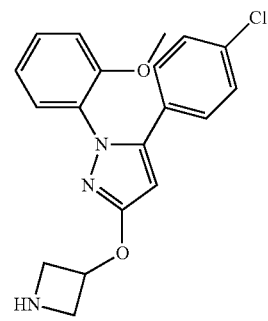

A flask charged with compound 22 (example 39, 1 g, 2 2 mmol) was treated with 4N HCl in dioxane (10 mL). The mixture was stirred for 5 h at room temperature. Dioxane was removed under reduced pressure and the residue was evaporated from toluene twice. The resulting oil, compound 40a, was used without further purification.

b) 4-[(3-{[5-(4-Chlorophenyl)-1-(2-methoxyphenyl)-1H-pyrazol-3-yl]oxy}azetidin-1-yl)sulfonyl]-3,5-dimethyl-isoxazole, 40b A flask was charged with compound 40a (33 mg, 0.09 mmol), TEA (0.052 mL, 0.37 mmol) and THF (3 mL) was treated with 3,5-dimethylisoxazole-4-sulfonyl chloride (36 mg, 0.185 mmol). The mixture was stirred for 18 h at room temperature. The reaction mixture was concentrated under reduced pressure and the residue was diluted with EtOAc and washed sequentially with 10% citric acid, water, and saturated NaCl. The EtOAc fraction was dried over anhydrous $Na_2SO_4$, filtered, and the filtrate concentrated under reduced pressure. The residue was purified by silica column chromatography to give 18.8 mg (39%) of compound 40b. $^1$H NMR (400 MHz, CHLOROFORM-d) δ ppm 2.44 (s, 3 H), 2.66 (s, 3 H), 3.44 (s, 3 H), 3.96 (dd, J=9.3, 5.1 Hz, 2 H), 4.19-4.28 (m, 2 H), 5.16-5.29 (m, 1 H), 5.92 (s, 1 H), 6.82-6.87 (m, 1 H), 7.02 (td, J=7.6, 1.1 Hz, 1 H), 7.08 (m, 2 H), 7.20 (m, 2 H), 7.33-7.37 (m, 2 H). Mass spectrum (ESI, m/z): Calcd. for $C_{24}H_{23}ClN_4O_5S$, 515.1 (M+H), found, 515.1

Example 41

3-{[5-(4-Chlorophenyl)-1-(2-methoxyphenyl)-1H-pyrazol-3-yl]oxy}-N-methoxy-N-methylazetidine-1-carboxamide (Cpd 29)

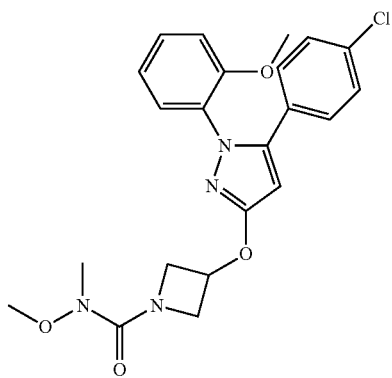 [SMILES: COc1ccccc1-n1nc(OC2CN(C(=O)N(C)OC)C2)cc1-c1ccc(Cl)cc1]

The title compound 29 was prepared in by an adaptation of Example 40, using compound 40a (33 mg, 0.09 mmol), TEA (0.052 mL, 0.37 mmol) and substituting methoxy(methyl)carbamic chloride (23 mg, 0.185 mmol) for 3,5-dimethylisoxazole-4-sulfonyl chloride. Purification by silica column chromatography gave 21.9 mg of title compound 29. $^1$H NMR (400 MHz, CHLOROFORM-d) δ ppm 3.10 (s, 3 H), 3.45 (s, 3 H), 3.61 (s, 3 H), 4.18-4.23 (m, 2 H), 4.45 (dd, J=10.7, 5.9 Hz, 2 H), 5.25 (ddd, J=6.5, 4.1, 2.5 Hz, 1 H), 5.94 (s, 1 H), 6.82-6.87 (m, 1 H), 7.00-7.05 (m, 1 H), 7.11 (m, 2 H), 7.21 (m, 2 H), 7.31-7.36 (m, 1 H), 7.39 (dd, J=7.7, 1.6 Hz, 1 H) Mass spectrum (ESI, m/z): Calcd. for $C_{22}H_{23}ClN_4O_4$, 443.1 (M+H), found, 443.1.

Example 42

5-(4-Chlorophenyl)-1-(2-methoxyphenyl)-3-{[1-(phenylcarbonyl)azetidin-3-yl]oxy}-1H-pyrazole (Cpd 27)

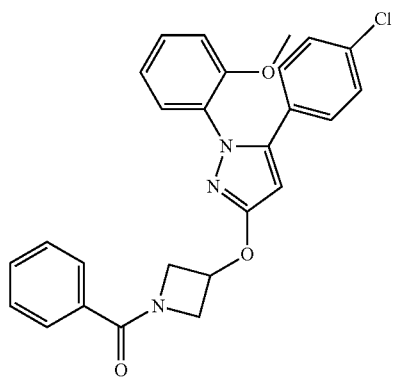 [SMILES: COc1ccccc1-n1nc(OC2CN(C(=O)c3ccccc3)C2)cc1-c1ccc(Cl)cc1]

A flask charged with compound 40a (20 mg, 0.05 mmol), TEA (0.035 mL, 0.25 mmol) and THF (2 mL) was treated with benzoyl chloride (0.15 mmol). The mixture was stirred for 18 h at room temperature. The reaction mixture was concentrated under reduced pressure and the residue was diluted with EtOAc and washed sequentially with saturated aqueous $NaHCO_3$, 1N HCl and saturated aqueous NaCl. The EtOAc fraction was dried over anhydrous $Na_2SO_4$, filtered, and the filtrate concentrated under reduced pressure. The residue was purified by silica preparative TLC followed by reverse phase HPLC to give compound 27. $^1$H NMR (400 MHz, ACETONITRILE-d3) δ ppm 3.36 (s, 3 H), 4.04 (d, J=8.8 Hz, 1 H), 4.27 (br. s., 1 H), 4.33-4.44 (m, 1 H), 4.44-4.56 (m, 1 H), 5.12 (tt, J=6.6, 4.0 Hz, 1 H), 5.96 (s, 1 H), 6.88 (dd, J=8.5, 1.1 Hz, 1 H), 6.94 (td, J=7.6, 1.3 Hz, 1 H), 7.08 (m, 2 H), 7.18 (m, 2 H), 7.24-7.45 (m, 5 H), 7.53-7.59 (m, 2 H). Mass spectrum (ESI, m/z): Calcd. for $C_{26}H_{22}ClN_3O_3$, 460.1 (M+H), found, 460.1.

Example 43

5-(4-Chlorophenyl)-1-(2-methoxyphenyl)-3-{[1-(methylsulfonyl)azetidin-3-yl]oxy}-1H-pyrazole (Cpd 26)

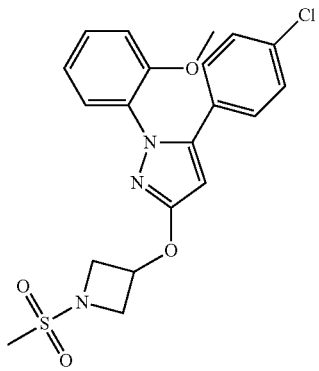 [SMILES: COc1ccccc1-n1nc(OC2CN(S(C)(=O)=O)C2)cc1-c1ccc(Cl)cc1]

A flask charged with compound 40a (20 mg, 0.05 mmol), TEA (0.035 mL, 0.25 mmol) and THF (2 mL) was treated with methanesulfonyl chloride (0.15 mmol). The mixture was stirred for 18 h at room temperature. The solvent was removed under reduced pressure and the residue was diluted with EtOAc and washed sequentially with saturated aqueous NaHCO$_3$, 1N HCl and saturated aqueous NaCl. The EtOAc fraction was dried over anhydrous Na$_2$SO$_4$, filtered, and the filtrate concentrated under reduced pressure. The residue was purified by silica preparative TLC to give compound 26. $^1$H NMR (400 MHz, ACETONITRILE-d3) δ ppm 2.84 (s, 3 H), 3.37 (s, 3 H), 3.91 (dd, J=10.2, 4.7 Hz, 2 H), 4.15 (dd, J=10.4, 6.6 Hz, 2 H), 5.04-5.12 (m, 1 H), 5.97 (s, 1 H), 6.90 (dd, J=8.3, 1.3 Hz, 1 H), 6.93-6.99 (m, 1 H), 7.09 (m, 2 H), 7.19 (m, 2 H), 7.25-7.29 (m, 1 H), 7.29-7.35 (m, 1 H) Mass spectrum (ESI, m/z): Calcd. for C$_{20}$H$_{20}$ClN$_3$O$_4$S, 434.1 (M+H), found 434.1.

Example 44

5-(4-Chlorophenyl)-1-(2-methoxyphenyl)-3-({1-[(1-methylethyl)sulfonyl]azetidin-3-yl}oxy)-1H-pyrazole (Cpd 25)

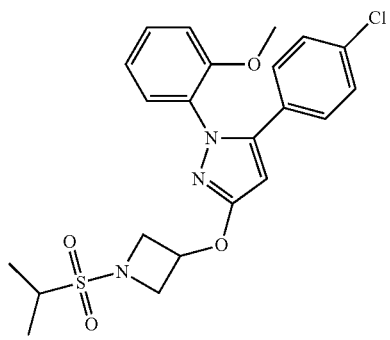 [SMILES: COc1ccccc1-n1nc(OC2CN(S(=O)(=O)C(C)C)C2)cc1-c1ccc(Cl)cc1]

A flask charged with compound 40a (20 mg, 0.05 mmol), TEA (0.035 mL, 0.25 mmol) and THF (2 mL) was treated with isopropylsulfonyl chloride (0.15 mmol). The mixture was stirred for 18 h at room temperature. The solvent was removed under reduced pressure and the residue was diluted with EtOAc and washed sequentially with saturated aqueous NaHCO$_3$, 1N HCl and saturated aqueous NaCl. The EtOAc fraction was dried over anhydrous Na$_2$SO$_4$, filtered, and the filtrate concentrated under reduced pressure. The residue was purified by silica preparative TLC to give compound 25. $^1$H NMR (400 MHz, ACETONITRILE-d3) δ ppm 1.20 (d, J=6.8 Hz, 6 H), 3.09 (quin, J=6.8 Hz, 1 H), 3.37 (s, 3 H), 3.91-3.98 (m, 2 H), 4.13 (dd, J=9.9, 6.3 Hz, 2 H), 5.07 (tt, J=6.4, 4.7 Hz, 1 H), 5.97 (s, 1 H), 6.90 (dd, J=8.3, 1.0 Hz, 1 H), 6.93-6.99 (m, 1 H), 7.09 (m, 2 H), 7.19 (m, 2 H), 7.28 (dd, J=7.7, 1.6 Hz, 1 H), 7.29-7.36 (m, 1 H). Mass spectrum (ESI, m/z): Calcd. for C$_{22}$H$_{24}$ClN$_3$O$_4$S, 462.1 (M+H), found, 462.1.

The compounds of Table 1, exemplified hereinbelow, were prepared according to the schemes and specific examples described herein.

TABLE 1

Compounds of Formula (I)

| Cpd No. | Structure |
|---|---|
| 1 | 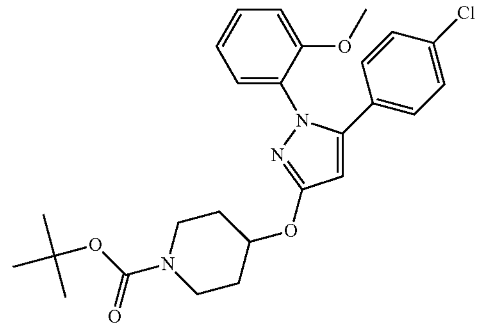 |
| 2 | 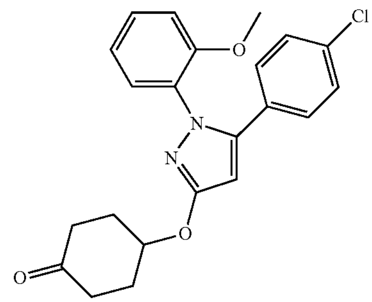 [SMILES: COc1ccccc1-n1nc(OC2CCC(=O)CC2)cc1-c1ccc(Cl)cc1] |
| 3 | 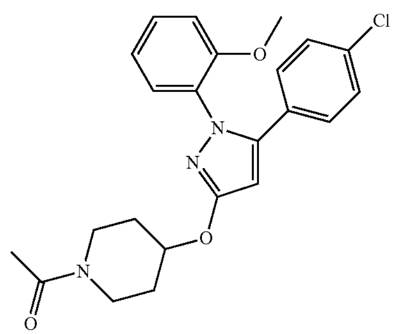 [SMILES: COc1ccccc1-n1nc(OC2CCN(C(C)=O)CC2)cc1-c1ccc(Cl)cc1] |
| 4 | 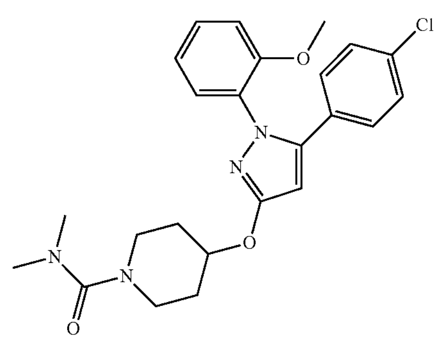 [SMILES: COc1ccccc1-n1nc(OC2CCN(C(=O)N(C)C)CC2)cc1-c1ccc(Cl)cc1] |

TABLE 1-continued

Compounds of Formula (I)

| Cpd No. | Structure |
|---|---|
| 5 | 1-(2-methoxyphenyl)-5-(4-chlorophenyl)-3-[(1-methanesulfonylpiperidin-4-yl)oxy]-1H-pyrazole |
| 6 | 1-(2-methoxyphenyl)-5-(4-chlorophenyl)-3-[(tetrahydro-2H-pyran-4-yl)oxy]-1H-pyrazole |
| 7 | 1-(2-methoxyphenyl)-5-(4-chlorophenyl)-3-[(tetrahydro-2H-thiopyran-4-yl)oxy]-1H-pyrazole |
| 8 | 1-(2-methoxyphenyl)-5-(4-chlorophenyl)-3-[(1-(2,2,2-trifluoroethyl)piperidin-4-yl)oxy]-1H-pyrazole |
| 9 | 1-(2-methoxyphenyl)-5-(4-chlorophenyl)-3-[(1-trifluoroacetylpiperidin-4-yl)oxy]-1H-pyrazole |
| 10 | 1-(2-methoxyphenyl)-5-(4-chlorophenyl)-3-[(1,1-dioxo-tetrahydro-2H-thiopyran-4-yl)oxy]-1H-pyrazole |
| 11 | 1-(2-methoxyphenyl)-5-(4-chlorophenyl)-3-[(trans-4-(tert-butoxycarbonylamino)cyclohexyl)oxy]-1H-pyrazole |
| 12 | 1-(2-methoxyphenyl)-5-(4-chlorophenyl)-3-[(trans-4-aminocyclohexyl)oxy]-1H-pyrazole |
| 13 | 1-(2-methoxyphenyl)-5-(4-chlorophenyl)-3-[(trans-4-(trifluoroacetamido)cyclohexyl)oxy]-1H-pyrazole |

TABLE 1-continued

Compounds of Formula (I)

| Cpd No. | Structure |
|---|---|
| 14 | (structure) |
| 15 | (structure) |
| 16 | (structure) |
| 17 | (structure) |
| 18 | (structure) |
| 19 | (structure) |
| 20 | (structure) |
| 21 | (structure) |

TABLE 1-continued

Compounds of Formula (I)

| Cpd No. | Structure |
|---|---|
| 22 | *tert-butyl 3-((1-(2-methoxyphenyl)-5-(4-chlorophenyl)-1H-pyrazol-3-yl)oxy)azetidine-1-carboxylate* |
| 23 | *1-(2-methoxyphenyl)-5-(4-chlorophenyl)-3-((2,2,6,6-tetramethyltetrahydro-2H-pyran-4-yl)oxy)-1H-pyrazole* |
| 24 | *5-(4-chlorophenyl)-1-(2-tert-butoxyphenyl)-3-((1-(methylsulfonyl)piperidin-4-yl)oxy)-1H-pyrazole* |
| 25 | *5-(4-chlorophenyl)-1-(2-methoxyphenyl)-3-((1-(isopropylsulfonyl)azetidin-3-yl)oxy)-1H-pyrazole* |
| 26 | *5-(4-chlorophenyl)-1-(2-methoxyphenyl)-3-((1-(methylsulfonyl)azetidin-3-yl)oxy)-1H-pyrazole* |
| 27 | *(3-((5-(4-chlorophenyl)-1-(2-methoxyphenyl)-1H-pyrazol-3-yl)oxy)azetidin-1-yl)(phenyl)methanone* |
| 28 | *5-(4-chlorophenyl)-1-(2-isopropoxyphenyl)-3-((1-(isopropylsulfonyl)piperidin-4-yl)oxy)-1H-pyrazole* |
| 29 | *3-((5-(4-chlorophenyl)-1-(3-methoxypyridin-2-yl)-1H-pyrazol-3-yl)oxy)-N-methoxy-N-methylazetidine-1-carboxamide* |

TABLE 1-continued

Compounds of Formula (I)

| Cpd No. | Structure |
|---|---|
| 30 | 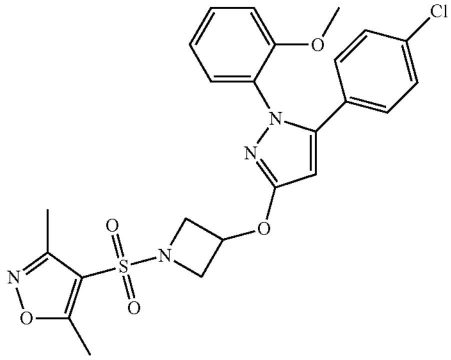 [SMILES: COc1ccccc1-n1nc(OC2CN(S(=O)(=O)c3c(C)noc3C)C2)cc1-c1ccc(Cl)cc1] |
| 31 | 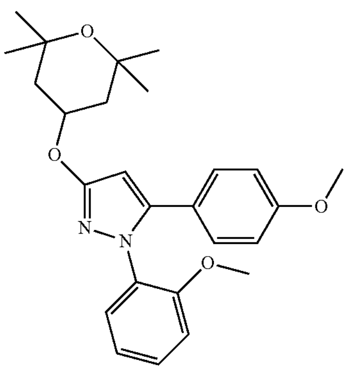 |
| 32 | 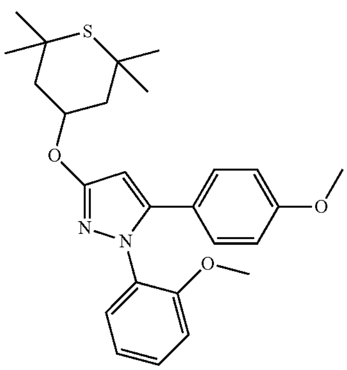 |
| 33 | 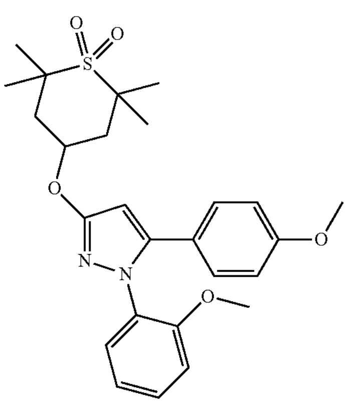 |
| 34 | 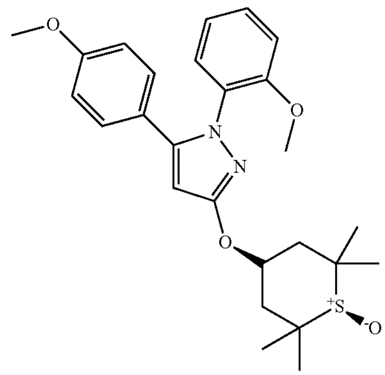 |
| 35 | 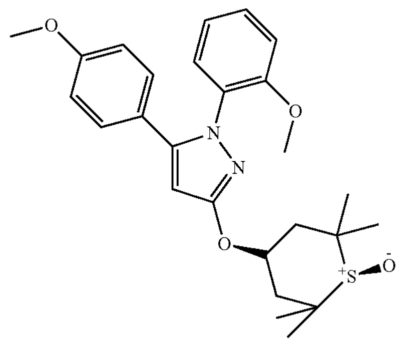 |
| 36 | 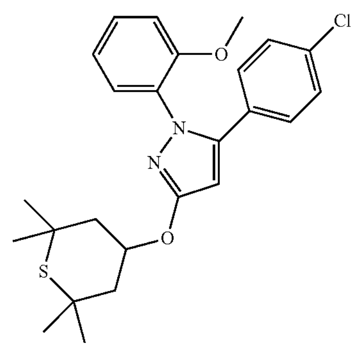 [SMILES: COc1ccccc1-n1nc(OC2CC(C)(C)SC(C)(C)C2)cc1-c1ccc(Cl)cc1] |
| 37 | 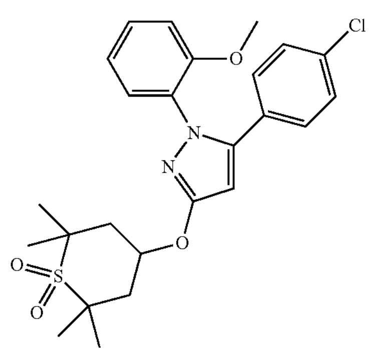 [SMILES: COc1ccccc1-n1nc(OC2CC(C)(C)S(=O)(=O)C(C)(C)C2)cc1-c1ccc(Cl)cc1] |

TABLE 1-continued
Compounds of Formula (I)
| Cpd No. | Structure |
|---|---|
| 38 |  (1s, 4s) |
| 39 | (1r, 4r) |
| 40 | 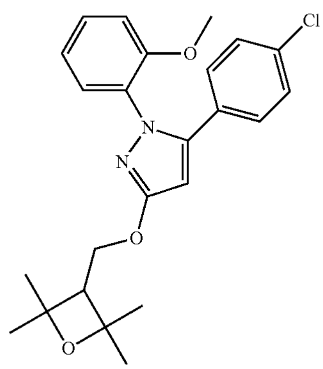 [SMILES: COc1ccccc1-n1nc(OCC2C(C)(C)OC2(C)C)cc1-c1ccc(Cl)cc1] |
| 41 | 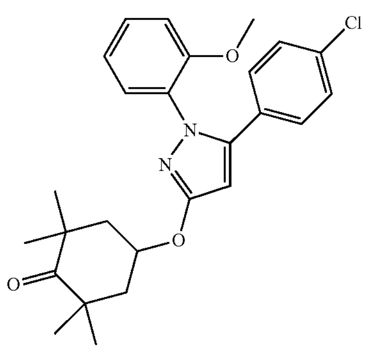 [SMILES: COc1ccccc1-n1nc(OC2CC(C)(C)C(=O)C(C)(C)C2)cc1-c1ccc(Cl)cc1] |
| 42 | |
| 43 | |
| 44 | |
| 45 | |

TABLE 1-continued

Compounds of Formula (I)

| Cpd No. | Structure |
|---|---|
| 46 | (4-cyanophenyl / 2-methoxyphenyl pyrazole with 2,2,6,6-tetramethyl-thiopyran S-oxide ether) |

BIOLOGICAL EXAMPLES

In Vitro Assays

Example 1

Functional Assay: Antagonism of N-Type Calcium Channel

A stable cell line (HEK parent) co-expressing the $\alpha_{1B}$ (Cav2.2), $\beta_3$ and $\alpha_2\delta$ subunits of the N-type calcium channel subunits was used. These cells were routinely grown as monolayers in low glucose-containing Dulbecco's Modified Eagle Medium supplemented with 10% FBS, 2 mM L-glutamine, 100 I.U./mL penicillin, 100 μg/mL streptomycin, 400 μg/mL G418 and 200 μg/mL Zeocin (split ratio=1:5). Cells were maintained in 5% $CO_2$ at 37° C. Compounds of Formula (I) were prepared as 10 mM stocks in DMSO from neat compound, if available. Otherwise, the 5 or 10 mM DMSO stock solutions provided in-house were used.

Calcium mobilization responses to KCl depolarization were evaluated by measuring the intensity of calcium-mediated fluorescent signal in the presence of BD Calcium Assay Dye (BD Biosciences, Franklin Lakes, N.J., U.S.A.), utilizing a Functional Drug Screening System (FDSS) by Hamamatsu Corporation (Bridgewater, N.J. U.S.A.).

Twenty-four hr prior to assay, cells were seeded in clear-base poly-D-lysine-coated 384-well plates (BD Biosciences) at a density of 5,000 cells per well in culture medium and grown overnight in 5% $CO_2$ at 37° C. On the day of assay, growth media were removed, and cells were loaded with BD calcium assay dye (BD Biosciences) for 35 min at 37° C. under 5% $CO_2$ and then for 25 min at room temp. Utilizing the FDSS, cells were exposed to representative compounds of Formula (I) at varying concentrations, and intracellular calcium was measured for 5 min prior to the addition of 50 mM KCl for an additional 3 min of measurement.
Calculations and Formulas $IC_{50}$ values for representative compounds of Formula (I) were determined from six-point concentration-response experiments and represent the concentration of said compound required to inhibit 50% of the maximal response. Maximal fluorescence intensity (FI) achieved upon addition of 50 mM KCl was exported from the FDSS software and further analyzed using GraphPad Prism 3.02 (Graph Pad Software Inc., San Diego, Calif., U.S.A.). Data were normalized to the maximum average counts from quadruplicate wells for each condition in the presence of 50 mM KCl and to the minimum average counts in the presence of buffer. Theoretical curves were generated using nonlinear regression curve-fitting analysis of either sigmoidal concentration-response or sigmoidal concentration-response (variable slope), and the $IC_{50}$ values with the best-fit curve determined by GraphPad Prism were reported. Resultant data are shown in Table 2.

TABLE 2

| Compound No | FDSS $IC_{50}$ (μM) | % Inhibition (%) at 0.33 μM |
|---|---|---|
| 1 | 0.03 | |
| 2 | 0.028 | |
| 3 | 0.026 | |
| 4 | 0.014 | |
| 5 | 0.015 | |
| 6 | 0.015 | 98 |
| 7 | 0.028 | |
| 8 | 0.031 | |
| 9 | 0.0314 | |
| 10 | 0.03 | |
| 11 | 0.062 | |
| 12 | 0.4 | |
| 13 | 0.011 | |
| 14 | 0.024 | |
| 15 | 0.009 | |
| 16 | 0.041 | |
| 17 | 0.081 | |
| 18 | 0.05 | |
| 19 | 0.0985 | |
| 20 | 0.0215 | |
| 21 | 0.036 | 95 |
| 22 | 0.067 | 90 |
| 23 | 0.0076 | 96 |
| 24 | | 57 |
| 25 | 0.036 | 92 |
| 26 | 0.031 | 91 |
| 27 | 0.085 | 87 |
| 28 | 0.007 | 96 |
| 29 | 0.014 | 94 |
| 30 | 0.008 | 93 |
| 31 | 0.0094 | 97 |
| 32 | 0.006 | 93 |
| 33 | 0.003 | 94 |
| 34 | 0.0045 | 94 |
| 35 | 0.0076 | 91 |
| 36 | 0.0059 | 91 |
| 37 | 0.0019 | 98 |
| 38 | 0.0027 | 98 |
| 39 | 0.0015 | 99 |
| 40 | 0.0031 | 95 |
| 41 | 0.0097 | 92 |
| 42 | 0.039 | 78 |
| 43 | 0.0072 | 90 |
| 44 | 0.012 | 87 |
| 45 | 0.0024 | 99 |
| 46 | 0.014 | 90 |

Example 2

Automated Electrophysiology Assay

Cells were grown in T175 flasks to 50%-90% confluence. At the time of use, cells were enzymatically treated with Detachin (Genlantis, San Diego, Calif. USA), centrifuged, rinsed, and resuspended in 293 SFM II media (Life Technologies, Grand Island, N.Y. U.S.A.) supplemented with 25 mM HEPES (Sigma-Aldrich, St. Louis, Mo. U.S.A.) to a concentration of $2\text{-}3 \times 10^6$ cells/mL. Cells were added to the automated cell preparation station on the QPatch-HT (Sophion Biosciences, North Brunswick, N.J. U.S.A.), and following a 10- to30-min recovery period with gentle stirring, the assay protocol was initiated. During the automated cell preparation, cells were collected, centrifuged and resuspended in an extracellular (EC) solution containing 132 mM NaCl, 1.8 mM $CaCl_2$, 5.4 mM KCl, 0.8 mM $MgCl_2$, 10 mM glucose, and 10 mM HEPES (pH=7.4), adjusted with sucrose to approximately 315 mOsm. The QPlate was primed with an intracellular solution containing 135 mM CsCl, 10 mM EGTA, 4 MgATP, 0.3 NaGTP, and 20 mM HEPES (pH=7.2), adjusted to approximately 290 mOsm with deionized water and the EC solution. Cells were added to the prepared QPlate wells by robotic pipettes of the QPatch-HT.

For cells determined to be in stable whole-cell patch clamp, the EC solution was replaced with a barium (Ba)/triethylammonium (TEA) solution containing 140 mM TEA-Cl, 10 mM $BaCl_2$, 0.8 mM $MgCl_2$, 10 mM glucose and 10 mM HEPES (pH=7.4). High (40 mM) $BaCl_2$ concentrations were made with adjustments to TEA-Cl (90 mM) to maintain the osmolarity. From a resting potential of −80 mV, a train of depolarizing pulses (15 pulses at 5 Hz, +20 mV) was delivered to the cell once every 30 sec for eight trains (4 min total), and the resulting currents were measured during a control period (no compound). This protocol was repeated for each subsequent addition of control buffer with or without compound (three periods total, each with four trains). The current generated in the $1^{st}$ and $15^{th}$ pulses of the last train of each period in the presence of each drug concentration was normalized to the current generated during the control period at the respective pulses (representing low- and high-frequency stimulation, respectively). Data from both the second and third drug application periods were analyzed for each cell. A final addition of Ba/TEA solution containing 60-100 µM $CdCl_2$ was made to block all N-type current and to "zero" the currents for each cell. All buffer/compound additions were made using a "spitting" feature of the QPatch-HT, which added three repetitions of 5 µL solution at the beginning of each recording period.

To examine closed-state inactivation, cells were subjected to a channel-activating 50-msec depolarizing step pulse from −80 to +10 mV, followed by a 5-sec nonactivating step to voltages ranging from −130 to −60 mV in 10 mV increments and then a 50-ms step from −80 to +10 mV to assess the remaining current. Currents from the activating voltage pulse were normalized to the peak value of the test pulse following the −130 mV step and fit to a Boltzman equation to obtain the $V_{1/2}$. Roscovitine (Sigma-Aldrich) was prepared as a 100 mM stock in dimethyl sulfoxide and diluted to the indicated working concentrations. Tetrandrine (Sigma-Aldrich) was prepared as a 4 mM stock in acidic water (pH=2.0) and then diluted to working concentrations in the external solution. ω-Conotoxin MVIIA (Sigma-Aldrich) was prepared as a 0.3 mg/mL stock solution in water, with 0.1% bovine serum albumin V (Life Technologies). Compounds of Formula (I) were diluted first into dimethyl sulfoxide and then into 10% pluronic F-127 in water (Life Technologies), sonicated for 1 min and diluted into EC buffer. Vehicle controls were run in parallel in all experiments.

Unless otherwise indicated, statistics for comparing among electrophysiological results utilized a one-way analysis of variance with Fisher's least squares determination test for pair-wise comparison. Resultant data are shown in Tables 3 and 4, below.

TABLE 3

QPatch at Low Frequency

| Cpd No. | % Inhibition at 0.1 µM |
|---|---|
| 15 | 25 |
| 20 | 24 |
| 21 | 15 |
| 23 | 11 |
| 26 | 37 |
| 29 | −24 |
| 30 | 30 |
| 31 | 28 |

TABLE 4

QPatch at High Frequency

| Cpd No. | % Inhibition at 0.1 µM |
|---|---|
| 15 | 55 |
| 20 | 37 |
| 21 | 23 |
| 23 | 37 |
| 26 | 40 |
| 29 | 1 |
| 30 | 53 |
| 31 | 44 |

In Vivo Assay

Example 3

Complete Freund's Adjuvant (CFA)-Induced Hyperalgesia

The intraplantar injection of complete Freund's adjuvant (CFA) in rodents results in a long-lasting inflammatory reaction, characterized by a pronounced hypersensitivity to both thermal and mechanical stimuli, which peaks between 24-72 hr following injection and can last for several weeks. This test predicts the analgesic, anti-allodynic and/or anti-hyperalgesic effect of numerous efficacious clinical agents, including acetaminophen, NSAIDS, such as aspirin and ibuprofen, opioids, such as morphine, and especially the N-type calcium channel blocker ziconotide, which is marketed as Prialt® for the management of severe chronic pain, including several types of neuropathic pain.

To assess whether test compounds of Formula (I) reverse established hypersensitivity, a 100 µL of CFA (suspended in a 1:1 emulsion of saline and heat-killed *Mycobacterium tuberculosis* in mineral oil) was injected into a single hind paw of Sprague-Dawley rats (typically males ranging from 150-350 g).

Each rat was placed in a test chamber on a warm glass surface and allowed to acclimate for approximately 10 min. A radiant thermal stimulus (beam of light) was then focused through the glass onto the plantar surface of each hind paw in turn. The thermal stimulus was automatically shut off by a photoelectric relay when the paw was moved or when the cut-off time was reached (20 sec for radiant heat at ~5 Amps). An initial (baseline) response latency to the thermal stimulus was recorded for each animal prior to the injection of CFA. Twenty-four hr following intraplantar CFA injection, the response latency of the animal to the thermal stimulus was then re-evaluated and compared to the animal's baseline response time. Only rats that exhibited at least a 25% reduction in response latency (i.e., hyperalgesia) were included in further analysis. Immediately following the post-CFA latency assessment, test compound or vehicle (usually Solutol, hydroxypropyl methylcellulose, hydroxypropyl beta-cyclodextrin or PEG-400) was administered i.p. or p.o. to rats. Post-compound treatment withdrawal latencies were assessed at fixed time intervals, typically 30, 60 and 120 min. Resultant data for Compound 23 of Formula (I) are shown in FIG. 1.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of Formula (I)

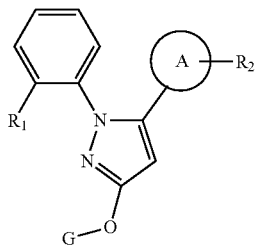

Formula (I)

wherein $R^1$ is selected from the group consisting of $C_{1-4}$alkyl, $C_{1-4}$alkoxy, di($C_{1-4}$alkyl)amino, chloro, trifluoromethoxy, trifluoromethyl, and cyano;

ring A is phenyl or a heteroaryl selected from the group consisting of pyridinyl, thienyl, benzofuranyl, quinolinyl, and indolyl;

$R^2$ is selected from the group consisting of $C_{1-4}$alkyl, $C_{1-4}$alkoxy, $C_{1-4}$alkylthio, cyano, fluoro, chloro, hydroxy, and di($C_{1-4}$alkyl)amino;

G is G1, G2, G3, or G4;

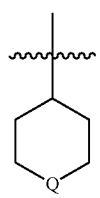

G1

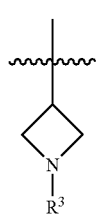

G2

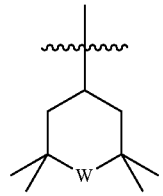

G3

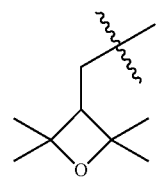

G4 wherein

Q is selected from the group consisting of O, S, $SO_2$, N—$R^4$, $CH_2$, $CH(R^5)$, $CF_2$, $C(CH_3)_2$, $C(O)$, and a spirofused

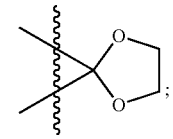

;

W is selected from the group consisting of O, S, CH(OH), C(O), S(O), $SO_2$, and N—$R^4$;

$R^3$ and $R^4$ are each independently selected from the group consisting of 2,2,2-trifluoroethyl, di($C_{1-4}$alkyl)aminocarbonyl, N-methoxy-N-methylaminocarbonyl, phenylcarbonyl, $C_{1-4}$alkylcarbonyl, trifluoromethylcarbonyl, $C_{1-4}$alkoxycarbonyl, $C_{3-7}$cycloalkylsulfonyl, trifluoromethylsulfonyl, and 3,5-dimethylisoxazol-4-ylsulfonyl;

$R^5$ is trifluoromethylcarbonylamino, amino, or $C_{1-4}$alkoxycarbonylamino; and enantiomers, diastereomers, and pharmaceutically acceptable salts thereof.

2. The compound of claim 1 wherein $R^1$ is selected from the group consisting of $C_{1-4}$alkyl, $C_{1-4}$alkoxy, chloro, trifluoromethoxy, trifluoromethyl, and cyano.

3. The compound of claim 2 wherein $R^1$ is selected from the group consisting of $C_{1-4}$alkyl, $C_{1-4}$alkoxy, chloro, and trifluoromethyl.

4. The compound of claim 3 wherein $R^1$ is selected from the group consisting of methyl, ethyl, methoxy, and isopropyloxy.

5. The compound of claim 1 wherein ring A is phenyl.

6. The compound of claim 5 wherein ring A is phenyl substituted at the 4-position.

7. The compound of claim 1 wherein $R^2$ is selected from the group consisting of $C_{1-4}$alkoxy, cyano, and chloro.

8. The compound of claim 7 wherein $R^2$ is selected from the group consisting of methoxy, cyano, and chloro.

9. The compound of claim 1 wherein G is G1, G2, G3, or G4;

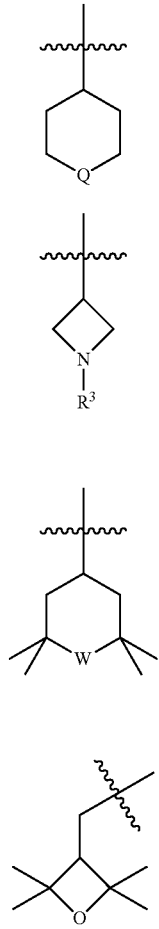

G1

G2

G3

G4 wherein

Q is selected from the group consisting of O, S, SO$_2$, N—R$^4$, CH$_2$, CH(R$^5$), CF$_2$, C(CH$_3$)$_2$, C(O), and a spirofused

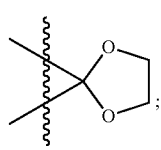

;

W is selected from the group consisting of O, S, CH(OH), C(O), S(O), and SO$_2$;

R$^3$ and R$^4$ are each independently selected from the group consisting of 2,2,2-trifluoroethyl, di(C$_{1-4}$alkyl)aminocarbonyl, N-methoxy-N-methylaminocarbonyl, phenylcarbonyl, C$_{1-4}$alkylcarbonyl, trifluoromethylcarbonyl, C$_{1-4}$alkoxycarbonyl, C$_{3-7}$cycloalkylsulfonyl, trifluoromethylsulfonyl, and 3,5-dimethylisoxazol-4-ylsulfonyl; and R$^5$ is trifluoromethylcarbonylamino or C$_{1-4}$alkoxycarbonylamino.

10. The compound of Formula (I) as in claim 1

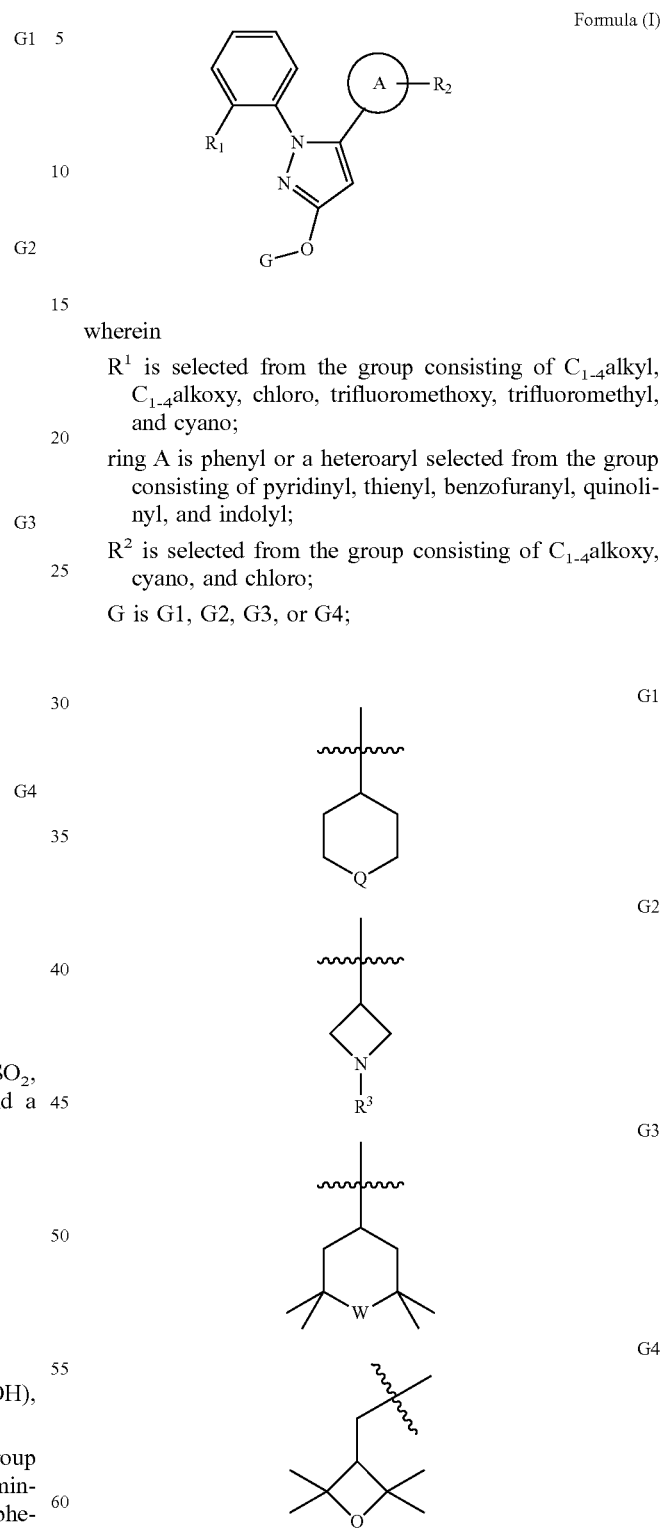

Formula (I)

wherein

R$^1$ is selected from the group consisting of C$_{1-4}$alkyl, C$_{1-4}$alkoxy, chloro, trifluoromethoxy, trifluoromethyl, and cyano;

ring A is phenyl or a heteroaryl selected from the group consisting of pyridinyl, thienyl, benzofuranyl, quinolinyl, and indolyl;

R$^2$ is selected from the group consisting of C$_{1-4}$alkoxy, cyano, and chloro;

G is G1, G2, G3, or G4;

wherein

Q is selected from the group consisting of O, S, SO$_2$, N—R$^4$, CH$_2$, CH(R$^5$), CF$_2$, C(CH$_3$)$_2$, C(O), and a spirofused

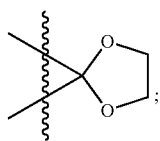

W is selected from the group consisting of O, S, CH(OH), C(O), S(O), and SO$_2$;

R$^3$ and R$^4$ are each independently selected from the group consisting of 2,2,2-trifluoroethyl, di(C$_{1-4}$alkyl)aminocarbonyl, N-methoxy-N-methylaminocarbonyl, phenylcarbonyl, C$_{1-4}$alkylcarbonyl, trifluoromethylcarbonyl, C$_{1-4}$alkoxycarbonyl, C$_{3-7}$cycloalkylsulfonyl, trifluoromethylsulfonyl, and 3,5-dimethylisoxazol-4-ylsulfonyl;

R$^5$ is trifluoromethylcarbonylamino or C$_{1-4}$alkoxycarbonylamino;

and enantiomers, diastereomers, and pharmaceutically acceptable salts thereof.

11. The compound of Formula (I) as in claim 1

Formula (I)

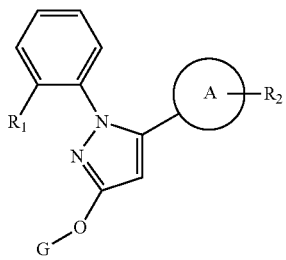

wherein

R$^1$ is selected from the group consisting of C$_{1-4}$alkyl, C$_{1-4}$alkoxy, chloro, and trifluoromethyl;

ring A is phenyl;

R$^2$ is selected from the group consisting of C$_{1-4}$alkoxy, cyano, and chloro;

G is G1, G2, G3, or G4;

G1

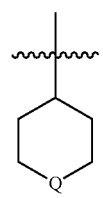

G2

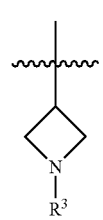

G3

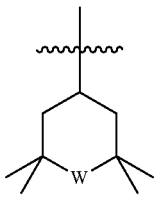

G4

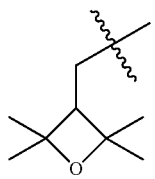

wherein

Q is selected from the group consisting of O, S, SO$_2$, N—R$^4$, CH$_2$, CH(R$^5$), CF$_2$, C(CH$_3$)$_2$, C(O), and a spirofused

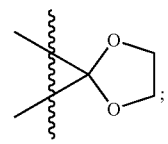

W is selected from the group consisting of O, S, CH(OH), C(O), S(O), and SO$_2$;

R$^3$ and R$^4$ are each independently selected from the group consisting of 2,2,2-trifluoroethyl, di(C$_{1-4}$alkyl)aminocarbonyl, N-methoxy-N-methylaminocarbonyl, phenylcarbonyl, C$_{1-4}$alkylcarbonyl, trifluoromethylcarbonyl, C$_{1-4}$alkoxycarbonyl, C$_{3-7}$cycloalkylsulfonyl, trifluoromethylsulfonyl, and 3,5-dimethylisoxazol-4-ylsulfonyl;

R$^5$ is trifluoromethylcarbonylamino or C$_{1-4}$alkoxycarbonylamino;

and enantiomers, diastereomers, and pharmaceutically acceptable salts thereof.

12. The compound of Formula (I) as in claim 1

Formula (I)

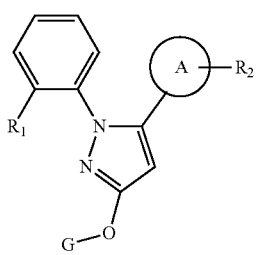

wherein

R$^1$ is selected from the group consisting of methyl, ethyl, methoxy, and isopropyloxy;

ring A is phenyl substituted at the 4-position;

R$^2$ is selected from the group consisting of methoxy, cyano, and chloro;

G is G1, G2, G3, or G4;

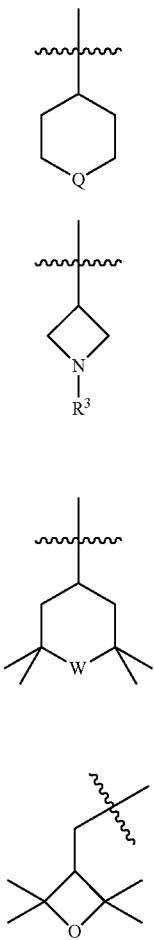

wherein

Q is selected from the group consisting of O, S, SO$_2$, N—R$^4$, CH$_2$, CH(R$^5$), CF$_2$, C(CH$_3$)$_2$, C(o), and a spirofused

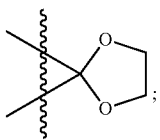

W is selected from the group consisting of O, S, CH(OH), C(O), S(O), and SO$_2$;

R$^3$ and R$^4$ are each independently selected from the group consisting of 2,2,2-trifluoroethyl, di(C$_{1-4}$alkyl)aminocarbonyl, N-methoxy-N-methylaminocarbonyl, phenylcarbonyl, C$_{1-4}$alkylcarbonyl, trifluoromethylcarbonyl, C$_{1-4}$alkoxycarbonyl, C$_{3-7}$cycloalkylsulfonyl, trifluoromethylsulfonyl, and 3,5-dimethylisoxazol-4-ylsulfonyl;

R$^5$ is trifluoromethylcarbonylamino or C$_{1-4}$alkoxycarbonylamino;

and enantiomers, diastereomers, and pharmaceutically acceptable salts thereof.

13. The compound of Formula (I) as in claim 1

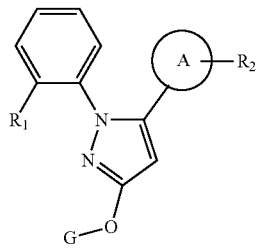

Formula (I)

selected from the group consisting of tert-Butyl 4-{[5-(4-chlorophenyl)-1-(2-methoxyphenyl)-1H-pyrazol-3-yl]oxy}piperidine-1-carboxylate;

4-{[5-(4-Chlorophenyl)-1-(2-methoxyphenyl)-1H-pyrazol-3-yl]oxy}cyclohexanone;

1-Acetyl-4-{[5-(4-chlorophenyl)-1-(2-methoxyphenyl)-1H-pyrazol-3-yl]oxy}piperidine;

4-{[5-(4-Chlorophenyl)-1-(2-methoxyphenyl)-1H-pyrazol-3-yl]oxy}-N,N-dimethylpiperidine-1-carboxamide;

5-(4-Chlorophenyl)-1-(2-methoxyphenyl)-3-(tetrahydro-2H-pyran-4-yloxy)-1H-pyrazole;

5-(4-Chlorophenyl)-1-(2-methoxyphenyl)-3-(tetrahydro-2H-thiopyran-4-yloxy)-1H-pyrazole;

4-{[5-(4-Chlorophenyl)-1-(2-methoxyphenyl)-1H-pyrazol-3-yl]oxy}-1-(2,2,2-trifluoroethyl)piperidine;

4-{[5-(4-Chlorophenyl)-1-(2-methoxyphenyl)-1H-pyrazol-3-yl]oxy}-1-(trifluoroacetyl)piperidine;

5-(4-Chlorophenyl)-3-[(1,1-dioxidotetrahydro-2H-thiopyran-4-yl)oxy]-1-(2-methoxyphenyl)-1H-pyrazole;

tert-Butyl(cis-4-{[5-(4-chlorophenyl)-1-(2-methoxyphenyl)-1H-pyrazol-3-yl]oxy}cyclohexyl)carbamate;

cis-4-{[5-(4-Chlorophenyl)-1-(2-methoxyphenyl)-1H-pyrazol-3-yl]oxy}cyclohexanamine;

N-(cis-4-{[5-(4-Chlorophenyl)-1-(2-methoxyphenyl)-1H-pyrazol-3-yl]oxy}cyclohexyl)-2,2,2-trifluoroacetamide;

4-{[5-(4-Chlorophenyl)-1-(2-methoxyphenyl)-1H-pyrazol-3-yl]oxy}-1-[(trifluoromethyl)sulfonyl]piperidine;

4-{[5-(4-Chlorophenyl)-1-(2-methoxyphenyl)-1H-pyrazol-3-yl]oxy}-1-(cyclopropylsulfonyl)piperidine;

5-(4-Chlorophenyl)-3-[(4,4-difluorocyclohexyl)oxy]-1-(2-methoxyphenyl)-1H-pyrazole;

5-(4-Chlorophenyl)-3-(1,4-dioxaspiro[4.5]dec-8-yloxy)-1-(2-ethylphenyl)-1H-pyrazole;

tert-Butyl 4-{[5-(4-chlorophenyl)-1-(2-ethylphenyl)-1H-pyrazol-3-yl]oxy}piperidine-1-carboxylate;

4-{[5-(4-Chlorophenyl)-1-(2-ethylphenyl)-1H-pyrazol-3-yl]oxy}-1-(methylsulfonyl)piperidine;

4-({5-(4-Chlorophenyl)-1-[2-(1-methylethoxy)phenyl]-1H-pyrazol-3-yl}oxy)-1-(methylsulfonyl)piperidine;

4-{[5-(4-Chlorophenyl)-1-(2-methoxyphenyl)-1H-pyrazol-3-yl]oxy}-1-[(1-methylethyl)sulfonyl]piperidine;

tert-Butyl 3-{[5-(4-chlorophenyl)-1-(2-methoxyphenyl)-1H-pyrazol-3-yl]oxy}azetidine-1-carboxylate;

5-(4-Chlorophenyl)-1-(2-methoxyphenyl)-3-[(2,2,6,6-tetramethyltetrahydro-2H-pyran-4-yl)oxy]-1H-pyrazole;

4-{[1-(2-tert-Butoxyphenyl)-5-(4-chlorophenyl)-1H-pyrazol-3-yl]oxy}-1-(methylsulfonyl)piperidine;

5-(4-Chlorophenyl)-1-(2-methoxyphenyl)-3-({1-[(1-methylethyl)sulfonyl]azetidin-3-yl}oxy)-1H-pyrazole;

5-(4-Chlorophenyl)-1-(2-methoxyphenyl)-3-{[1-(methylsulfonyl)azetidin-3-yl]oxy}-1H-pyrazole;

5-(4-Chlorophenyl)-1-(2-methoxyphenyl)-3-{[1-(phenyl-carbonyl)azetidin-3-yl]oxy}-1H-pyrazole;

4-({5-(4-Chlorophenyl)-1-[2-(1-methylethoxy)phenyl]-1H-pyrazol-3-yl}oxy)-1-[(1-methylethyl)sulfonyl]piperidine;

3-{[5-(4-Chlorophenyl)-1-(2-methoxyphenyl)-1H-pyrazol-3-yl]oxy}-N-methoxy-N-methylazetidine-1-carboxamide;

4-[(3-{[5-(4-Chlorophenyl)-1-(2-methoxyphenyl)-1H-pyrazol-3-yl]oxy}azetidin-1-yl)sulfonyl]-3,5-dimethylisoxazole;

1-(2-Methoxyphenyl)-5-(4-methoxyphenyl)-3-[(2,2,6,6-tetramethyltetrahydro-2H-pyran-4-yl)oxy]-1H-pyrazole;

1-(2-Methoxyphenyl)-5-(4-methoxyphenyl)-3-[(2,2,6,6-tetramethyltetrahydro-2H-thiopyran-4-yl)oxy]-1H-pyrazole;

1-(2-Methoxyphenyl)-5-(4-methoxyphenyl)-3-[(2,2,6,6-tetramethyl-1,1-dioxidotetrahydro-2H-thiopyran-4-yl)oxy]-1H-pyrazole;

1-(2-Methoxyphenyl)-5-(4-methoxyphenyl)-3-[(2,2,6,6-tetramethyl-1-oxidotetrahydro-2H-thiopyran-4-yl)oxy]-1H-pyrazole;

1-(2-Methoxyphenyl)-5-(4-methoxyphenyl)-3-[(2,2,6,6-tetramethyl-1-oxidotetrahydro-2H-thiopyran-4-yl)oxy]-1H-pyrazole;

5-(4-Chlorophenyl)-1-(2-methoxyphenyl)-3-[(2,2,6,6-tetramethyltetrahydro-2H-thiopyran-4-yl)oxy]-1H-pyrazole;

5-(4-Chlorophenyl)-1-(2-methoxyphenyl)-3-[(2,2,6,6-tetramethyl-1,1-dioxidotetrahydro-2H-thiopyran-4-yl)oxy]-1H-pyrazole;

5-(4-Chlorophenyl)-1-(2-methoxyphenyl)-3-{[(1s)-2,2,6,6-tetramethyl-1-oxidotetrahydro-2H-thiopyran-4-yl]oxy}-1H-pyrazole;

5-(4-Chlorophenyl)-1-(2-methoxyphenyl)-3-{[(1r)-2,2,6,6-tetramethyl-1-oxidotetrahydro-2H-thiopyran-4-yl]oxy}-1H-pyrazole;

5-(4-Chlorophenyl)-1-(2-methoxyphenyl)-3-[(2,2,4,4-tetramethyloxetan-3-yl)methoxy]-1H-pyrazole;

4-{[5-(4-Chlorophenyl)-1-(2-methoxyphenyl)-1H-pyrazol-3-yl]oxy}-2,2,6,6-tetramethylcyclohexanone;

4-{[5-(4-Chlorophenyl)-1-(2-methoxyphenyl)-1H-pyrazol-3-yl]oxy}-2,2,6,6-tetramethylcyclohexanol;

4-{1-(2-Methoxyphenyl)-3-[(2,2,6,6-tetramethyltetrahydro-2H-pyran-4-yl)oxy]-1H-pyrazol-5-yl}benzonitrile;

4-{1-(2-Methoxyphenyl)-3-[(2,2,6,6-tetramethyltetrahydro-2H-thiopyran-4-yl)oxy]-1H-pyrazol-5-yl}benzonitrile;

4-{1-(2-Methoxyphenyl)-3-[(2,2,6,6-tetramethyl-1,1-dioxidotetrahydro-2H-thiopyran-4-yl)oxy]-1H-pyrazol-5-yl}benzonitrile;

4-[1-(2-Methoxyphenyl)-3-{[(1s)-2,2,6,6-tetramethyl-1-oxidotetrahydro-2H-thiopyran-4-yl]oxy}-1H-pyrazol-5-yl]benzonitrile;

and pharmaceutically acceptable salt forms thereof.

14. A pharmaceutical composition comprising a compound of claim 1 or 13 and at least one of a pharmaceutically acceptable carrier, a pharmaceutically acceptable excipient and a pharmaceutically acceptable diluent.

15. A pharmaceutical composition of claim 14, wherein the composition is a solid oral dosage form.

16. A pharmaceutical composition of claim 14, wherein the composition is a syrup, an elixir or a suspension.

17. A method for treating inflammatory pain in a subject in need thereof, comprising administering to the subject a therapeutically effective amount of a compound of claim 1 or 13.

18. The method of claim 17 wherein the inflammatory pain is due to inflammatory bowel disease, visceral pain, migraine, post-operative pain, osteoarthritis, rheumatoid arthritis, back pain, lower back pain, joint pain, abdominal pain, chest pain, labor pain, musculoskeletal diseases, skin diseases, toothache, pyresis, burn, sunburn, snake bite, venomous snake bite, spider bite, insect sting, neurogenic/overactive bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain due to physical trauma, headache, sinus headache, tension headache or arachnoiditis.

19. A method for treating neuropathic pain in a subject in need thereof, comprising administering to the subject a therapeutically effective amount of a compound of claim 1 or 13.

20. The method of claim 19 wherein the neuropathic pain is cancer pain, neurological disorders, spine and peripheral nerve surgery, brain tumor, traumatic brain injury (TBI), chemotherapy-induced pain, pain chronification, radicular pain, HIV pain, spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, postherpetic neuralgia, causalgia, red neuralgia, Sluder's neuralgia, splenopalatine neuralgia, supraorbital neuralgia, trigeminal neuralgia, vulvodynia, or vidian neuralgia.

* * * * *